(12) United States Patent
Neville

(10) Patent No.: US 8,653,242 B2
(45) Date of Patent: Feb. 18, 2014

(54) **THERAPEUTIC ANTIBODIES AGAINST FLAGELLATED *PSEUDOMONAS AERUGINOSA***

(75) Inventor: Lewis F. Neville, Rehovot (IL)

(73) Assignee: Lostam Pharmaceuticals Ltd., Nazareth (IL)

( * ) Notice: Subject to any disclaimer, the term of this patent is extended or adjusted under 35 U.S.C. 154(b) by 0 days.

(21) Appl. No.: 13/582,584

(22) PCT Filed: Mar. 1, 2011

(86) PCT No.: PCT/IL2011/000208
§ 371 (c)(1),
(2), (4) Date: Sep. 4, 2012

(87) PCT Pub. No.: WO2011/107989
PCT Pub. Date: Sep. 9, 2011

(65) Prior Publication Data
US 2013/0096282 A1    Apr. 18, 2013

Related U.S. Application Data

(60) Provisional application No. 61/309,178, filed on Mar. 1, 2010, provisional application No. 61/379,471, filed on Sep. 2, 2010.

(51) Int. Cl.
*A61K 39/00* (2006.01)
(52) U.S. Cl.
USPC ........................................................ 530/387.1
(58) Field of Classification Search
None
See application file for complete search history.

(56) References Cited

U.S. PATENT DOCUMENTS

2002/0155537 A1    10/2002    Carter

FOREIGN PATENT DOCUMENTS

GB            2192185 A       1/1988

OTHER PUBLICATIONS

Landsperger, Infection and Immunity, vol. 62, No. 11, p. 4825-4830, 1994.*
Rosok, Mae Joanne et al., "Generation and Characterization of Murine Antiflagellum Monoclonal Antibodies That Are Protective against Lethal Challenge with *Pseudomonas aeruginosa*," Infection and Immunity, vol. 58(12) pp. 3819-3828. (1990).
Oishi Kazunori et al; "Therapeutic effects of a human antiflagella monoclonal antibody in a neutropenic murine model of *Pseudomonas aeruginosa* pneumonia" Antimicrobial Agents and Chemotherapy Vo.1 37. No. 2 pp. 164-170 (1993).
Landsperger WJ et al; "Inhibition of bacterial motility with human antiflagellar monoclonal antibodies attenuates *Pseudomonas aeruginosa*-induced pneumonia in the immunocompetent rat" Infection and immunity 62(11):pp. 4825-4830. (1994).
Matsumoto T et al; "Effect of Antiflagellar Human Monoclonal Antibody on Gut-Derived *Pseudomonas aeruginosa* Sepsis in Mice" Clinical and Diagnostic Laboratory Immunology 6(4): pp. 537-541. (1999).
Eric T. Weimer, et al; "A Fusion Protein Vaccine Containing OprF Epitope 8, Oprl, and Type A and B Flagellins Promotes Enhanced Clearance of Nonmucoid *Pseudomonas aeruginosa*" Infection and Immunity 77 pp. 2356-2366. (2009).
Dafne Muller and Roland E. Kontermann "Handbook of Therapeutic antibodies; Part III, chapter 2: Bispecific Antibodies" pp. 345-378. (2007).
Barnea Yoav et al; "Therapy with anti-flagellin A monoclonal antibody limits *Pseudomonas aeruginosa* invasiveness in a mouse burn wound sepsis model" Burns vol. 35, Issue 3, pp. 390-396 (2009).
Drake D, and Montie TC; "Protection against *Pseudomonas aeruginosa* infection by passive transfer of anti-flagellar serum". Can. J. Microbiol.vol. 33: pp. 755-763. (1987).

* cited by examiner

*Primary Examiner* — Brad Duffy
*Assistant Examiner* — Nelson B Moseley, II
(74) *Attorney, Agent, or Firm* — Browdy and Neimark, PLLC

(57) ABSTRACT

Improved antibodies are provided selected from human, dual-specific, chimeric or humanized antibodies, wherein said human chimeric and humanized antibodies specifically bind to flagellin type A or type B of *P. aeruginosa*, and said dual-specific antibodies specifically binds to flagella type A and type B of *Pseudomonas aeruginosa*, and said antibodies are protective against infection caused by *P. aeruginosa*. These antibodies as well as pharmaceutical composition comprising them are useful for the treatment of indications caused by *P. aeruginosa* infection.

9 Claims, 15 Drawing Sheets

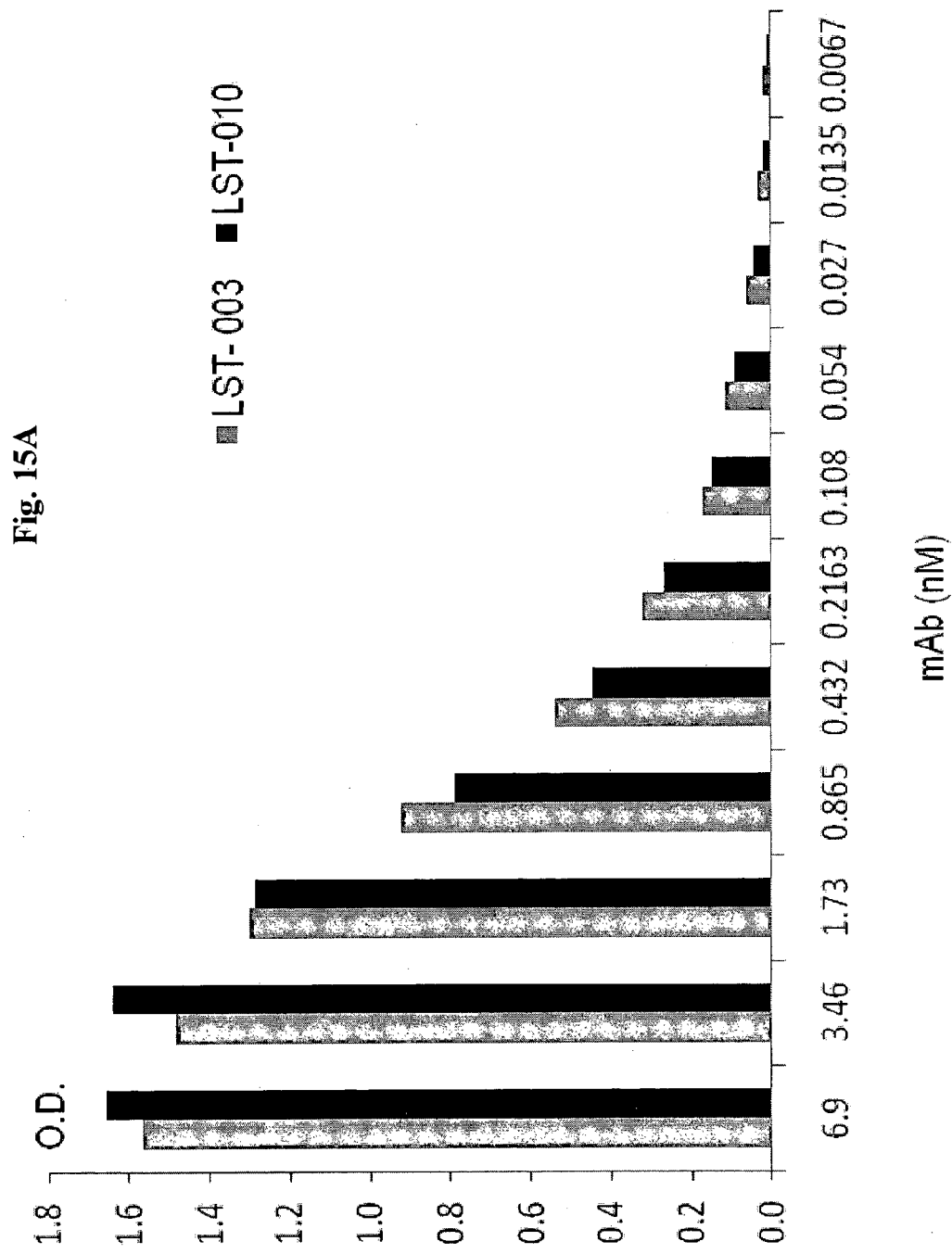

THERAPEUTIC ANTIBODIES AGAINST FLAGELLATED *PSEUDOMONAS AERUGINOSA*

TECHNICAL FIELD

The present invention relates to antibodies that specifically binds to flagella type A or type B of *P. aeruginosa*, or specifically binds to flagellin type A and type B of *P. aeruginosa*, but excluding mouse monoclonal antibodies, to pharmaceutical compositions comprising them and to methods for prophylactic or therapeutic treatment of infections caused by these bacteria.

BACKGROUND ART

*Pseudomonas aeruginosa* is an opportunistic pathogen that causes a variety of acute infections especially in cystic fibrosis patients, mechanically ventilated patients, burn victims and immunocompromised individuals. *P. aeruginosa* infections are recognized by the medical community as particularly worrisome and difficult to treat, especially multidrug resistant (MDR) strains in the hospital setting. A patient's prognosis for recovery from an infection caused by *P. aeruginosa* is enhanced when the diagnosis is made and appropriate treatment initiated as early in the course of the infection as possible, before the number of bacteria in the host becomes overwhelming and much more difficult to bring under control.

Patients suffering from major burns are especially vulnerable as they have extensive disruption of the skin barrier, with a concurrent suppression of the immune system. These conditions expose the burn area to bacterial wound colonization that can lead to burn wound infection, sepsis, multi-organ failure and subsequent death. Bacterial infection is the leading cause of death in major burns (responsible to 50-80% of overall thermal injury mortality), and *P. aeruginosa* is the most prevalent pathogen isolated from burn wound infections mainly due to its high persistence in the environment and its high intrinsic antibiotic resistance. Moreover, excessive antibiotic pressure in burn units has resulted in the emergence of multidrug-resistant strains of *P. aeruginosa* (Edward-Jones et al., 2003, Singh et al., 2003), the emergence of which underscores the clinical need to develop new classes of antibacterial therapeutics that can target centrally important proteins implicated in *P. aeruginosa* virulence.

*P. aeruginosa* is the scourge of hospital-associated pneumonias (HAP) of which ventilator-associated pneumonia (VAP) is routinely observed in Intensive Care Units. *P. aeruginosa* also causes infections in immune suppressed individuals (eg. cancer patients, patients awaiting transplantation, AIDS patients, premature babies). Also, *P. aeruginosa* causes infections at surgical sites, is responsible for urinary tract infections and of course is a relentless pulmonary infection in Cystic Fibrosis patients. Additionally, patients suffering from chronic obstructive pulmonary dysfunction (COPD) and bronchiectasis are highly susceptible to *P. aeruginosa* infections. Healthy individuals may also be susceptible to *P. aeruginosa*; for example, contact lens users are prone to *P. aeruginosa* infections and Swimmer's ear (also called otitis externa) is often caused by *P. aeruginosa*.

Immunotherapeutic strategies focusing on immunization (active or passive) and treatment targeting *P. aeruginosa* virulence-associated factors, such as elastase, protease, and exotoxin A, have been described in the literature and have showed limited success in the prevention and treatment of *P. aeruginosa* infections in animal models (Drake et al., 1987; Landsperger et al., 1994; Matsumoto et al., 1999; Steiner et al., 1998; Eaves-Pyles et al., 1999). Moreover, anti-lipopolysaccharide antibodies were found to be ineffective against a broad spectrum of *P. aeruginosa* isolates because of the presence of various lipopolysaccharide serotypes.

Flagellin protein, the principal component of bacterial flagella, has long been recognized as an important virulence factor in *P. aeruginosa* infections. Two major antigenic groups of flagella have been identified; type A, also known as HE comprising five sub-types designated $a_{0-4}$, and type B, also known as H2, having no sub-groups (Lanyi et al, 1970; Ansorg, 1978). The 'propeller-like' rotation as a result of flagellin polymerization is crucial for bacterial locomotion and survival and it is a contributing factor to bacterial invasion. Indeed, sub-type monoclonal antibodies (mAbs) raised against endogenous *P. aeruginosa* flagellins have been shown to afford protection in different animal models of *P. aeruginosa* infection (Drake et al., 1987; Rosok et al., 1990; Oishi et al., 1993; Landsperger et al., 1994; Matsumoto et al., 1999). U.S. Pat. No. 4,834,976 discloses monoclonal antibodies or antigen binding fragment thereof capable of specifically reacting with *P. aeruginosa* bacteria flagella type A or type B, but not both, which are said to be protective in vivo against said bacteria.

The flagellum, which mediates rapid bacterial movement, has an important role in bacterial dissemination and ultimately the progression of local bacterial colonization into an overwhelming invasive disease. Studies using various gram-negative flagellated bacteria, as well as flagellin deletion strains have demonstrated that flagellin is a 'double-edged sword'. Besides its role in bacterial motility and cellular invasion, isolated flagellin protein or intact *P. aeruginosa* harboring the flagellum appendage, can trigger inflammatory cells to produce an array of different pro-inflammatory molecules, including those involved in innate immunity. Flagellin's mode of action is mediated through high affinity binding towards the Toll-5 receptor (TLR5) whose activation results in the nuclear translocation of NF-κB and Elk-1 with enhanced transcription of immune response genes. Recent molecular studies revealed that the proinflammatory induction by flagellin is located at both the N' and C'-terminal regions of the molecule, rendering flagella, a highly feasible, "appendage-like" target for immunotherapy. The noxious effects of flagellin clearly highlights flagellin's role in experimental systemic tissue injury and circulatory shock.

Recently, it has been shown that a large percentage of *P. aeruginosa* strains from CF patients are non-motile, yet do possess an intact flagellum (and associated flagellin proteins) which has been essentially rendered disabled in terms of motility. Nevertheless, these non-motile strains are still damaging since their disabled flagellin retains its biological activity at lung TLR5 causing profound local inflammation. Thus, antibodies targeting *P. aeruginosa* flagellin should be protective against both motile and non-motile (flagellin positive) strains. Because most clinical *P. aeruginosa* isolates are flagellated, and given that there are only two major antigenic types, antiflagellum immunotherapy has been proposed as a possible treatment for *P. aeruginosa* infections.

SUMMARY OF INVENTION

The present invention relates, in one aspect, to an antibody that specifically binds to flagella type A or type B of *P. aeruginosa*, or specifically binds to flagellin type A and type B of *P. aeruginosa*, but excluding a mouse monoclonal antibody. This antibody may be a fully human antibody or a chimeric, humanized or dual-specific antibody or an antigen-binding fragment of the antibody.

The antibody may be covalently linked, optionally via a cleavable linker, to an antibiotic agent and/or it may be covalently linked to a nonproteinaceous polymer, such as polyethyleneglycol.

The present invention further relates to a nucleic acid molecule comprising a nucleotide sequence which encodes the antibody of the present invention, to vectors comprising said nucleic acid molecule operably linked to a promoter capable of driving the expression of said nucleic acid molecule, and to a host cell, such as mouse myeloma NS0 and Chinese Hamster Ovary (CHO) cells, or plant cells, such as tobacco, carrot and rice cells, comprising the vector(s).

In yet another aspect, the present invention relates to a pharmaceutical composition comprising at least one antibody or antigen binding fragment thereof, according to the present invention, or said antibody or an antigen binding fragment of the antibody covalently linked to an antibiotic agent or a nonproteinaceous polymer, and a pharmaceutically acceptable carrier.

The present invention further relates to methods for treatment of a subject suffering from or being susceptible to infection caused by P. aeruginosa, comprising administering to said patient a therapeutically effective amount of an antibody according to the present invention or antigen binding fragment thereof, or a derivative of said antibody or fragment thereof or an antigen binding fragment of the antibody covalently linked to an antibiotic agent or a nonproteinaceous polymer.

In still another aspect, the present invention relates to a method for diagnosing and monitoring a host response to severe P. aeruginosa infection, comprising (a) obtaining a patient sample; (b) contacting said patient sample with an antibody of the invention; and (c) measuring binding of said antibody to said patient sample, wherein detection of binding of said antibody to said patient sample indicates the presence or level of P. aeruginosa in the patient sample. In order to facilitate convenient detection of the antibody, it may be labeled with a detectable label such as, but not limited to, antigenic peptide tags fluorophores, enzymes, luminescent compounds, radioisotopes and micro- or nano-particles.

In yet another aspect, the present invention relates to a kit for detecting P. aeruginosa in a biological sample comprising a container containing an antibody according to the present invention; a container containing a set of reagents required for the detection and quantification of said antibody; and instructions for use.

BRIEF DESCRIPTION OF DRAWINGS

FIG. 1 shows a schematic drawing of a dual-specific antibody using "knobs-into-holes" CH3 mutations. CH2 and CH3, second and third constant regions of human IgG1. Two chains are heterodimerized by "knobs-into-holes" engineered CH3 domains. Two naturally occurring hinge region disulfide bonds are indicated by horizontal lines.

FIG. 2 shows a schematic drawing of a dual-specific antibody consisting of a chimeric, humanized or human antibody (empty block arrow), for example LST-003, linked via a linker peptide (thin black arrow) to two single chain variable fragments (scFvs; filled block arrow), derived for example from LST-002, that are connected via a spacer peptide (dashed arrow).

FIG. 15A-B depict a comparisons of binding of the dual-specific LST-010 mAb as compared to LST-003 (A) or LST-004 (B) towards ELISA plates coated with purified PA flagellin type A (A) or purified PA flagellin type B (B). OD, Optical Density; abscissa, concentration (nM) of mAb added to each well.

DETAILED DESCRIPTION OF THE INVENTION

Figure 3A:
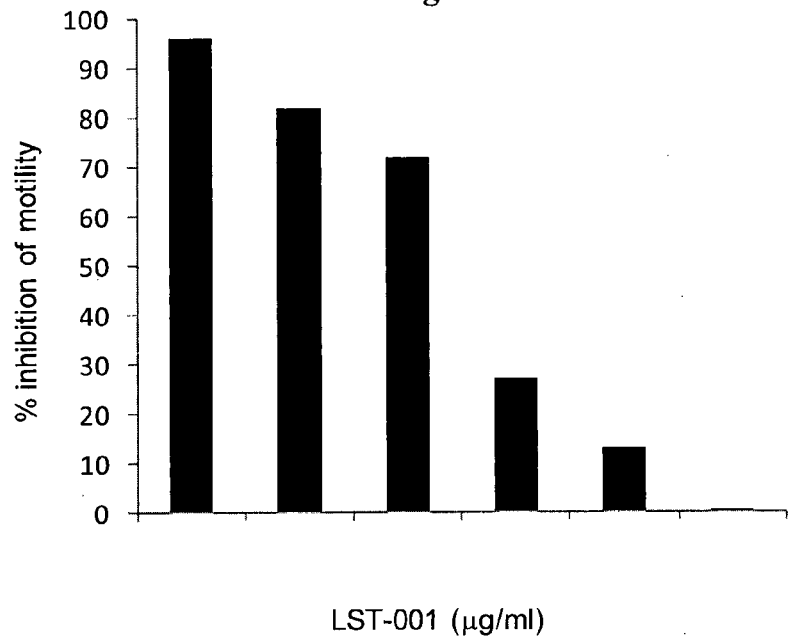
FIGS. 3A-B show motility of clinical P. aeruginosa (PA) strains PA 27853, known to harbor type A flagellin, in the presence of anti-flagella type A mAb (LST-001) antibody (A) or the multi-drug-resistant Ka02 PA strain and laboratory strain Pa01 (B). Quantitative data based on measurements done on the diameter of the halo formed by motile bacteria grown on agar is depicted.

An antibody molecule of the IgG type comprises two light chains and two heavy chains linked via disulfide bonds. Both the light chain and the heavy chain contains a domain of relatively variable amino acid sequences, known as the variable region, which in turn contains hypervariable regions, also known as complementarity-determining regions (CDR), that are interspersed among relatively conserved framework regions, as defined by Kabat (1970), Brochet et al (2008) or Chothia (1987; 1992). Together, the CDR and framework region determine the three-dimensional structure of the IgG binding site and thus, the antigen specificity of the antibody. The complete IgG molecule also contains a domain of relatively conserved amino acid sequences, called the constant region consisting of three constant domains ($C_H$1-3).

The IgG molecule is often referred to in terms of its functional fragments. Cleavage of an IgG with the protease papain produces two identical antigen-binding fragments (Fab) and an "Fc" fragment conferring the biological activity of the antibody, such as binding to the first component of the complement cascade or binding to Fc-receptor bearing cells, such as phagocytes, mast cells, neutrophils and natural killer cells. The Fc fragment comprises the heavy constant regions CH2 and CH3, and the Fab fragment comprises the heavy (CH1) and light (CL) constant regions and the variable regions of the heavy ($V_H$) and light ($V_L$) chains. The terms "Fab", "Fab-fragment" and "Fab-region" are used interchangeably herein.

Two mouse, and two human monoclonal antibodies have been disclosed in U.S. Pat. No. 4,834,976 that bind to flagellin proteins of P. aeruginosa. Two of the antibodies, the mouse FA6 IIG5 (ATCC HB9130) termed herein mouse LST-001 and the human 21B8 (ATCC CRL 9301), are specific to P. aeruginosa flagellin type A, and the two other antibodies, the mouse PaF4 IVES (ATCC HB9129), termed herein mouse LST-002, and the human 20H11 (ATCC CRL9300), termed herein LST-007, are specific to P. aeruginosa flagellin type B.

None of the above mouse antibodies is suitable alone as an active agent for treatment of P. aeruginosa infections, due to its murine origin. Monoclonal antibodies of murine origin are highly antigenic causing a human anti-mouse antibody (HAMA) response, and therefore often are rapidly removed from circulation and may be the cause of systemic inflammatory effects. Both mouse LST-001 and LST-002 antibodies, or derivatives thereof, were never developed into antibacterial drugs.

The above human antibodies are expressed in Epstein-Barr virus (EBV) transformed B-cells, which are an extremely poor source for commercial quantities of antibody. This is because the resultant lymphoblastoid cell line (LCL) that secretes the human antibodies grow very slowly and as aggregates requiring high concentrations of fetal bovine serum (15%) for support. In order to provide for the production of acceptable levels of antibody amenable for purification in serum-free media, the transformed B-cells may be fused with myeloma cells or heteromyeloma cells. Alternatively, the respective $V_H$ and $V_L$ genes of the antibodies must first be sequenced, linked to their appropriate human constant domains and sub-cloned into a suitable mammalian expression vector for recombinant expression in an appropriate eukaryotic cell line. Thereafter, further antibody versions can be created by for example expression of $V_H$ and $V_L$ (single chain fragments) derived from a single antibody, as shown hereinafter in Example 9. Alternatively, a single antibody molecule may comprise such fragments derived from two separate antibodies to create a dual-specific or heterodimeric molecule.

Described herein are novel improved antibodies specific for flagellar proteins of P. aeruginosa, which are protective in vivo against said bacteria. One preferred antibody is a fully human IgG antibody based on the variable regions of the human IgM monoclonal antibody LST-007. Other antibodies utilize the variable fragments of mouse LST-001 and LST-002 mAbs, or functional variants thereof, while reducing, i.e. abrogating or decreasing in a statistically or biologically significant manner, antigenicity of the antibodies when presented to the human immune system. In particular, the antibodies are specific for flagellin, type A and/or type B, as evidenced by their specific binding to purified flagellin or to flagella, either isolated or attached to a bacterial cell membrane. Several methods for producing antibodies with reduced antigenicity exist involving the reduction of antigenicity of non-human antibodies by replacing immunogenic regions with non-immunogenic regions, as disclosed in for example U.S. Pat. No. 6,881,557 (Foote), U.S. Pat. No. 5,869,619 (Studnicka), U.S. Pat. No. 5,225,539 (Winter et al.), Yamashita et al. (2007) and Almagro et al. (2008). For example, antibodies with reduced immunogenicity may be chimeric antibodies consisting of the Fab fragment of a non-human antibody, which contains the CDRs, fused to the constant region of a human antibody. A "humanized antibody" is a chimeric antibody in which a larger part of the protein is derived from human sequences. Commonly, humanized antibodies consists of 5-10% sequences derived from non-human antibodies and 90-95% sequences derived from human antibodies. Thus, the term "humanized antibody" as used herein refers to an antibody comprising the CDRs of a murine monoclonal antibody transplanted onto a human conserved framework region. In order to ensure that the binding specificity is maintained, certain "human" amino acids may be replaced with corresponding amino acids from the equivalent murine sequences.

The antibodies of the present invention may be specific for *P. aeruginosa* flagella type A or type B, or they may be dual-specific, i.e. they specifically bind to epitopes present on *P. aeruginosa* type A flagella and to epitopes present on *P. aeruginosa* type B flagella.

In preferred embodiments, the antibody is a human antibody comprising a human IgG constant region fused to human variable regions of an anti-*P. aeruginosa* monoclonal antibody that specifically binds to flagella type B.

Figures 1, 2:
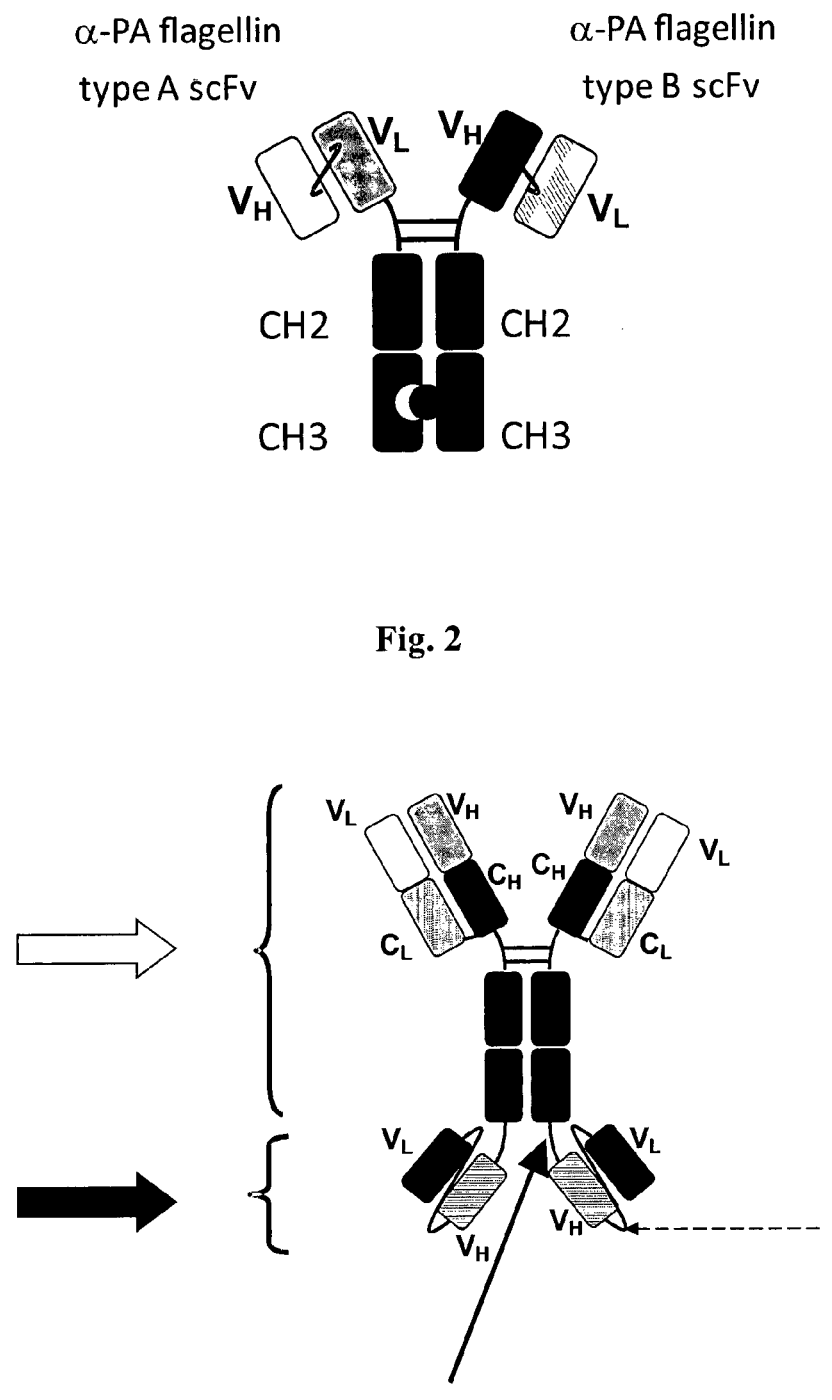

Many designs have been put forward for creating dual-specific antibodies. One example is based on the so called "knobs into holes" concept (U.S. Pat. No. 7,642,228) in which, in the case of antibodies, a first human IgG heavy chain molecule is associated with a second human IgG heavy chain molecule via an interface, said interface having introduced therein at least one protuberance or cavity such that: (a) the interface of the first human IgG heavy chain molecule comprises a protuberance that is positionable in a cavity in the interface of the second human IgG heavy chain molecule and/or (b) the interface of the first human IgG heavy chain molecule comprises a cavity that accommodates a protuberance of the second human IgG heavy chain molecule. In particular, a knob is created by replacing a small amino side chain at the interface between CH3 domains of the human IgG1 Fc region (hinge, constant region 2 and 3 of immunoglobulin heavy chain (CH2 and CH3), GenBank accession no. AF150959) with a larger one, whereas a hole is constructed by replacing a large side chain with a smaller one. Variable regions having specificity to a first antigen are fused, for example, to the first human IgG heavy chain molecule and other variable regions, having specificity to a second antigen, are fused to the second human IgG heavy chain molecule. Of course, the variable regions having specificity to the first antigen may be fused to the second human IgG heavy chain molecule and then, reciprocally, the variable regions having specificity to the second antigen may be fused to the first human IgG heavy chain molecule. In any case, a heteromultimer is formed having binding-specificity for both the first and the second antigens (FIG. 1). In the case of the present invention, the first antibody binding domain may target *P. aeruginosa* flagella type A, while the second antibody binding domain may target *P. aeruginosa* flagella type B.

Alternatively, the dual-specific antibody of the invention may comprise a chimeric antibody specific for *P. aeruginosa* flagella type A fused via a linker peptide to single chain variable fragments (scFv) that specifically bind to flagella type B of *P. aeruginosa* or a "mirror image" antibody that comprise a chimeric antibody specific for *P. aeruginosa* flagella type B fused via a linker peptide to scFvs that specifically bind to flagella type A of *P. aeruginosa* (FIG. 2). The chimeric antibody component of the dual-specific antibody may be replaced with a humanized or human antibody of the same specificity, and the scFv may be humanized to minimize its immunogenicity or it may be derived from a human monoclonal antibody. The scFv component of the dual-specific antibody comprises one $V_H$ and one $V_L$ fragment linked by a spacer peptide such as a glycine-serine linker.

A different kind of dual-specific antibody, often referred to as a "bispecific" antibody, comprises two scFvs having different binding specificities that are interconnected via a linker peptide. In particular, one scFv that specifically binds flagella type A of *P. aeruginosa* is linked via a linker peptide to a scFv that specifically binds flagella type B of *P. aeruginosa*. In principle, a bispecific antibody maybe combined with a chimeric or humanized antibody directed at either flagella of type A or B. Several other formats of dual-specific antibodies, have been disclosed (Kufer et al., 2004) and are all contemplated by the present invention, such as quadroma, an intact antibody wherein each light/heavy chain pair has a different binding specificity, F(ab)$_2$, essentially a Fab fragment of a quadroma, heterodimeric Fab, diabodies and DVD-Ig, in which two variable fragment pairs, each pair specific to a different antigen, are present on each one of the heavy and light chains (see for example US 20090304693).

Thus, in certain embodiments the dual-specific antibody is selected from the group consisting of:
 (i) a dual-specific antibody comprising (a) a scFv that specifically binds to flagella type A, fused to the Fc-region of a first human IgG heavy chain molecule; and (b) a scFv that specifically binds to flagella type B, fused to the Fc-region of a second human IgG heavy chain molecule, wherein a small amino acid residue of the Fc-region of the first human IgG heavy chain molecule is replaced with a large amino acid residue, and a large amino acid residue of the Fc-region of the second human IgG heavy chain molecule is replaced with a small amino acid residue, and/or a large amino acid residue of the Fc-region of the first human IgG heavy chain molecule is replaced with a small amino acid residue, and a small amino acid residue of the Fc-region of the second human IgG heavy chain molecule is replaced with a large amino acid residue, whereby the large amino acid residue forms a protuberance that is positionable in the cavity formed by the small amino acid residue and thereby the first and the second human IgG heavy chain molecules form a heterodimer that specifically binds both flagella type A and flagella type B;
 (ii) a dual-specific antibody comprising an antibody composed of a human IgG constant region fused to variable regions of an anti-*P. aeruginosa* monoclonal antibody that specifically binds to flagella type A, wherein said antibody is connected at its terminal Fc-region to two single chain variable fragments (scFvs) that specifically bind to flagella type B of *P. aeruginosa*.
 (iii) a dual-specific antibody comprising an antibody composed of a human IgG constant region fused to variable regions of an anti-*P. aeruginosa* monoclonal antibody that specifically binds to flagella type B of *P. aeruginosa*, wherein said antibody is connected at its terminal Fc-region to two scFvs that specifically bind to flagella type A of *P. aeruginosa*; and
 (iv) a dual-specific antibody comprising two scFvs that specifically bind to flagella type A of *P. aeruginosa* fused via a linker peptide to two other scFvs that specifically bind to flagella type B of *P. aeruginosa*.

In certain embodiments the antibody is a dual-specific antibody of (i) or (ii).

In one embodiment the antibody is a chimeric antibody comprising a human IgG or IgM constant region fused to mouse variable regions of an anti-*P. aeruginosa* monoclonal antibody that specifically binds to flagella type A or type B of *P. aeruginosa*, and in another embodiment the antibody is a humanized antibody comprising a human IgG or IgM constant region fused to humanized mouse variable regions of an anti-*P. aeruginosa* monoclonal antibody that specifically binds to flagella type A or type B of *P. aeruginosa*. Obviously, the human IgG heavy and light constant domains may be derived from any one of IgG1, IgG2, IgG3, and IgG4 subclasses of human IgG antibodies, and it may comprise one, two or three intact or truncated constant domains ($C_H$1-3), which may optionally be mutated to alter effector function or provide for heteromultimer formation, or modified post-translationally (e.g. glycosylation) to improve the half-life of the antibody. In certain embodiments the IgG constant region is a human IgG1 constant region.

Alternatively, the human constant domains may consist of the human IgM type composed of $C_L$ for the light chain and $C_\mu 1$, $C_\mu 2$, $C_\mu 3$, $C_\mu 4$ for the heavy chain with an adjoining J chain to permit antibody polymerization and formation of a pentameric species. In certain embodiments, the IgM constant region of the antibody of the present invention is a human Igµ and a human Igκ constant region, for example as shown in Example 6 herein below.

As shown below in Examples 1 and 6, and in accordance with the present invention, the genes encoding for the variable regions of the mouse monoclonal antibodies LST-001 and LST-002 and the human monoclonal antibody LST-007 have been cloned and their nucleotide sequences have been determined. The CDR regions present within the variable regions of LST-001 and LST-002 may be identified, for example, by using an algorithm disclosed by Wu and Kabat (1970), hereinafter referred to as "Kabat", or an algorithm known as the IMGT/V-QUEST disclosed by Brochet et al (2008) or according to Chothia (1987; 1992). However, it should be understood that any combination of CDRs and framework regions that confers to the antibody specificity towards *P. aeruginosa* flagellin type A or B or capability to compete with LST-001, LST-002 or LST-007 for binding to *P. aeruginosa* flagellin type A or B is encompassed by the present invention as long as the constant regions are not mouse constant regions.

In certain embodiments the variable regions or scFv that specifically bind to flagella type B comprises (a) a human $V_H$ fragment comprising CDRs present in SEQ ID NO: 1; and (b) a human $V_L$ fragment comprising CDRs present in SEQ ID NO: 2.

In certain embodiments, CDR1, CDR2 and CDR3 of the heavy chain ($V_H$) of LST-007 as defined by IMGT/V-QUEST comprises the amino acid sequence set forth in SEQ ID NO: 3, SEQ ID NO: 4 and SEQ ID NO: 5, respectively, while CDR1, CDR2 and CDR3 of the heavy chain ($V_H$) of LST-007 as defined by Kabat comprises the amino acid sequence set forth in SEQ ID NO: 6, SEQ ID NO: 7 and SEQ ID NO: 8, respectively. The CDR1, CDR2 and CDR3 of the $V_L$ fragment of LST-007 as defined by IMGT/V-QUEST comprises the amino acid sequence set forth in SEQ ID NO: 9, the amino acid sequence AAS and the amino acid sequence set forth in SEQ ID NO: 10, respectively, while CDR1, CDR2 and CDR3 of the $V_L$ fragment as defined by Kabat comprises the amino acid sequence set forth in SEQ ID NO: 11, SEQ ID NO: 12 and SEQ ID NO: 10, respectively (an identical CDR3 was predicted by the two algorithms).

In preferred embodiments, the human $V_H$ fragment comprises the amino acid sequence of SEQ ID NO: 13; and the $V_L$ fragment comprising the amino acid sequence of SEQ ID NO: 14, and in particular the human antibody comprises the $V_H$ fragment fused to a human IgG1 heavy constant domain as set forth in SEQ ID NO: 15 and the $V_L$ fragment fused to a human IgG1 light constant domain as set forth in SEQ ID NO: 16.

In certain embodiments, the antibody comprises the variable region or scFv that specifically binds to flagella type A comprising (a) a mouse $V_H$ fragment comprising CDRs present in SEQ ID NO: 17; and (b) a mouse $V_L$ fragment comprising CDRs present in SEQ ID NO: 18.

In certain embodiments, CDR1, CDR2 and CDR3 of the heavy chain ($V_H$) of LST-001 as defined by IMGT/V-QUEST comprises the amino acid sequence set forth in SEQ ID NO: 19, SEQ ID NO: 20 and SEQ ID NO: 21, respectively, while CDR1, CDR2 and CDR3 of the heavy chain ($V_H$) of LST-001 as defined by Kabat comprises the amino acid sequence set forth in SEQ ID NO: 22, SEQ ID NO: 23 and SEQ ID NO: 24, respectively. The CDR1, CDR2 and CDR3 of the $V_L$ fragment of LST-001 as defined by IMGT/V-QUEST comprises the amino acid sequence set forth in SEQ ID NO: 25, the amino acid sequence WAS and the amino acid sequence set forth in SEQ ID NO: 26, respectively, while CDR1, CDR2 and CDR3 of the $V_L$ fragment as defined by Kabat comprises the amino acid sequence set forth in SEQ ID NO: 27, SEQ ID NO: 28 and SEQ ID NO: 26, respectively (an identical CDR3 was predicted by the two algorithms).

In certain embodiments, the antibody comprises the $V_H$ fragment comprising the amino acid sequence of SEQ ID NO: 17 or SEQ ID NO: 29 and the $V_L$ fragment comprising the amino acid sequence of SEQ ID NO: 18 or SEQ ID NO: 30.

The variable region of the $V_H$ and $V_L$ of LST-002 that is specific to *P. aeruginosa* flagellin type B, comprise amino acid sequences of SEQ ID NO: 31 and SEQ ID NO: 32 or SEQ ID NO: 33, respectively. Two alternative sequences are designated for the $V_L$ of LST-002 because, as shown herein in Example 2, two variant sequences were determined for this fragment; the amino acid sequence of SEQ ID NO: 32 was present in the majority (five out of seven) of the clones sequenced, while the amino acid sequence of SEQ ID NO: 33 was present in the minority (two out of seven) of the clones sequenced.

In certain embodiments, CDR1, CDR2 and CDR3 of the heavy chain ($V_H$) of LST-002 as defined by IMGT/V-QUEST comprises the amino acid sequence set forth in SEQ ID NO: 34, SEQ ID NO: 35 and SEQ ID NO: 36 respectively, while CDR1, CDR2 and CDR3 of the heavy chain ($V_H$) of LST-002 as defined by Kabat comprises the amino acid sequence set forth in SEQ ID NO: 37, SEQ ID NO: 38 and SEQ ID NO: 39 respectively. The CDR1, CDR2, and CDR3 of the majority $V_L$ fragment as defined by IMGT/V-QUEST comprises the amino acid sequence set forth in SEQ ID NO: 40, the amino acid sequence WTS and the amino acid sequence set forth in SEQ ID NO: 41, respectively, while CDR1, CDR2 and CDR3 of the majority $V_L$ fragment as defined by Kabat comprises the amino acid sequence set forth in SEQ ID NO: 42, SEQ ID NO: 43 and SEQ ID NO: 41, respectively (an identical CDR3 was predicted by the two algorithms). The CDR1, CDR2, and CDR3 of the minority $V_L$ fragment as defined by IMGT/V-QUEST and Kabat comprises the amino acid sequence set forth in SEQ ID NO: 44, the amino acid sequence GAS and the amino acid sequence set forth in SEQ ID NO: 45, respectively, while CDR1, CDR2 and CDR3 of the minority $V_L$ fragment as defined by Kabat comprises the amino acid sequence set forth in SEQ ID NO: 46, SEQ ID NO: 47 and SEQ ID NO: 48, respectively.

In certain embodiments, the antibody comprises the $V_H$ fragment comprising the amino acid sequence of SEQ ID NO: 49; and the $V_L$ fragment comprising the amino acid sequence of SEQ ID NO: 50, or the $V_L$ fragment comprising the amino acid sequence of SEQ ID NO: 51.

Consequently, the antibody of the invention may comprise variable regions within framework regions that place the CDR regions in a correct three dimensional position enabling high affinity binding of the specific antigen. In particular, the variable regions as defined by IMGT/V-QUEST or Kabat comprise the CDRs of the LST-001, LST-002 or LST-007 monoclonal antibody within framework regions that place the CDR regions in a correct three dimensional position enabling high affinity binding of P. aeruginosa flagellin type A or type B. As taught by Winter et al., Studnicka and Queen (U.S. Pat. No. 5,693,761), there exist many alternative sets of framework regions that in conjunction with a specific set of CDR regions confer specific binding to an antigen, and anyone of the possible framework regions that will allow specific binding of the antibody of the invention to P. aeruginosa flagellin type A or type B are considered by the invention. Alternatively, the antibody may comprise a variable region comprising the specific CDRs and the specific framework region of the LST-001, LST-002 or LST-007 monoclonal antibodies.

The framework regions may have at least 80%, 85%, 90%, or 95% identity to the framework region comprising the amino acid sequences of the LST-001, LST-002 or LST-007 monoclonal antibodies, and each one of the CDR regions may have at least 80%, 85%, 90%, or 95% identity to the corresponding CDR regions of the LST-001, LST-002 or LST-007 monoclonal antibodies, respectively, as long as the variable region comprising these CDRs and framework regions confers specific binding to P. aeruginosa flagellin type A or type B. In the case of the human antibody LST-007, its framework regions or even CDR's may be modified to remove putative T-cell epitopes, so called de-immunization, while maintaining binding specificity towards flagellin type B.

The antibody of the invention may have variable regions including the CDRs and the interspersing framework regions that are identical to that of LST-001 or LST-002. The resultant chimeric mAbs derived from the LST-001 and LST-002 mAbs are referred to herein as LST-003 and LST-004 respectively.

As described below in Example 2, sequences of humanized antibodies were predicted by using a certain algorithm that compares the murine antibody variable regions with a database of human germline Ig variable regions. In this way, the specificity of the murine antibody to its antigen is maintained in the predicted humanized antibody. It should be understood that any humanized sequences arrived at by using alternative algorithms, for example those described by Yamashita (2007) and Almagro (2008), that still maintain the original antigen binding specificity may be used in the present invention.

The resultant humanized mAbs derived from the LST-001 and LST-002 mAbs have been coined herein LST-005 and LST-006 respectively. In view of the above, in one embodiment, the antibody that specifically binds to flagellin type A, is a humanized or a dual-specific antibody, comprising the $V_H$ fragment consisting of SEQ ID NO: 52 and the $V_L$ fragment consisting of SEQ ID NO: 53. In another embodiment, the antibody that specifically binds to flagellin type B is a humanized or a dual-specific antibody, comprising a $V_H$ fragment consisting of SEQ ID NO: 54 and the $V_L$ fragment consisting of SEQ ID NO: 55 or SEQ ID NO: 56. Each one of the humanized $V_H$ and $V_L$ fragments may have at least 80%, 85%, 90%, or 95% identity to the corresponding $V_H$ and $V_L$ fragments of the LST-001 or LST-002 monoclonal antibodies, respectively, as long as the variable regions comprising these sequences confer specific binding to P. aeruginosa flagellin type A or type B or capability to compete with LST-001 or LST-002 for binding to P. aeruginosa flagellin type A or type B.

In certain embodiments the antibody of the invention is a dual-specific antibody comprising a scFv that specifically binds to flagella type A, fused to the Fc-region of a first human IgG heavy chain molecule; and (b) a scFv that specifically binds to flagella type B, fused to the Fc-region of a second human IgG heavy chain molecule, wherein a small amino acid residue of the CH3 domain of the first human IgG heavy chain molecule is replaced with a large amino acid residue, and a large amino acid residue of the CH3 domain of the second human IgG heavy chain molecule is replaced with a small amino acid residue, and/or a large amino acid residue of the Fc-region of the first human IgG heavy chain molecule is replaced with a small amino acid residue, and a small amino acid residue of the Fc-region of the second human IgG heavy chain molecule is replaced with a large amino acid residue, whereby the large amino acid residue forms a protuberance that is positionable in the cavity formed by the small amino acid residue and thereby the first and the second human IgG heavy chain molecules form a heterodimer that specifically binds both flagella type A and flagella type B, As mentioned above, the variable fragments comprising the scFv of the dual-specific antibody are linked by a peptide termed "spacer peptide", while the peptide used to link the scFv with the constant region of the dual-specific antibody or to link two scFvs in a "bispecific" antibody is termed herein "linker peptide".

Thus, in certain embodiments, each one of the scFvs of the dual-specific antibody is composed of a $V_H$ fragment fused via a spacer peptide to a $V_L$ fragment and the length of the spacer peptide is selected from the range of 5 to 20 amino acid residues or 7 to 15 amino acid residues.

In one embodiment, the spacer peptide of the dual-specific antibody consists of three consecutive peptides of the sequence of SEQ ID NO: 57 (GGGGS) or one peptide having the amino acid sequence of SEQ ID NO: 58 (GGGSAAA).

In certain embodiments, the scFvs are connected via a linker peptide to the C-terminus of the Fc-region of an IgG heavy chain molecule and the length of the linker peptide is selected from the range of 5 to 15 amino acid residues or 9 amino acid residues. In one embodiment, the linker peptide is of the amino acid sequence of SEQ ID NO: 59 (PG-SAGGSGG) or it consists of two or three consecutive peptides of SEQ ID NO: 57.

The "knob" and the "hole" in the dual-specific "knobs-into-holes" type antibody are created by the presence of a "large" amino acid (that has replaced a "small" amino acid of the wild-type sequence) and a "small" amino acid (that has replaced a "large" amino acid of the wild-type sequence), respectively. Gly, Ala, Ser, Pro, Val, Thr, Cys are considered in the art to be small amino acid residues, while Lys, Gln, Glu, Met, Phe, Tyr, Tryp are considered to be large amino acid residues (see for example Livingstone & Barton (1993) Protein sequence alignments: a strategy for the hierarchical analysis of residue conservation. CABIOS 9, 745-756).

In certain embodiments, the small amino acid residue is threonine and the large amino acid residue is tyrosine.

In certain embodiments, the threonine at position 366 (T366) of the CH3 domain of the first human IgG heavy chain molecule is replaced with a tyrosine, and tyrosine at position 407 (Y407) of the CH3 domain of the second human IgG heavy chain molecule is replaced with a threonine; and/or Y407 of the CH3 domain of the first human IgG heavy chain molecule is replaced with a threonine and T366 of the CH3 domain of the second human IgG heavy chain molecule is replaced with a tyrosine.

In certain embodiments, the scFv of the dual-specific antibody that specifically binds to flagella type A comprises a $V_H$ fragment comprising the amino acid sequence of SEQ ID NO: 29 or SEQ ID NO: 17 and the $V_L$ fragment comprising the amino acid sequence of SEQ ID NO: 18 or SEQ ID NO: 30, and the scFv that specifically binds to flagella type B comprises a $V_H$ fragment comprising the amino acid sequence of SEQ ID NO: 31 or SEQ ID NO: 49 and the $V_L$ fragment comprising the amino acid sequence of SEQ ID NO: 50 or SEQ ID NO: 32.

In particular, the dual-specific antibody comprises a first amino acid chain comprising the scFv that specifically binds to flagella type A linked via a linker peptide to a human IgG1 Fc-fragment, said first amino acid chain having the amino acid sequence of SEQ ID NO: 60; and a second amino acid chain comprising the scFv that specifically binds to flagella type B linked via a linker peptide to a human IgG1 Fc-fragment, said second amino acid chain having the amino acid sequence of SEQ ID NO: 61.

In certain embodiments the antibody of the invention is a dual-specific antibody comprising a chimeric antibody composed of a human IgG constant region fused to mouse variable regions of an anti-*P. aeruginosa* monoclonal antibody that specifically binds to flagella type A, wherein said chimeric antibody is connected at its Fc-region to scFvs that specifically bind to flagella type B of *P. aeruginosa*.

Each scFv is composed of a $V_H$ fragment fused via a spacer peptide to a $V_L$ fragment and the length of the spacer peptide is selected from the range of 5 to 20 amino acid residues or 7 to 15 amino acid residues. In particular, the spacer peptide is of the amino acid sequence of SEQ ID NO: 58.

Also, each of the scFvs is connected via a linker peptide to the C-terminus of the Fc-region of an IgG heavy chain molecule and the length of the linker peptide is selected from the range of 5 to 15 amino acid residues or 9 amino acid residues. In particular, the linker peptide consists of two consecutive peptides of the sequence of SEQ ID NO: 57.

In preferred embodiments, the chimeric antibody, that specifically binds to flagella type A of the dual-specific antibody, comprises the $V_H$ fragment comprising SEQ ID NO: 29 and the $V_L$ fragment comprising SEQ ID NO: 30, fused to a human IgG1 Fc-fragment, and each one of said two scFvs comprises the $V_H$ fragment comprising SEQ ID NOs: 31 and the $V_L$ fragment comprising SEQ ID NO: 32.

In particular, the dual-specific antibody comprises an amino acid chain comprising the heavy chain of said chimeric antibody fused to the scFvs, said amino acid chain comprising the amino acid sequence of SEQ ID NO: 62, and the light chain of LST-001 linked to a human IgG1 Fc-fragment.

The invention is also directed to an antibody of the invention or an antigen binding fragment thereof covalently linked, optionally via a cleavable linker, to an antibiotic agent. Non-limiting examples of antibiotic agents are Amikacin, Ampicillin/Sulbactam, Amoxicillin/Calvulanic acid, Aztreonam, Cefepime, Cefotaxime, Ceftazidime, Chloramphenical, Ciprofloxacin, Colistin, Doripenem, Gentamicin, Imipenem, Levofloxacin, Meropenem, Minocycline, Piperacillin, Piperacillin/Tazobactam, Ticracillin, Tigecycline, Tobramycin, Trimethoprim-Sulfamethoxazole.

The invention is further directed to an antibody of the invention or an antigen binding fragment thereof attached to a tag useful for purification and detection, or a chemical moiety that alters the physical properties of the antibody such as stability. Thus, the antibody of the invention may be fused to a tag that enables efficient purification such as, but not limited to, a Histidine-tag or an antigenic peptide tag, and it may be covalently linked to a nonproteinaceous polymer, such as polyethyleneglycol (PEG) to increase the stability of the antibody and change the rate at which the antibody is eliminated from a subject after administration thereto. The PEG is a substituted or unsubstituted polymer having a molecular weight of from about 1000 to about 5000 Da or more. Other non-limiting examples of such polymers are poly (propyleneglycol), or poly (oxyalkylene). An antibody attached to such a tag or chemical moiety is referred to herein as a "derivative" of the unmodified antibody.

Antigen binding fragments of the human, chimeric or humanized antibody of the present invention, or derivatives thereof, wherein said fragment binds flagellin type A or type B of *P. aeruginosa* bacteria are also contemplated by the invention. The antigen-binding fragments can be prepared from full-length antibody isolates, for example, by digestion with proteases, or they may be produced using standard recombinant DNA methodology.

In another aspect, the present invention relates to a nucleic acid molecule comprising nucleotide sequences which encode an antibody according to the present invention or an antigen binding fragment thereof.

In certain embodiments, the nucleic acid molecule encodes a human antibody that specifically binds to flagella type B, comprising the nucleic acid sequence of SEQ ID NO: 63 encoding the heavy chain of said human antibody, and the nucleic acid sequence of SEQ ID NO: 64 encoding the light chain of said human antibody.

In certain embodiments the nucleic acid molecule encodes a dual-specific antibody that specifically binds to flagella type A and B, comprising the nucleic acid sequence of SEQ ID NO: 65 encoding for a scFv that specifically binds to flagella type A fused to a human IgG1 fragment, and the nucleic acid sequence of SEQ ID NO: 66, encoding for a scFv that specifically binds to flagella type B fused to a human IgG1 fragment.

In certain embodiments the nucleic acid molecule encodes a dual-specific antibody that specifically binds to flagella type A and B, comprising the nucleic acid sequence of SEQ ID NO: 67 encoding the heavy chain of a chimeric antibody that specifically bind to flagella type A fused to a scFv that specifically binds to flagella type B, and the nucleic acid sequence of SEQ ID NO: 68 encoding the light chain of an antibody that specifically binds to flagella type A.

In certain embodiments the nucleic acid molecule encodes a chimeric antibody selected from:
  (i) a chimeric antibody that specifically binds to flagella type A, comprising the nucleic acid sequence of SEQ ID NO: 69 encoding the heavy chain of said chimeric antibody, and the nucleic acid sequence of SEQ ID NO: 70 encoding the light chain of said chimeric antibody; or
  (ii) a chimeric antibody that specifically binds to flagella type B, comprising the nucleic acid sequence of SEQ ID NO: 71 encoding the heavy chain of said chimeric antibody, and the nucleic acid sequence of SEQ ID NO: 72 encoding the light chain of said chimeric antibody.

In still another aspect, the present invention relates to a vector comprising the nucleic acid molecule defined hereinbefore, and optionally a nucleotide sequence encoding a heterologous polypeptide such as an antigenic peptide tag or enzyme, operably linked to at least one expression control sequence such as a promoter capable of driving the expression of said nucleic acid molecule.

The present invention further relates to a host cell such as mouse myeloma NS0 and Chinese Hamster Ovary cells (CHO), or plant cells, such as tobacco, carrot and rice cells, which comprises at least one vector as defined hereinbefore and which produces an antibody or antigen binding fragment thereof according to the invention.

In certain embodiments, the human antibody is an IgM antibody that specifically binds to flagella type B, and comprises the VH fragment comprising the amino acid sequence of SEQ ID NO: 13; and the VL fragment comprising the amino acid sequence of SEQ ID NO: 14.

In one aspect, the present invention relates to a pharmaceutical composition comprising at least one antibody or antigen binding fragment thereof, or a derivative of said at least one antibody or antigen binding fragment thereof according to the invention, preferably a human antibody or a dual-specific antibody, and a pharmaceutically acceptable carrier. The term "carrier" refers to a diluent, adjuvant, excipient, or vehicle with which the therapeutic, i.e. the antibody, is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide. The term "derivative" as used herein refers to antibodies modified by addition of molecules such as antibiotic agents, artificial polymers such as PEG, or post-translational modifications such as the attachment of acetate, phosphate, lipids or carbohydrates.

Any patient who is immunosuppressed and/or admitted to the Intensive Care Unit (ICU) could receive an antibody targeting *P. Aeruginosa* flagella prophylactically even in the absence of an underlying *P. Aeruginosa* infection, especially patients who are intubated or catheterized. *P. Aeruginosa* can also cause infections in immunocompetent patients not associated with the ICU setting. Such infections include, but are not limited to, those of the eye (keratitis), and ear infections ("swimmer's ear" or otitis externa).

The flagella of *P. Aeruginosa* aids it in invading the host and disseminating systemically. It has been found in accordance with the present invention that the antibodies disclosed herein are capable of impeding the motility *P. Aeruginosa* by specifically binding to it (see Example 2 hereinafter). This implies that the antibodies of the present invention may be active in creams or gels intended for treatment of topical *P. aeruginosa* infections associated with wounds, eyes, ears, etc.

It has further been found in accordance with the present invention that LST-002 antibodies are efficacious in treating multi-drug resistant *P. Aeruginosa* infections in a pneumonia model in mice (Example 10).

It has further been found in accordance with the present invention that LST-002 antibodies are efficacious in the treatment of multidrug-resistant *P. aeruginosa* model of thigh muscle infection. In Example 10 hereinafter, it is shown that administration of LST-002 antibodies to neutropenic mice totally prevented infection lesions in thigh muscle infected with Ka02, while in saline treated mice the lesions increased 1.8 and 2.7 fold as compared with saline injected muscle, 5 and 7 days after infection, respectively.

Since it is also shown hereinafter in the examples that the chimeric and dual-specific antibodies of the present invention comprising the variable regions of LST-002 indeed binds specifically and with high affinity to flagella type B, and since it is known (U.S. Pat. No. 4,834,976) that the human IgM LST-007 does so too, it can be expected that the human, chimeric, humanized and dual-specific antibodies of the present invention comprising the variable regions of LST-002 or LST-007, or based thereon, would be at least as effective in treating all *P. Aeruginosa* infections harboring the type B flagellin protein Moreover, it is shown hereinafter in the examples that the chimeric and dual-specific antibodies of the present invention comprising the variable regions of LST-001 indeed binds specifically and with high affinity to flagella type A; thus, drawing from the positive experience with LST-002 antibodies, it can be expected that also the chimeric, humanized and dual-specific antibodies of the present invention comprising the variable regions of LST-001, or based thereon, would be at least as effective as LST-002 in treating *P. Aeruginosa* infections harboring the type A flagellin protein.

Interestingly, the dual-specific antibody LST-010 was shown hereinafter in Example 7 to be capable of binding mixed *P. Aeruginosa* populations (flagellin types A and B) at its presumed $K_D$ (1 nM or 0.2 µg/ml), thereby representing a therapeutic target concentration. As mentioned above, LST-002 was capable of treating and preventing *P. Aeruginosa* infections in mice; the therapeutic dose given in Example 10 was on average 35 mg LST-002 antibody per kg body weight. An expected approximate equivalent dose for administration to a human can be calculated using known formulas to be 2.8 mg/kg or 170 mg for a 60 kg adult and 280 mg for a 100 kg adult. Thus, the dose for systemic administration in a human should be in the range of 10 mg to 3000 mg. The frequency of administration is, for example, once a week.

The present invention thus further relates to methods for treatment of an infection caused by *P. aeruginosa*, comprising administering to a subject in need of such treatment a therapeutically effective amount of at least one, i.e. one or more, antibodies according to the present invention or antigen binding fragment thereof. For example, a mixture of two mono-specific antibodies, an anti-*P. aeruginosa* type A flagella antibody and an anti-*P. aeruginosa* type B flagella antibody, or one dual-specific antibody, may be administered to treat a mixed infection of *P. aeruginosa* type A and *P. aeruginosa* type B.

The present invention also relates to prophylactic methods for reduction of a risk of *P. aeruginosa* infection in a subject susceptible to *P. aeruginosa* that may be exposed to *P. aeruginosa*, comprising administering to said patient a therapeutically effective amount of at least one antibody.

Similarly, the present invention further relates to the antibody of the present invention for use in treating an infection caused by *P. aeruginosa*, comprising administering to a subject in need of such treatment a therapeutically effective amount of at least one antibody according to the present invention or antigen binding fragment thereof; and to the antibody of the present invention for use in reducing a risk of *P. aeruginosa* infection in a subject susceptible to *P. aeruginosa* that may be exposed to *P. aeruginosa*, comprising administering to said patient a therapeutically effective amount of at least one antibody.

The term "prophylactic method" is used herein interchangeable with the term "preventive method" and refer to the institution of measures to protect a person from a disease to which he or she has been, or may be, exposed. The preventive or prophylactic action is the prevention of, the delay of, or the interference with, the establishment of a *P. aeruginosa* infection, by administering the antibodies to a susceptible subject that has not an established *P. aeruginosa* infection. The treatment, i.e. the therapeutic action, is the treatment obtained by administering the antibodies to a subject having an established *P. aeruginosa* infection and thus diminishing the number of bacteria or eliminating the bacteria, slowing or stopping the proliferation of the bacteria, slowing or preventing the dissemination of the bacteria, and attenuating or eliminating the symptoms of the infection, in said subject.

Examples of subjects amenable for treatment according to the present invention are subjects suffering from a disease selected from the group consisting of chronic colonization in the lungs, bacteremia, sepsis, surgical wound infection, urinary tract infection, ventilator-associated pneumonia, non-ventilator associated pneumonia, obstructive pulmonary dysfunction (COPD), bronchiectasis, keratitis, and ear infection (otitis externa), and examples of subjects susceptible to infection are immune suppressed subjects selected from the group consisting of cancer patients, patients awaiting transplantation, AIDS patients, burn patients and very low or extremely low birth weight infants (VLBWI and ELBWI, respectively.) VLBWI is defined as a birth weight less than 1500 g, and ELBW is defined as a birth weight less than 1000 g (2 lb, 3 oz). Most extremely low birth weight infants are also the youngest of premature newborns, usually born at 27 weeks' gestational age or younger.

The term "bacteremia" as used herein refers to the presence of bacteria in the blood, and the term "sepsis" refers to a medical condition characterized by a whole-body inflammatory state and the presence of a known or suspected infection in the blood, urine, lungs, skin, or other tissues.

The antibody or antigen binding fragment thereof, or the derivative of said antibody or antigen binding fragment thereof, may be administered by intravenous administration as a bolus or by continuous infusion over a period of time, by intramuscular, intraperitoneal, intracerebrospinal, subcutaneous, intra-articular, intrasynovial, intrathecal, oral, topical, or inhalation routes, and it may be administered in combination with the administration of an antibiotic drug, an antibody that targets *P. aeruginosa* excluding flagellin, such as, but not limited to, anti-LPS or anti-PcrV antibodies (PcrV is one component of the *P. aeruginosa* type III secretion system), or an anti-inflammatory antibody, such as an anti-TNF-α, an anti-IL8 or an anti-IL1 antibody.

The antibodies disclosed herein would be most valuable when used in methods of treatment of multidrug-resistant *P. aeruginosa* that is resistant to at least two drugs, non-limiting examples of which are: strains resistant to an aminoglycoside, such as gentamicin, amikacin, tobramycin; strains resistant to a quinolone such as ciprofloxacin, levofloxacin, moxifloxacin, clinafloxacin, trovafloxacin and sitafloxacin; strains resistant to a cephalosporin, such as ceftazidime, cefepime, cefpirome, cefuroxime, ceftriaxone, cefotaxime and ceftobiprole; strains resistant to a penicillin such as ampicillin—optionally in combination with sulbactam, ureidopenicillin, piperacillin—optionally in combination with tazobactam, and ticarcillin; strains resistant to a carbapenem, such as biapenem, meropenem, imipenem, ertapenem, doripenem, panipenem and faropenem; strains resistant to a polymyxin, such as polymyxin B and colistin; or a monobactam, such as aztreonam, and pandrug-resistant *P. aeruginosa* that is resistant to all classes of available antimicrobial agents.

In still another aspect, the present invention relates to a method for diagnosing and monitoring a host response to *P. aeruginosa* infection, comprising (a) obtaining a patient sample; (b) contacting said patient sample with an antibody of the invention; and (c) measuring binding of said antibody to said patient sample, wherein detection of binding of said antibody to said patient sample indicates the presence or level of multi-drug or pan-drug resistant *P. aeruginosa* in the patient sample. The term "presence" as used herein in the context of the method for diagnosis and monitoring a host response to *P. aeruginosa* infection indicates that the method is a qualitative method giving information only regarding the presence or absence of said bacteria, while the term "level" indicates that the method is a qualitative method producing information regarding the amount or number of cells present in the patient sample. Thus, monitoring is achieved by assessing the level of bacteria over time subsequent to the initiation of administration of the antibodies.

In order to facilitate convenient detection of the antibody, it may be labeled with a detectable label, such as an antigenic peptide tag, fluorophores, enzymes, radioisotopes and micro- and nano-particles. Non-limiting examples of useful fluorophores are fluorescein, rhodamine and alexa; useful enzymes are for example Horse radish peroxidase and alkaline phosphatase; useful radioisotopes are for example $H^3$, $P^{32}$ and $S^{35}$; and particles often used to immobilize antibodies are magnetic or polystyrene micro- and nano-particles.

In yet another aspect, the present invention is directed to a kit for detecting *P. aeruginosa* in a biological sample comprising a container containing an antibody according to the present invention; a container containing a set of reagents required for the detection and quantification of said antibody; and instructions for use.

The invention will now be illustrated by the following non-limitative examples.

EXAMPLES

Example 1

Sequencing the Variable Fragments of the Mouse LST-001 and LST-002 mAbs

The dideoxy termination methodology of polynucleotide sequencing of Sanger et al. (1977) was used to determine the sequences encoding the variable fragments of the heavy and light chains of the mouse LST-001 and LST-002 mAbs, and of the human LST-007. The sequences of the polypeptides are as follows:

(1) mAbs LST-001
    (1a) The full $V_H$ sequence (SEQ ID NO: 29)
    (1b) The mature $V_H$ sequence (SEQ ID NO: 17)
    (1c) The CDR sequences of the $V_H$ sequence as defined by IMGT/V-QUEST:
        CDR1 (LST-001 $V_H$) (SEQ ID NO: 19)
        CDR2 (LST-001 $V_H$) (SEQ ID NO: 20)
        CDR3 (LST-001 $V_H$) (SEQ ID NO: 21)
    (1d) The CDR sequences of the VH sequence as defined by Kabat:
        CDR1 (LST-001 $V_H$) (SEQ ID NO: 22)
        CDR2 (LST-001 VH) (SEQ ID NO: 23)
        CDR3 (LST-001 VH) (SEQ ID NO: 24)
    (1e) The full $V_L$, sequence (SEQ ID NO: 30)
    (1f) The mature $V_L$, sequence. (SEQ ID NO: 18)
    (1g) The CDR sequences of the $V_L$, sequence as defined by IMGT/V-QUEST:
        CDR1 (LST-001 $V_L$) (SEQ ID NO: 25)
        CDR2 (LST-001 $V_L$) (the amino acid sequence WAS)
        CDR3 (LST-001 $V_L$) (SEQ ID NO: 26)
    (1h) The CDR sequences of the $V_L$, sequence as defined by Kabat:
        CDR1 (LST-001 $V_L$) (SEQ ID NO: 27)
        CDR2 (LST-001 $V_L$) (SEQ ID NO: 28)
        CDR3 (LST-001 $V_L$) (SEQ ID NO: 26)
(2) mAbs LST-002
For the $V_L$ of LST-002, two separate yet similar sequences were discovered; one sequence is a consensus sequence from five separate recombinant clones and is termed a "majority sequence"; the other sequence is a consensus sequence from two separate recombinant clones and is termed a "minority sequence".

(2a) The full V_H sequence (SEQ ID NO: 49)
(2b) The mature V_H sequence. (SEQ ID NO: 31)
(2c) The CDR sequences of the V_H sequence as defined by IMGT/V-QUEST:
  CDR1 (LST-002 V_H) (SEQ ID NO: 34)
  CDR2 (LST-002 V_H) (SEQ ID NO: 35)
  CDR3 (LST-002 V_H) (SEQ ID NO: 36)
(2d) The CDR sequences of the V_H sequence as defined by Kabat:
  CDR1 (LST-002 VH) (SEQ ID NO: 37)
  CDR2 (LST-002 VH) (SEQ ID NO: 38)
  CDR3 (LST-002 VH) (SEQ ID NO: 39)
(2e) The full V_L "majority" sequence (SEQ ID NO: 50)
(2f) The mature VL "majority" sequence (SEQ ID NO: 32)
(2g) The CDR sequences of the V_L "majority" sequence as defined by IMGT/V-QUEST
  CDR1 (LST-002 V_{Lmaj}) (SEQ ID NO: 40)
  CDR2 (LST-002 V_{Lmaj}) (the amino acid sequence WTS)
  CDR3 (LST-002 V_{Lmaj}) (SEQ ID NO: 41)
(2h) The CDR sequences of the V_L "majority" sequence as defined by Kabat
  CDR1 (LST-002 V_{Lmaj}) (SEQ ID NO: 42)
  CDR2 (LST-002 V_{Lmaj}) (SEQ ID NO: 43)
  CDR3 (LST-002 V_{Lmaj}) (SEQ ID NO: 41)
(2i) The full V_L "minority" sequence (SEQ ID NO: 51)
(2j) The mature V_L "minority" sequence (SEQ ID NO: 33)
(2k) The CDR sequences of the V_L "minority" sequence as defined by IMGT/V-QUEST
  CDR1 (LST-002 V_{Lmin}) (SEQ ID NO: 44)
  CDR2 (LST-002 V_{Lmin}) (the amino acid sequence GAS)
  CDR3 (LST-002 V_{Lmin}) (SEQ ID NO: 45)
(2l) The CDR sequences of the V_L "minority" sequence as defined by Kabat
  CDR1 (LST-002 V_{Lmin}) (SEQ ID NO: 46)
  CDR2 (LST-002 V_{Lmin}) (SEQ ID NO: 47)
  CDR3 (LST-002 V_{Lmin}) (SEQ ID NO: 48)

Example 2

LST-001 Inhibits Motility of *P. Aeruginosa* Bearing Flagellin Type A but not *P. Aeruginosa* Bearing Flagellin Type B A commercially available, *P. aeruginosa* strain derived from a blood culture (ATCC 27853) was grown overnight at 37° C. in LB media. This strain was shown by us to be a type A flagellin strain and is sensitive to all antibiotics. After overnight culture, bacteria were diluted in fresh LB media to generate an $OD_{600}$ of ~0.2.

To separate wells of 6-well sterile culture plate, a liquefied solution of 3 ml of soft motility agar (0.3%) was added containing LST-001 mAb (0.3-20 µg/ml) or a negative control LST-002 mAb (20 µg/ml). Thereafter, the mAb-impregnated agar was allowed to solidify for 2 hrs at room temperature after which time, 10 µl of bacterial suspension at $OD_{600}$=0.2 was stabbed into the centre of the wells, at a depth of approximately ⅔ into the agar.

Plates were transferred to an incubator at 30° C. for 18-22 hr to allow bacterial growth and swarming (i.e. motility), the latter indicated by the presence of a halo formation encircling the localized bacterial growth. The diameter of the halo formation was measured for each well enabling determination of the inhibitory effect of the mAb of bacterial motility (FIG. 3A). As can be clearly seen, at 20 µg/ml, LST-001 is capable of inhibiting close to 100% of the bacterial swarming.

Figure 3B:
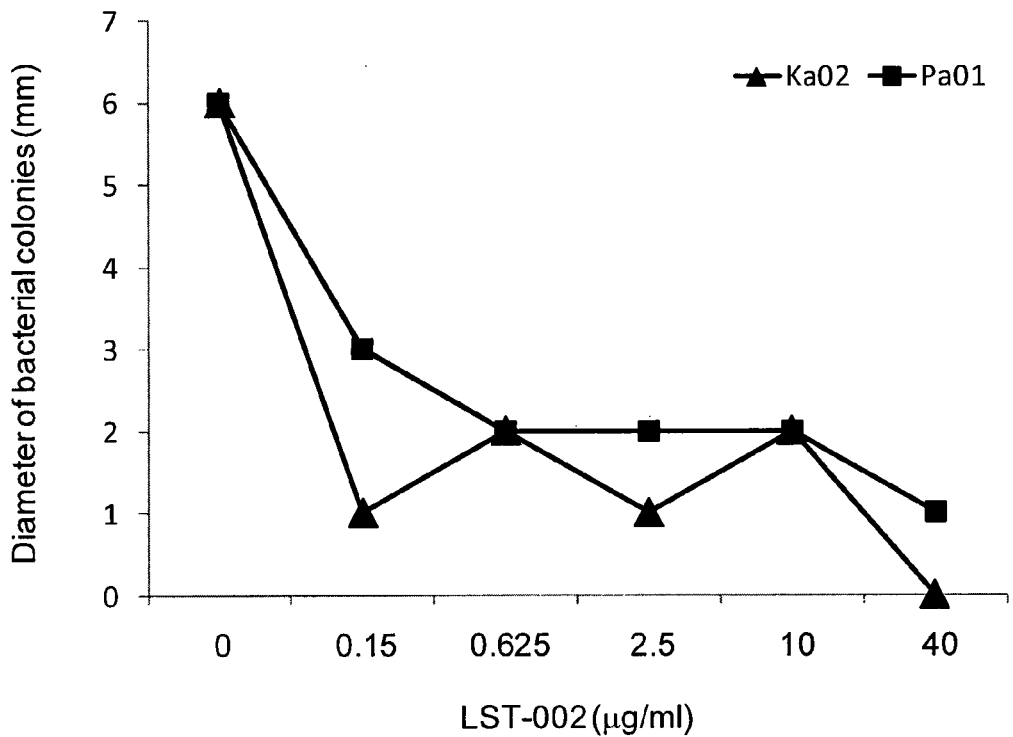

Using an alternative in-vitro motility technology, the effects of LST-002 on motility of a MDR *P. aeruginosa* (PA) strain (Ka02) was performed. In 10 cm plastic culture dishes, a 6 ml underlayer of 0.6% agar in LB was poured and allowed to solidify. During this period, 6 ml of LB was aliquoted into separate tubes to which LST-002 was added at final concentrations 80, 20, 5, 1.25, 0.3 and 0 µg/ml. Thereafter, 10 µA of bacterial culture (containing ~20-100 cfu) was added followed by 6 mls of 0.6% agar in LB. This ~12 ml solution was poured onto the solidified agar under-layer. Following solidification, a final upper layer comprising of 6 mls 0.6% agar in LB was added. Plates were transferred to an incubator at 37° C. for 18-22 hr to allow bacterial growth and swarming (i.e. motility) and the diameter of the bacterial colonies measured. As can be seen from FIG. 3B, using this "sandwich" motility assay, LST-002 caused a significant reduction in the size of bacterial colonies even at very low concentrations for both a laboratory strain (Pa01) and a MDR strain (Ka02).

In preliminary pharmacokinetic studies, we have shown that following a single i.v. injection of LST-002 at 10 mg/kg, early plasma concentrations of this mouse mAb was ~200 µg/ml, significantly higher than those concentrations required to inhibit *P. Aeruginosa* motility in vitro. One may therefore assume that inhibition of motility would be very significant in vivo and a potential major mechanism to attenuate bacterial virulence.

TABLE 1

Ka02 is an example of a multi-drug resistant *P. Aeruginosa* strain (S = antibiotic sensitive; R = antibiotic resistance) with MIC values determined at two separate testing sites using Vitek technology to generate the antibiograms.

| Antibiotics | MIC (mg/ml) site #1 | MIC (mg/ml) site #2 | Vitek | Final |
|---|---|---|---|---|
| Amikacin | 16 | <=2 | S/S | S |
| Ampicillin/Sulbactam | 32 | >=32 | R/R | R |
| Amoxicillin/Calvulanic acid | n/d | 32 | R | R |
| Aztreonam | 32 | n/d | R | R |
| Cefepime | 32 | 32 | R/R | R |
| Cefotaxime | 64 | >=64 | R/R | R |
| Ceftazidime | 8 | >=64 | S/R | S-R |
| Chloramphenicol | 32 | n/d | R | R |
| Ciprofloxacin | 4 | >=4 | R/R | R |
| Colistin | 2 | 2 | S | S |
| Gentamicin | 16 | 4 | R/S | ? |
| Imipenem | n/d | >=16 | R | R |
| Levofloxacin | n/d | >=8 | R | R |
| Meropenem | 16 | >=16 | R/R | R |
| Minocycline | 16 | n/d | R/R | R |
| Piperacillin | 256 | n/d | R | R |
| Piperacillin/Tazobactam | 128 | >=128 | R/R | R |
| Ticarcillin/CA | 256 | n/d | R | R |
| Tigecycline | n/d | >=8 | R | R |
| Tobramycin | 16 | 8 | R/I | R |
| Trimethoprim-Sulfamethoxazole | 320 | >=320 | R/R | R |

Interestingly, prior reports on inhibition of migration of *P. aeruginosa* with anti-flagellar mAbs are done with ex-vivo neutralization of *P. aeruginosa* prior to spotting of "neutralized" *P. aeruginosa* on soft agar. In our hands, it seems that the mAbs retain bioactivity within a soft, yet solidified agar. This implies that the antibodies of the present invention are active in creams or gels intended for treatment of topical *P. aeruginosa* infections associated with wounds, eyes, ears, etc.

Example 3

Production of Chimeric Antibodies LST-003 and LST-004 Derived from the $V_H$ and $V_L$ Domains of their Corresponding Mouse Monoclonal Antibodies LST-001 and LST-002

Chimeric mAb LST-003, contains the LST-001 mouse $V_H$ and $V_L$ domains (SEQ ID NO: 29 and SEQ ID NO: 30, respectively) fused to its respective human IgG1 constant domains. The light chain of this chimeric antibody, consisting of the $V_L$ and $C_L$ domains, is encoded by the nucleic acid molecule having the nucleic acid sequence of SEQ ID NO: 70, and the heavy chain of this chimeric antibody, consisting of the $V_H$ and $C_H$ domains, is encoded by the nucleic acid molecule having the nucleic acid sequence of SEQ ID NO: 69.

In the same way, chimeric mAb LST-004, contains the LST-002 mouse $V_H$ and $V_L$ domains (SEQ ID NO: 49 and SEQ ID NO: 50) fused to a human IgG1 constant backbone. The light chain of this chimeric antibody, consisting of the $V_L$ and $C_L$ domains, is encoded by the nucleic acid molecule having the nucleic acid sequence of SEQ ID NO: 72, and the heavy chain of this chimeric antibody, consisting of the $V_H$ and $C_H$ domains, is encoded by the nucleic acid molecule having the nucleic acid sequence of SEQ ID NO: 71.

Similarly, an additional chimeric mAb can be generated containing the LST-002 mouse $V_H$ domain (SEQ ID NO: 49) and the $V_L$ minority domain (SEQ ID NO: 51) fused to a human IgG1 constant backbone.

To produce LST-003, the LST-001 VL and VH domains were fused directly to their respective human IgG1 constant coding sequences and the resultant VL-CL and VH-CH coding sequences were ligated into one of the 2 available multiple cloning sites (MCS)_present in a bicistronic mammalian expression vector (pVitro-neo-mcs; In-Vivogen). To that end, BglII and NheI restriction motifs sites were included at the 5' and 3'-termini respectively of the VL-CL PCR fragment, which was restricted with BglII/NheI, and thereafter ligated into the identically excised expression plasmid. Similarly, the VH-CH PCR fragment included a 5' BamH1 linker and a 3' AvrII linker. Following excision, the purified PCR fragment was ligated into the expression plasmid previously digested with BamH1 and AvrII. In all instances, the $V_L$-$C_L$ and $V_H$-$C_H$ DNA sequences containing the desired restriction sites for the purpose of cloning, were chemically synthesized using overlapping synthetic primers (GENEART, Regensburg, Germany). This in-vitro "gene-construction" strategy allows optimal codon usage for expression in mammalian cells. Following PCR on the synthetic gene using external primers and sub-cloning into a suitable shuttle vector for acceptance of PCR products (eg. TOPO TA cloning kits, In-Vitrogen), plasmid DNA can be extracted from the host bacterium using conventional plasmid kits. Thereafter, the recombinant plasmids are digested with the appropriate restriction enzymes (BglII/NheI for the $V_L$-$C_L$ fragment and BamH1/AvrII for the $V_H$-$C_H$ fragment) and fragments gel purified for subsequent ligations. Using the current bicistronic plasmid, sequential cloning of the heavy and light chains were performed. To that end, the bicistronic expression plasmid was excised with BglII/NheI followed by ligation of the prepared $V_L$-$C_L$ fragment. Following identification and recovery of appropriate recombinant plasmid by PCR colony screening, this intermediary recombinant plasmid was excised with BamH1/AvrII for acceptance of the $V_H$-$C_H$ fragment. Following identification and recovery of this latter recombinant plasmid, large plasmid preparations were made, followed by extensive bidirectional sequencing covering the inserted antibody fragments across the multiple cloning sites prior to expression studies.

For the chimeric mAb LST-004, the cloning strategies for the $V_L$ and $V_H$ were identical as described for LST-003. Furthermore, the expression plasmid was the same with the exception that the dihydrofolate reductase (DHFR) gene had been cloned into the available EcoRI site (5' GAATTC 3') located 1378 bp down stream from the AvrII site of MCS-1. The purpose was to allow plasmid amplification for eventual generation of stable CHO cell lines containing all the recombinant mAbs.

Figure 4A:
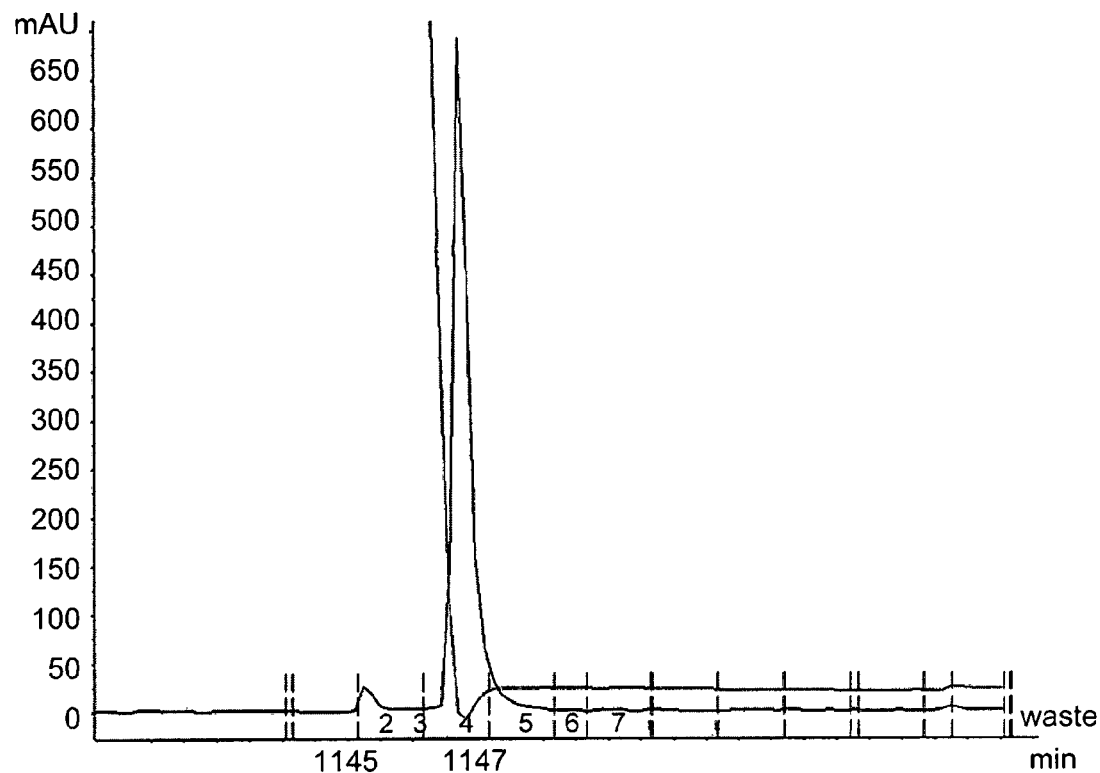
FIGS. 4A-B show a chromatogram (A) with a large absorbance peak (280 nm) representing a purified protein fraction collected from the supernatant of a CHO cell culture containing chimeric LST-003 mAb and a corresponding Coomassie-Blue stained polyacrylamide gel (B) showing the presence of intact chimeric LST-003 heavy and light chain polypeptides in the collected fractions 4-7 as indicated on the X-axis of the chromatogram with the majority of staining in fractions 4 and 5.

The protocol used was as follows: CHO-S cells were cultured in PROCHO4 CDM medium (Lonza). On the day of transfection, the cells were centrifuged at 600 rpm for 5 minutes and resuspended in fresh PROCHO5 CDM medium (Lonza) at a cell density of $2 \times 10^6$ cells/ml. Transfection of 500 ml of culture was performed in a spinner flask using 2.5 μg of DNA and 10 μg Polyethylenimine (PEI) per 1 ml of culture, diluted in 150 mM NaCl. The concentration of plasmid preparation was 1.99 mg/ml ($Abs_{260}/Abs_{280}=1.7$). After 5 hr, the transfected culture was diluted with 500 ml of fresh PROS medium and incubated at 37° C. in 6% $CO_2$ with agitation at 60 rpm. Six days later, cell-free supernatant containing the chimeric mAb was purified on protein-A chromatography (FIG. 4A).

Figure 4B:
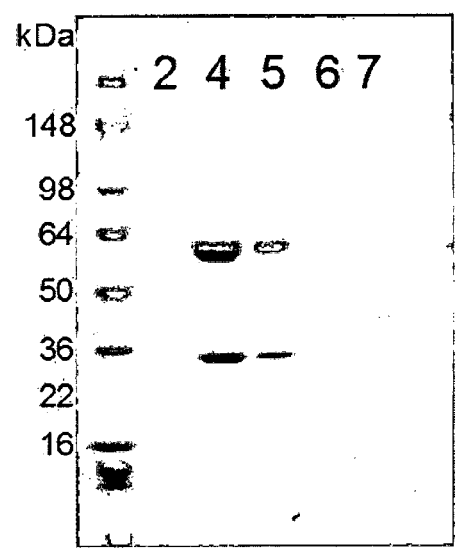

SDS-PAGE analysis following Coomassie gel staining showed that peak fractions collected (2-7) according to the enhanced absorbances contained two major polypeptides of approximately 25 and 55 kD, respectively (primarily in fractions #'s 4 and 5), indicating the presence of intact light and heavy chains thereby representing a bona-fide, recombinantly-expressed chimeric LST-003 antibody (FIG. 4B).

Figure 5A:
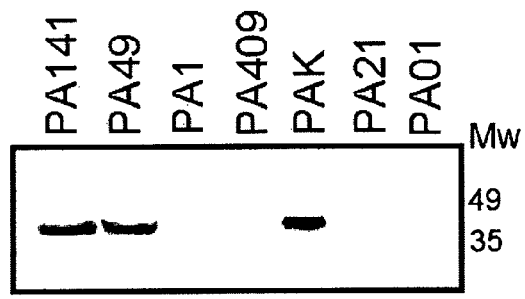
FIGS. 5A-B show two separate immunoblot profiles in which different laboratory or multi-drug resistant (MDR) strains of P. Aeruginosa lysates were screened with either mouse LST-001 mAb (A) or chimeric LST-003 mAb (B) that target P. aeruginosa, flagellin type A. Five bacterial strains (P. aeruginosa 141, 49, 1, 409 and PAK) were shown to be flagellin type A, since immunoreactivity was observed with mouse LST-001 (A) and chimeric LST-003 (B) mAbs. In contrast, 2 bacterial strains (PA21 and PA01), previously known to harbor flagellin type B since they reacted solely with LST-002 mAb, failed to react with either LST-001 or LST-003 mAbs.
Figure 5B:
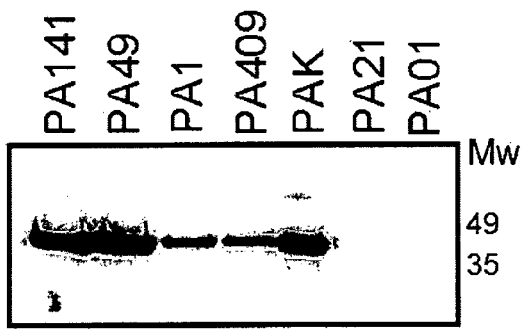
Figure 6:
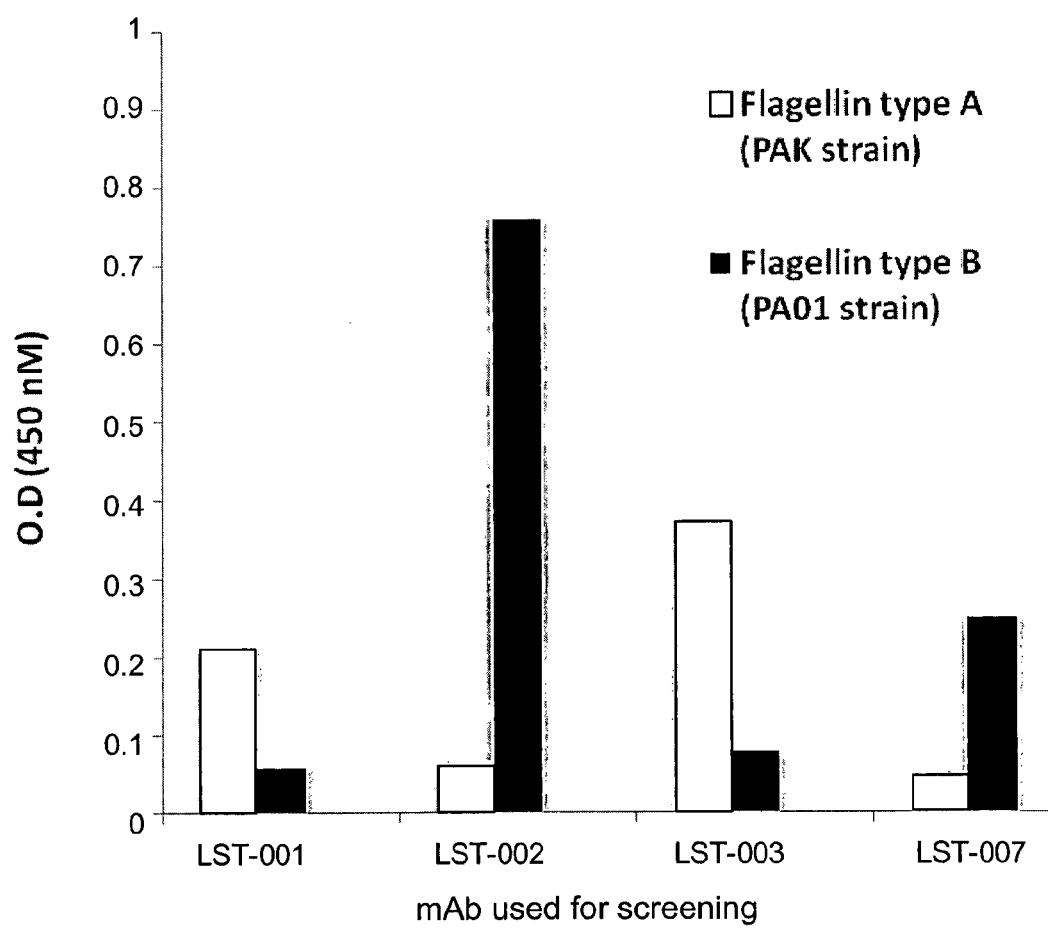
FIG. 6 shows specific, whole P. Aeruginosa bacterial binding, as measured by ELISA, of mouse monoclonal anti-flagella type A and B antibody (LST-001 and LST-002, respectively), chimeric anti-flagella type A antibody (LST-003), and human monoclonal IgM anti-flagella type B antibody (LST-007). Black columns, whole bacterial binding to flagella type B; White columns, whole bacteria binding to flagella type A. OD, Optical Density.

The binding specificity of the chimeric LST-003 mAb was assessed in a western blot experiment as compared to the parental mouse LST-001 mAb. Two identical, yet separate nitrocellulose membranes containing a panel of blotted *P. aeruginosa* lysates of type A or B flagellin following electrophoresis were hybridized with either mouse LST-001 (FIG. 5A) or chimeric LST-003 (FIG. 5B) mAbs at identical final concentrations (10 μg/ml) with the ensuing detecting secondary peroxidase-conjugated antibodies being anti-mouse Fc or anti-human Fc respectively. Laboratory strains PAK (type A flagellin) or PA01 (type B flagellin) were included as appropriate controls whereas other strains represented multi-drug resistant (MDR) *P. aeruginosa* strains. FIG. 5A shows the positive reactivity of mouse LST-001 to strains PA141, PA49, PA1, PA409 and PAK, indicating all 5 strains harbor flagellin type A. The lack of reactivity towards PA21 and PA01 indicates these strains harbor flagellin type B. A very similar profile, yet with stronger binding, was observed with chimeric LST-003 (FIG. 5B) confirming the authenticity of this recombinantly-produced mAb in binding flagellin type A strains (PA141, PA49, PA1, PA409 and PAK) but not flagellin type B (PA21 and PA01). FIG. 6 also depicts binding of LST-001, LST-002 and LST-003 to immobilized, whole *P. aeruginosa* as measured in an ELISA and confirms the western blot findings. See below in Example 7 for the ELISA protocol.

Example 4

Humanized $V_H$ and $V_L$ Sequences Based on LST-001 and LST-002 mAb $V_H$ and $V_L$ Sequences Humanized mAbs termed "LST-005" and "LST-006" that bind *P. Aeruginosa* flagellin type A and B respectively, are designed by predicting humanized $V_H$ and $V_L$ sequences based on LST-001 and LST-002 mAb $V_H$ and $V_L$ sequences using CDR grafting methods. The mouse variable region sequences were compared to databases of human germline 1 g variable region genes (e.g. http://www.ncbi.nlm.nih.gov/igblast/) and the closest human variable heavy and kappa light chain genes that are also frequently expressed in the human repertoire, were selected as the templates for humanization. The CDRs (as defined by Kabat, except for CDRH1 which also includes the preceding five amino acids) of each mouse variable chain were then transferred to the selected human germline frameworks in replacement of the equivalent human sequences. Selected mouse framework residues, that are believed to be important for CDR conformation, were also used to replace their human equivalents, resulting in the CDR grafted humanized antibody sequences. The amino acid sequences are as follows:

(1) LST-005
  (1a) Predicted humanized LST-005 $V_H$ Sequence: (SEQ ID NO: 52)
  (1b) Predicted humanized LST-005 $V_L$ Sequence: (SEQ ID NO: 53)
(2) LST-006
  (2a) Predicted humanized LST-006 VH Sequence: (SEQ ID NO: 54)
  (2b) Predicted humanized LST-006 $V_L$ Sequence ("Majority"): (SEQ ID NO: 55)
  (2c) Predicted humanized LST-006 $V_L$ Sequence ("Minority"): (SEQ ID NO: 56).

Example 5

Production of Humanized Antibodies Corresponding to Monoclonal Antibodies LST-005 (Versus *P. aeruginosa* Type A Flagellin) and LST-006 (Versus *P. aeruginosa* Type B Flagellin)

An artificial gene encoding for humanized LST-005 mAb is made by fusing nucleotide sequences encoding for the LST-005 humanized $V_H$ and $V_L$ domains (SEQ ID NOs: 52 and 53) to a nucleotide sequence encoding for human IgG1 constant backbone. The resulting molecule is cloned downstream to an appropriate promoter and intrinsic signal peptide in an expression vector, and a CHO cell is transfected with said expression vector and produces the humanized antibody.

Humanized LST-006 mAb, containing the LST-006 humanized $V_H$ and $V_L$ (SEQ ID NOs: 54 and 55) domains fused to a human IgG1 constant backbone, is produced in a similar fashion. Additionally, a further humanized mAb subtype containing the LST-006 humanized $V_H$ and $V_L$ (SEQ ID NOs: 54 and 56) domains disclosed above in Example 2 fused to a human IgG1 constant backbone, is produced in a similar fashion.

Example 6

Sequencing the Variable and Constant Fragments of the Human IgM Antibody LST-007 mAb and Linking the Variable Fragments to a Human IgG1 Backbone 6.1. LST-007 Sequences
  (6a) The full $V_H$ sequence (SEQ ID NO: 13)
  (6b) The mature $V_H$ sequence. (SEQ ID NO: 1)
  (6c) The CDR sequences of the $V_H$ sequence as defined by IMGT/V-QUEST:
    CDR1 (LST-007 $V_H$) (SEQ ID NO: 3)
    CDR2 (LST-007 $V_H$) (SEQ ID NO: 4)
    CDR3 (LST-007 $V_H$) (SEQ ID NO: 5)
  (6d) The CDR sequences of the $V_H$ sequence as defined by Kabat:
    CDR1 (LST-007 $V_H$) (SEQ ID NO: 6)
    CDR2 (LST-007 VH) (SEQ ID NO: 7)
    CDR3 (LST-007 VH) (SEQ ID NO: 8)
  (6e) The full $V_L$ sequence (SEQ ID NO: 14)
  (6f) The mature $V_L$ sequence. (SEQ ID NO: 2)
  (6g) The CDR sequences of the $V_L$ sequence as defined by IMGT/V-QUEST:
    CDR1 (LST-001 $V_L$) (SEQ ID NO: 9)
    CDR2 (LST-001 $V_L$) (the amino acid sequence AAS)
    CDR3 (LST-001 $V_L$) (SEQ ID NO: 10)
  (6h) The CDR sequences of the $V_L$ sequence as defined by Kabat:
    CDR1 (LST-001 $V_L$) (SEQ ID NO: 11)
    CDR2 (LST-001 $V_L$) (SEQ ID NO: 12)
    CDR3 (LST-001 $V_L$) (SEQ ID NO: 10)

6.2 Binding of Human IgM Antibody LST-007 to Intact, Immobilized *P. Aeruginosa* Bacterium.

*P. aeruginosa* laboratory strains PAK (flagellin type A) and Pa01 (flagellin type B) were grown overnight, diluted to an OD of 0.3 and washed with PBS. Fifty μl bacteria were then plated onto ELISA plates pre-coated with 50 μl poly-L-lysine (1 μg/ml in PBS) which were blocked with PBS-10% fetal calf serum (FCS). Following overnight incubation with bacteria at 4° C., plates were washed with 0.9% saline-0.05% Tween-20 and incubated with 1:2 dilutions of LST-001, LST-002, LST-007 supernatant or purified LST-003 (~2 μg/ml) for 2 hrs at room temperature. Following washing, secondary goat anti-mouse (LST-001, LST-002) or goat anti-human detecting antibodies (LST-003, LST-007) were added and coloration generated following the addition of TMB substrate and plates read for absorbance (405 nm) following addition of 10% $H_2SO_4$.

Figure 9:
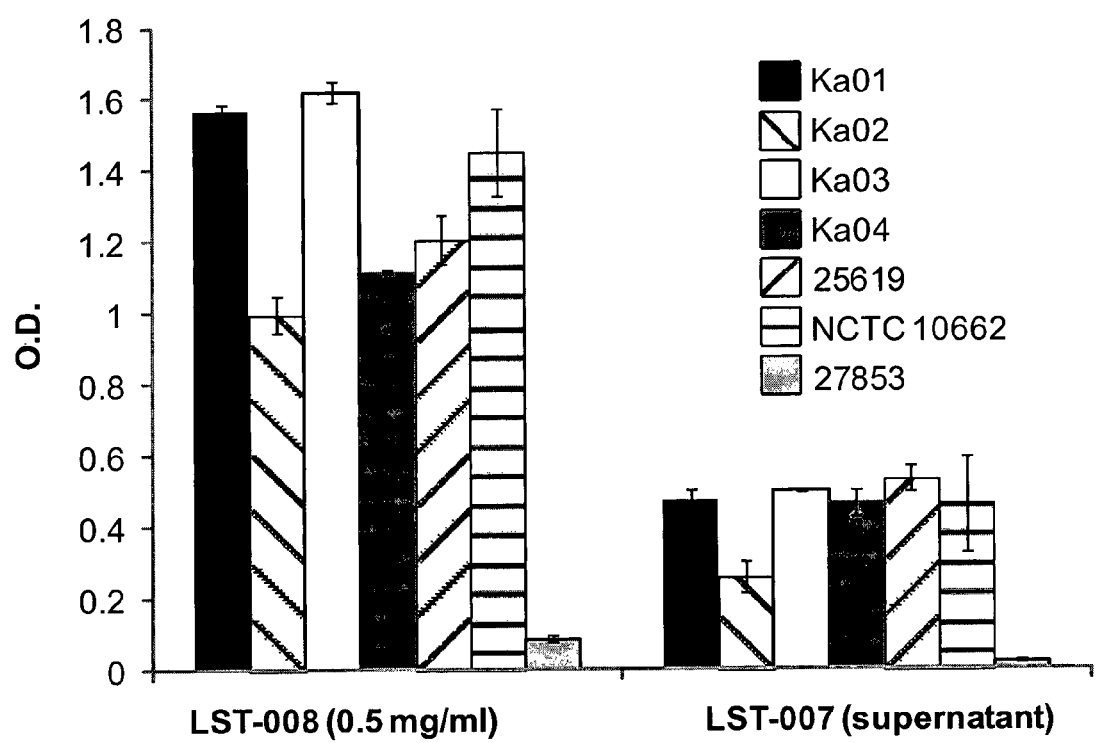
FIG. 9 shows binding of human mAbs LST-007 and LST-008 targeting P. aeruginosa flagellin type B. Ka01, Ka02, Ka03 and Ka04—clinical P. Aeruginosa isolates of which Ka02 and Ka04 are multi-drug or partial drug resistant; 25619, NCTC10662, 27853-commercial PA strains.

As can be seen in FIG. 6 and FIG. 9, LST-007 specifically binds to all seven *P. Aeruginosa* bacteria strains tested (one in FIGS. 6 and 6 in FIG. 9) harboring flagellin type B, but not flagellin type A (FIG. 9, strain 27853). This confirms that following its secretion, LST-007 is present in supernatants as an intact mAb that is in a conformationally correct state.

6.3 Cloning and Expression of the Human Antibody LST-007.

Cloning of the $V_H$ and $V_L$ domains of LST-007 was performed by PCR. Briefly, total RNA was extracted from cells previously confirmed to secrete the human antibody. Thereafter, cDNA was created from the RNA by reverse transcription with an oligo(dT) primer. PCR was performed using a mixture of IgM designed, degenerate primers; the forward primer annealing to the signal/leader peptide; and the reverse primer annealing to the beginning of the first constant domain.

LST-007 is currently produced in Epstein-Barr virus (EBV) transformed human B-lymphocytes, termed lymphoblastoid cell line (LCL). LCL's suffer from a number of drawbacks, such as they grow extremely slowly and as aggregates, fail to reach cell confluency, are low level antibody producing cells, require high concentrations of fetal bovine serum (15%) to support growth, might contain residual virus (eg. EBV) and problematic to adapt to serum-free media to expedite purification. Therefore, it is highly desirable to produce true immortalized cell lines, either by fusing the transformed B-cells with myeloma cells, for example derivatives of P3X63 such as P3X63Ag8.653 (ATCC; cat # CRL-1580) or SP2/0 (ATCC; cat #CRL-1646), or with heteromyeloma cells such as F3B6 (ATCC; cat #HB-8785).

Another attractive possibility is to express the antibody in a eukaryotic cell that is easily handled and which produce large amounts of antibody. Thus, the nucleic acid sequences encoding for the heavy and light chains are cloned into a vector optionally in conjunction with nucleic acid sequences encoding for the J-chain. Thus, the human antibody may be expressed in a cell, such as CHO cells, either as IgG or IgM type, depending on the type of heavy chain and on the presence or absence of the J-chain.

The IgM type confers certain advantages such as avidity towards the flagella target where it has been purported to adopt a profound conformational change to create a "staple" position in which the IgM appears as 10-legged spiders attached to the surface of the flagella (Roax, 1999). Additionally, IgM molecules fix complement, promote opsonophagocytosis of bacteria, are resistant to proteolytic digestion by P. Aeruginosa elastase and might be administered at lower doses to produce desired therapeutic effects.

6.4. Cloning of LST-008 Comprising $V_H$ and $V_L$ of Human Monoclonal Antibody LST-007 Linked to hIgG1.

To generate a fully human recombinant LST-008 equipped with a human IgG1 domain, DNA encoding the $V_H$ domain of LST-007 (SEQ ID NO: 13) together with its respective heavy constant human IgG1 domain were synthesized and subcloned into a mammalian expression plasmid so that the entire coding sequence was ligated into the available AvrII/BamHI sites (see) as detailed above in Example 3 regarding the chimeric mAb LST-004. The heavy chain of this human monoclonal antibody, consisting of the $V_H$ and $C_H$ domains, is encoded by the nucleic acid molecule having the nucleic acid sequence of SEQ ID NO: 63.

The entire amino acid sequence of the heavy chain sequence is set forth in SEQ ID NO: 15.

Figure 11:
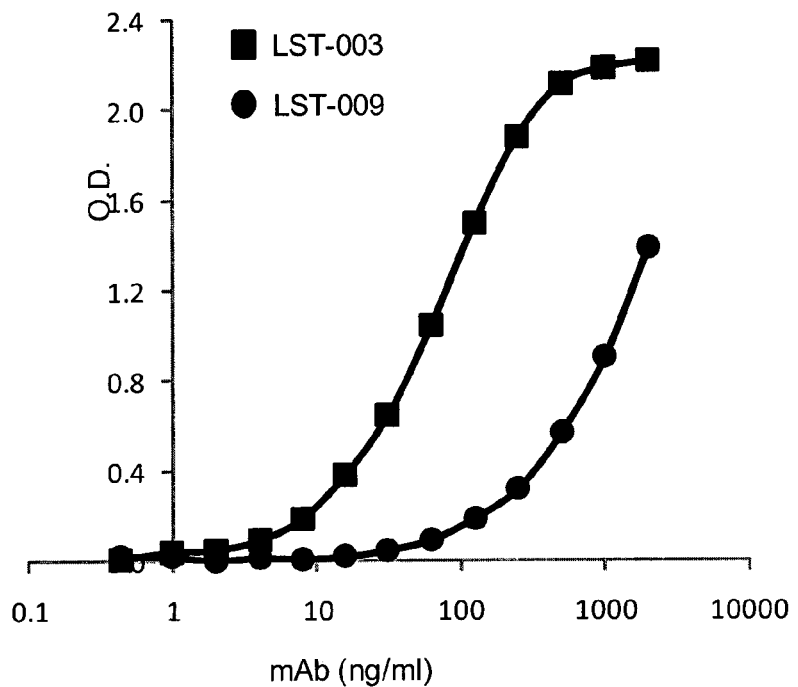
FIG. 11 shows binding of the monoclonal dual-specific anti-flagella type A and B antibody LST-009 to recombinantly expressed flagellin type A, by an ELISA assay; OD, Optical Density. The binding profile of LST-009 towards PA flagellin type A is directly compared with the chimeric mAb LST-003.

In a similar mode, $V_L$ domain of LST-007 (SEQ ID NO: 14) together with its respective light constant domain of human IgG1 were synthesized and subcloned into a mammalian expression plasmid so that the entire coding sequence was ligated into the available BglII/NdeI sites (see FIG. 11). The entire amino acid sequence of the light chain sequence is set forth in (SEQ ID NO: 16).

The light chain of this human monoclonal antibody, consisting of the $V_L$ and $C_L$ domains, is encoded by the nucleic acid molecule having the nucleic acid sequence of SEQ ID NO: 64.

Figure 7A:
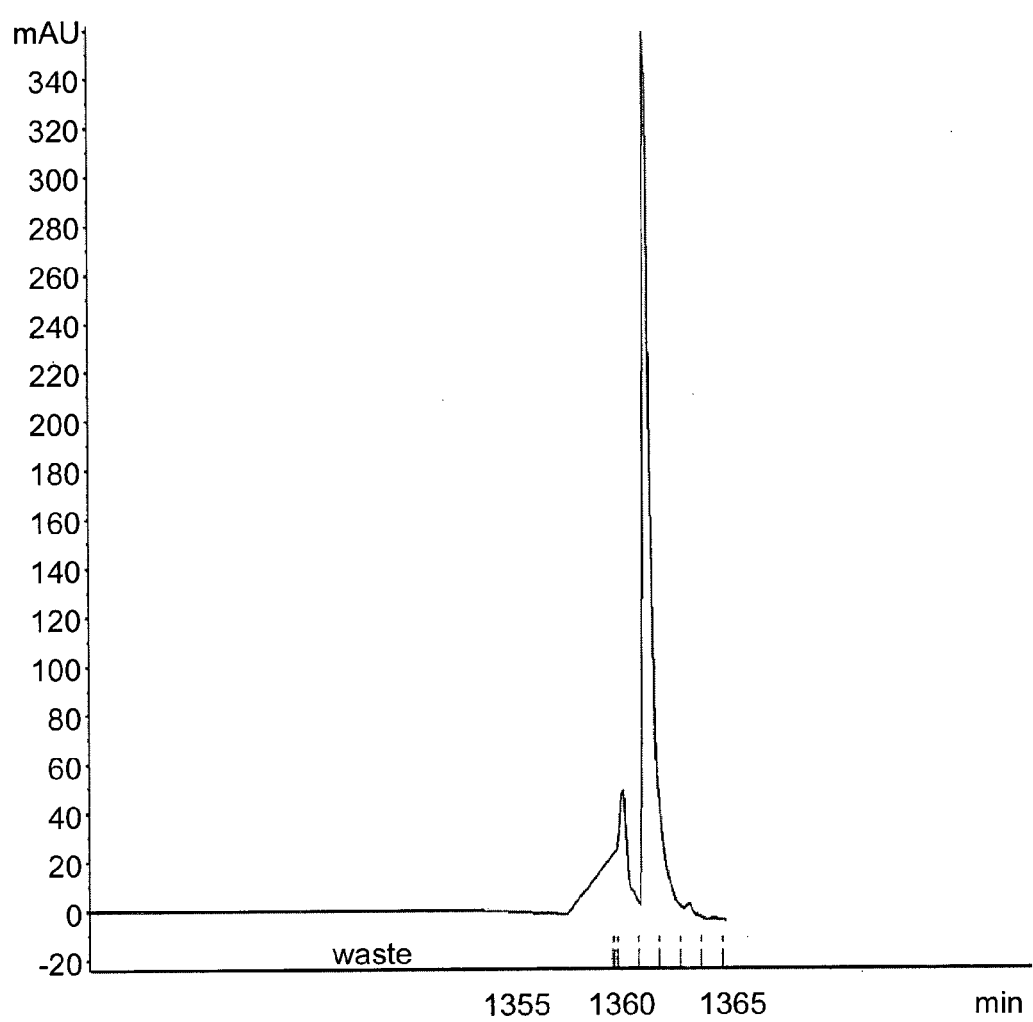
FIGS. 7A-B show the purification profile of recombinant human LST-008 transiently expressed in CHO. A chromatogram of the purification profile is depicted (A) and the peak fraction containing LST-008 was stained with Coomassie following SDS-PAGE (B; lane 2; lane 1=marker proteins).
Figure 7B:
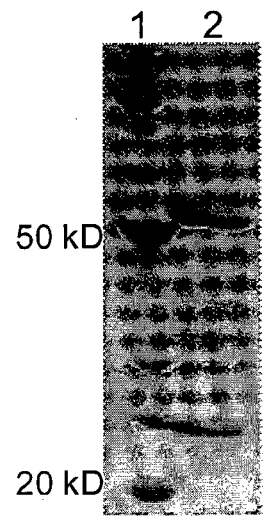

The bicistronic plasmid harboring the $V_H$ and $V_L$ of LST-007 (SEQ ID NO: 13 and SEQ ID NO: 14, respectively) and fused to its respective human IgG1 constant domains, was transiently transfected into CHO cells. The protocol used was as follows: CHO-S cells were cultured in PROCHO4 CDM medium (Lonza). On the day of transfection, the cells were centrifuged at 600 rpm for 5 minutes and resuspended in fresh PROCHO5 CDM medium (Lonza) at a cell density of $2\times10^6$ cells/ml. Transfection of 500 ml of culture was performed in a spinner flask using 2.5 µg of DNA and 10 µg Polyethylenimine (PEI) per 1 ml of culture, diluted in 150 mM NaCl. The concentration of plasmid preparation was 1.99 mg/ml ($Abs_{260}/Abs_{280}=1.7$). After 5 hr, the transfected culture was diluted with 500 ml of fresh PROS medium and incubated at 37° C. in 6% $CO_2$ with agitation at 60 rpm. Six days later, cell-free supernatant containing the fully human mAb was purified on protein-A chromatography (FIG. 7) with the purified peak on Coomassie gel staining depicting the $V_H$ and $V_L$ fragments at approximately 55 and 25 kD respectively (FIG. 7, inset, lane 2) according to the protein markers in FIG. 7, inset, lane 1.

Figure 8:
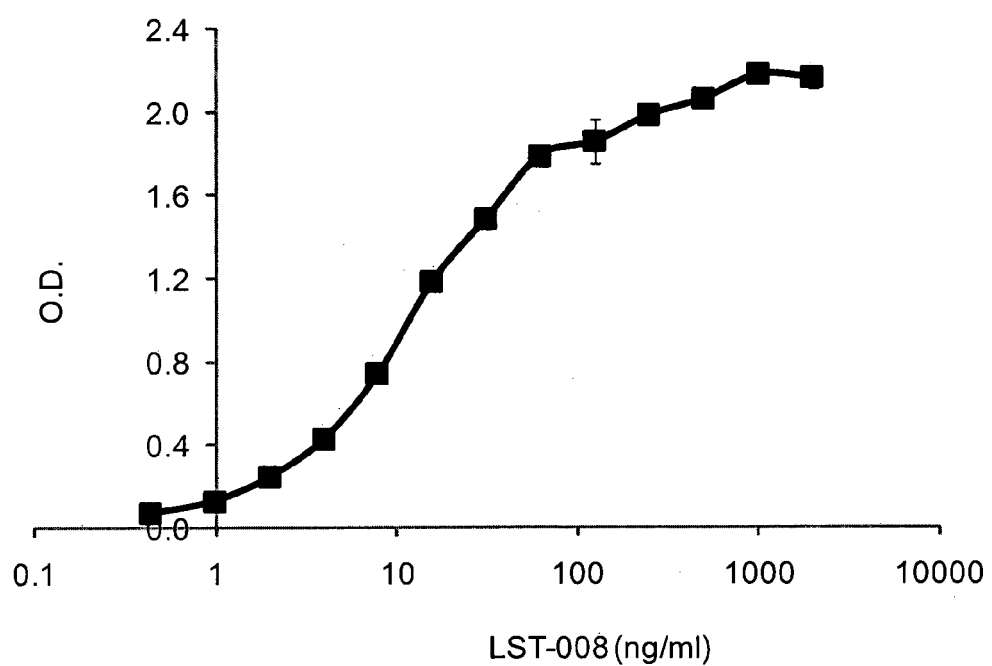
FIG. 8 shows the binding profile of LST-008 on ELISA plates coated with recombinant PA flagellin type B.

To confirm authenticity of recombinantly-produced LST-008, its reactivity to P. Aeruginosa flagellin type B by ELISA was determined (FIG. 8). Maxisorp ELISA plates were coated with recombinant flagellin type B at 5 µg/ml (250 ng/well), blocked with PBS-10% FCS and incubated with LST-008 over a concentration range of 0.43 ng/ml-2 µg/ml. Thereafter, wells were washed and replenished with a goat-anti-human Fc-HRP conjugated secondary antibody at 1:10,000 dilution. Reaction was catalyzed by the addition of TMB substrate and plates read for absorbance (405 nm) following addition of 10% $H_2SO_4$. A sigmoidal concentration-response curve was obtained with $EC_{50}$~10 ng/ml. Additionally, in a bacterial binding assay employing a panel of P. Aeruginosa strains fixed by formaldehyde to ELISA plates (FIG. 9), LST-008 (0.5 µg/ml final concentration) bound all strains known to harbor flagellin type B (Ka01, Ka02, Ka03, Ka04, 25619, NCTC 10662) but not flagellin type A (27853). LST-008's binding profile was identical to that observed with its parental hybridoma LST-007, from which its $V_H$ and $V_L$ regions were derived (FIG. 9).

Example 7

Production of Dual-Specific Antibodies Specifically Binding Flagellin, Type A and Type B of P. aeruginosa 7.1 Strategy and Cloning of Dual-Specific Antibodies.

A most attractive design is the so called "knobs-into-holes" concept in which a knob is created by replacing a small amino side chain at the interface between CH3 domains of the human IgG1 Fc region (hinge, constant region 2 and 3 of immunoglobulin heavy chain (CH2 and CH3), GenBank accession no. AF150959) with a larger one, whereas a hole is constructed by replacing a large side chain with a smaller one.

In particular, a knob variant is obtained by replacement of a small amino acid (threonine at position 366) with a large amino acid (tyrosine) in the CH3 domain of the human IgG1 Fc region, creating the mutant T366Y. A hole variant is constructed by replacement of a large residue (tyrosine at position 407) with a small one (threonine) in the CH3 domain (Ridgway et al., 1996), creating the mutant Y407T. Anti-P. aeruginosa flagellin type A and anti-P. aeruginosa flagellin type B scFvs are fused to the knob and hole variants, respectively (FIG. 1). The two chains are then produced in CHO cells and heterodimer antibodies with dual specificity are produced.

The dual-specific antibody LST-009 was produced according to the above strategy, as follows: the LST-001 anti-flagella type A antibody $V_H$ and $V_L$ regions were fused as a scFv to the constant region of IgG1 (Hinge-CH2-CH3). Optimized codon usage for expression in mammalian cells was designed in which the $V_H$ of LST-001 was the most upstream sequence translated preceded by its own signal peptide. At $V_H$'s C'-terminus, a coding sequence conforming to an amino acid spacer peptide, GGGGSGGGGSGGGGS (SEQ ID NO: 57 repeated three times), was placed followed immediately by the mature coding sequence of $V_L$ of LST-001. At the end of $V_L$, a linker peptide DNA sequence conforming to amino acids PGSAGGSGG (SEQ ID NO: 59) was placed followed by a human IgG1 sequence constituting the hinge, CH2 and CH3 domains. At amino acid #366, the wild-type small threonine (T) residue was replaced by a large tyrosine (Y) residue. This substitution created a "knob" variant within the CH3 domain. The entire amino acid sequence is set forth in SEQ ID NO: 60.

The nucleic acid molecule encoding for the sequence of SEQ ID NO: 60, which has the nucleic acid sequence as set forth in SEQ ID NO: 65, was subcloned into pVitro-neo-MCS (equipped with the DHFR gene) via BamH1-AvrII restriction sites at the MCS-1 as detailed above in Example 3 regarding the chimeric mAb LST-004.

Similarly, LST-002 $V_L$ and $V_H$ were cloned as an scFv with human IgG1 Fc (Hinge-CH2-CH3). The format is $V_L$ majority-linker-$V_H$-linker-CH2-CH3. Optimized codon usage for expression in mammalian cells was designed in which the $V_L$ majority of LST-002 was the most upstream sequence translated preceded by its own signal peptide. At $V_L$'s C'-terminus, a coding sequence conforming to an amino acid spacer linker, GGGSAAA (SEQ ID NO: 58), was placed followed immediately by the mature coding sequence of $V_H$ of LST-002. At the end of $V_L$, a linker peptide DNA sequence conforming to amino acids PGSAGGSGG (SEQ ID NO: 59) was placed followed by a human IgG1 sequence constituting the hinge, CH2 and CH3 domains. At amino acid #407, the wild-type and large tyrosine (Y) residue was replaced by a small threonine (T) residue. This substitution created a "hole" variant within the CH3 domain. The entire amino acid sequence is set forth in SEQ ID NO: 61.

The nucleic acid molecule encoding for the sequence of SEQ ID NO: 61, which has the nucleic acid sequence as set forth in SEQ ID NO: 66, was subcloned into pVitro-neo-MCS (equipped with the DHFR gene) via BglII-NheI restriction sites at the MCS2.

Additionally, a proline has been included in the linker peptide since this is known to disrupt alpha helices and augment folding/heterodimerization. It should also be noted that the signal peptide of the $V_H$ domain is used in the anti-flagella type A scFv, whereas the signal peptide of the $V_L$ domain is used in the anti-flagella type B scFv. This is important, because the presence of a $V_L$ signal peptide is crucial for antibody secretion.

The constructs were cloned into the multi cloning sites of a pVITRO-neo-mcs vector (equipped with the DHFR gene). This vector represents an example of a commercially available multigenic plasmid which can be selectable in *E. Coli* via kanamycin or selectable in mammalian cells with G418. By incorporation of the dihydrofolate reductase (DHFR) gene into the plasmid and transfection into mammalian cells (eg. CHO), addition of methotrexate will cause gene amplification of DHFR with its associated transfected DNA. This results in multiple copies of the recombinant plasmid in the transfected, stable cell and higher levels of the recombinant protein.

7.2 Transient Transfection of CHO Cells with DNA Encoding for Dual-Specific Antibody LST-009.

Suspension culture adapted CHO cells were cultured in PROCHO4 CDM medium (Lonza). On the day of the transfection, the cells were centrifuged at 200 g for 5 min and resuspended in fresh PROCHO5 CDM or Ultra CHO medium (Lonza) at a cell density of $2 \times 10^6$ cells/ml. CHO cell cultures were then transfected with 2.5 μg of LST-009 DNA and 10-15 μg polyethylenimine (PEI) per 1 ml of culture, diluted in 150 mM NaCl using a plasmid preparation with a Abs260/Abs280>1.7) in spinner flasks agitated at 60 rpm 37° C. in 8% CO2. After 5 hr, the transfected culture was diluted with an equal culture volume of fresh PROCHO5 or Ultra CHO medium and incubated at 37° C. in 8% CO2 with agitation at 60 rpm. The supernatant was collected after 9-14 days post-transfection.

7.3. Purification of LST-009 and Analysis of Purified mAb.

Figure 10A:
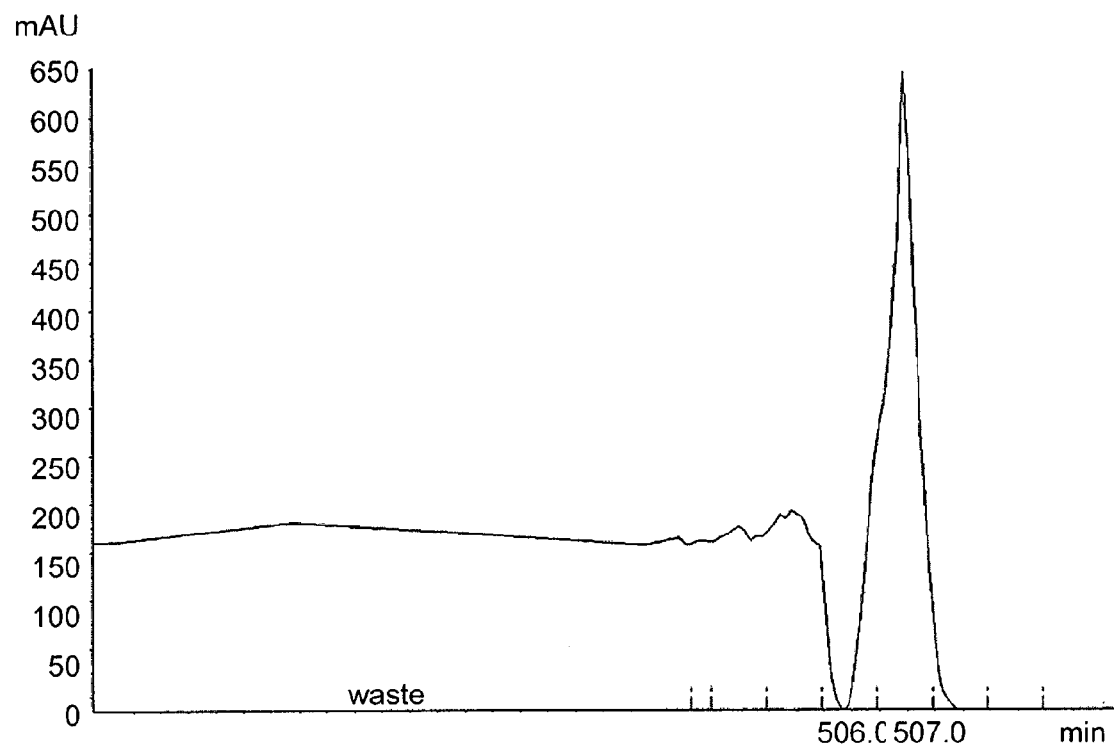
FIGS. 10A-C show details of the chromatographic purification of the monoclonal dual-specific anti-flagella type A and B antibody LST-009 (A) and the corresponding Coomassie-gel stained analysis of the purified protein without (B) or with (C) reducing agent (dithiothreitol, DTT).
Figure 10:
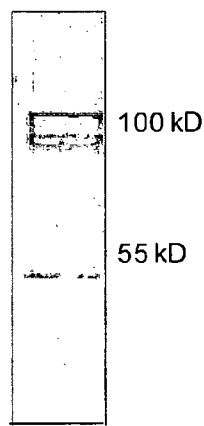
Figure 10:
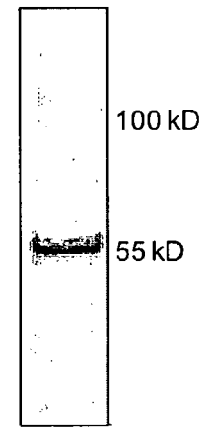

Supernatant was purified using an Amersham Biosciences AKTA Chromatography system. Purification method was performed using 1 ml Protein A columns (GE Healthcare) using a standard antibody purification protocol. A typical purification chromatogram trace of heterodimeric LST-009 mAb is shown in FIG. 10.

Figure 16:
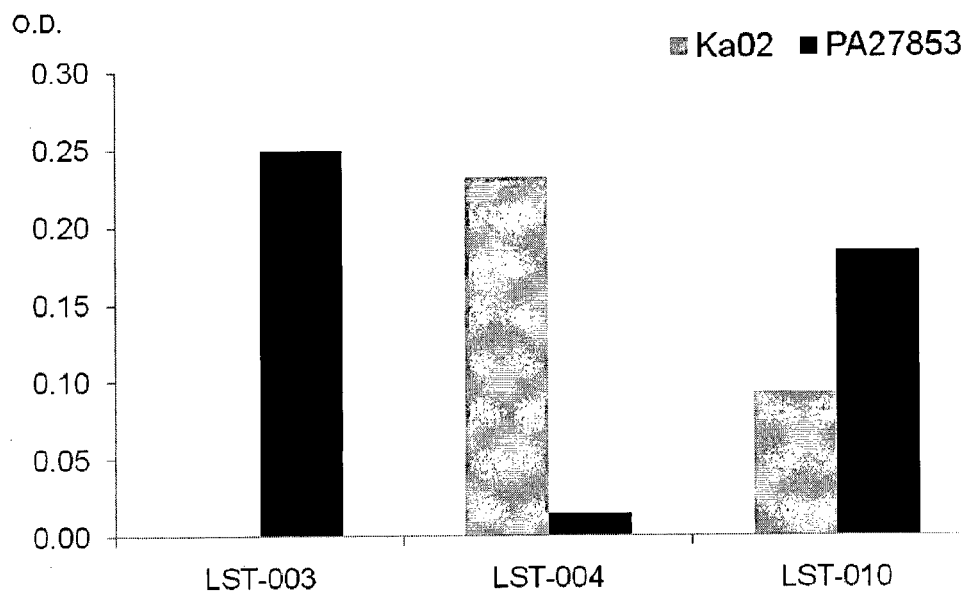
FIG. 16 shows binding properties of dual-specific mAb LST-010 (1 nM) towards PA bacteria containing flagellin type A (PA27853) or type B (Ka02). OD, Optical Density.

After successful elution of bound protein from the column, fractions were collected that corresponded to elution peak. Bradford analysis was performed to determine which fractions contained suitable levels of protein for dialysis. Fractions containing protein were dialysed overnight at 4° C. in PBS pH7.2 at a ratio of 1:100. Purified fractions were collected and analysed by SDS-PAGE and Coomassie gel staining to determine purity (see FIG. 16, inset).

Yields of purified LST-009 were ~4 mg/l. On Coomassie gel staining in the presence of reducing agent (50 mM DTT final concentration), LST-009 was stained as ~50-55 kD band (FIG. 10, lane B). This conforms to the anticipated $M_w$ derived from a scFv fragment and the presence of CH2-CH3 of the human IgG1 heavy chain. The apparent single band consists of the scFv for *P. aeruginosa* flagellin type A (with associated heavy chains) and the scFv for *P. aeruginosa* flagellin type B (with associated heavy chains). In the absence of reducing agent (FIG. 10, inset lane A), a doublet was observed between ~90-100 kD.

7.4. Binding of Dual Specific LST-009 to ELISA Plates Coated with Recombinantly-Expressed *P. aeruginosa* Flagellin Types A or B.

Two hundred and fifty ng (250 ng) of *P. aeruginosa* flagellin type A or B (50 μl from 5 μg/ml) were dispensed into each well of ELISA plates (Nunc, cat #442404) and coating allowed to proceed for 2 hours at room temperature with gentle shaking. Plates were then blocked with 200 μl PBS-10% fetal bovine serum (FBS) overnight at 4° C.

LST-009 diluted in PBS-10% FBS was added to wells over a concentration range of 0.43 μg/ml-2 μg/ml and incubation allowed to proceed for 2 hrs at room temperature. As suitable control mAbs for LST-009 and in order to guage binding potency, LST-003 and LST-004 were included in the ELISA since these mAbs harbored the same $V_H$ and $V_L$ of LST-009 with all 3 mAbs being detected with the same anti-human Fc secondary antibody. To that end, following three washes with PBS-0.05% Tween-20, 50 μl of a goat anti-human IgG (Fc)-HRP (Cat # A80-104P; Bethyl, Tex., USA) was added at a dilution of 1:10,000 in PBS-10% FBS with incubation allowed to proceed for 60 min at room temperature. Following 3 separate washes with PBS-Tween-20 (0.05%) and gentle tapping of plates on paper towels to remove final traces of wash buffer, 50 μl TMB/E substrate solution (Cat #ES001-500 ml; Millipore) was added for 15 min at room temperature. Thereafter, signal was quenched with 50 μl 10% $H_2SO_4$ and plates read at 450 nm in a Microtiter plate reader (Anthos MultiRead 400).

Figure 12:
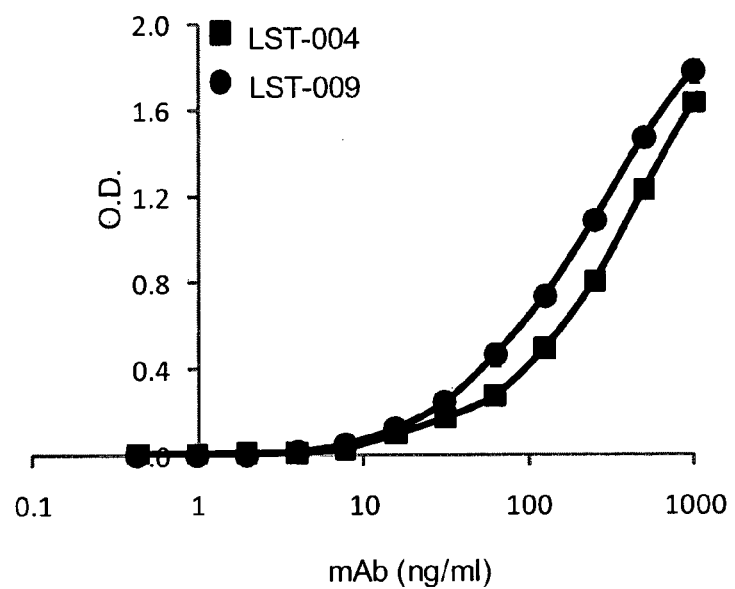
FIG. 12 shows binding of the monoclonal dual-specific anti-flagella type A and B antibody LST-009 to recombinantly expressed flagellin type B, by an ELISA assay; OD, Optical Density. The binding profile of LST-009 towards PA flagellin type B is directly compared with the chimeric mAb LST-004.
Figure 17:
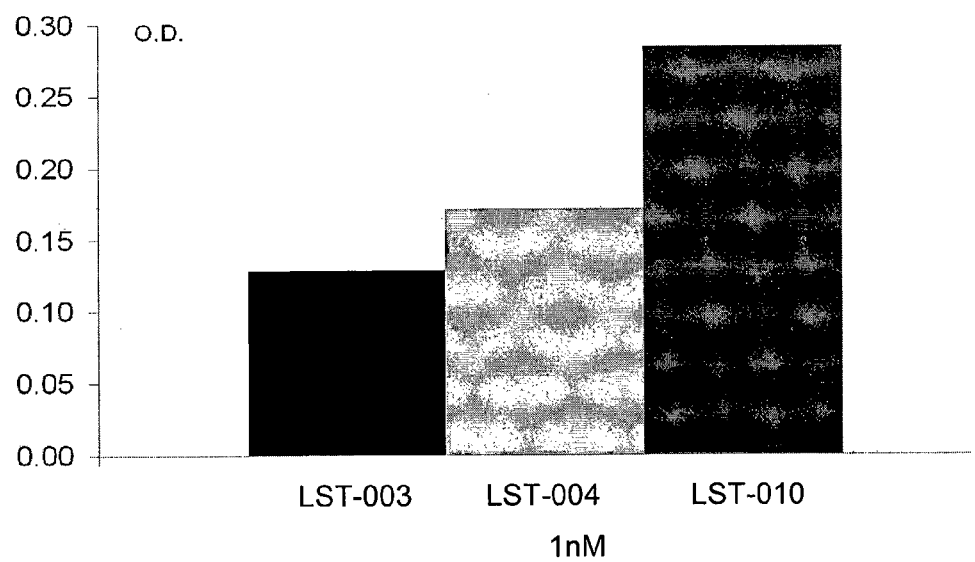
FIG. 17 shows binding properties of dual-specific mAb LST-010, LST-003 or LST-004 towards PA bacteria containing flagellin type A (PA27853) and type B (Ka02). LST-010 binding to wells containing an equal mixture of immobilized PA bacteria harboring flagellin types A and B constituted the total binding of the control LST-003 and LST-004 mAbs. OD, Optical Density.

On plates coated with PA flagellin type A, LST-009 bound the immobilized antigen, albeit with a right hand shift in potency as compared to its control mAb LST-003 (FIG. 11). To that end, LST-009's $EC_{50}$ towards *P. aeruginosa* flagellin type A was approximately 600 ng/ml as compared to LST-003 being approximately 65 ng/ml (FIG. 17). In contrast, LST-009 demonstrated high potency binding towards *P. aeruginosa* flagellin type B by ELISA (FIG. 12). LST-009's $EC_{50}$ towards this immobilized antigen was approximately 250 ng/ml as compared to the control LST-004 mAb being approximately 300 ng/ml.

7.5. Binding of LST-009 to Formaldehyde-Treated, Whole *P. Aeruginosa* Bacteria by ELISA.

From a single fresh colony, *P. aeruginosa* bacteria were grown overnight in 5 ml LB at 37° C. Thereafter, bacterial cultures were centrifuged at 1500 g for 30 min and following removal of the clear supernatant, pellets were washed twice with 20 ml PBS with intervening centrifugation. The final pellet was resuspended in a volume of PBS (~10 ml) and adjusted to generate an $OD_{600\ nm}$ of ~0.2 and maintained on ice prior to coating on ELISA plates which were prepared as follows: to the wells of flat-bottomed ELISA plates (Nunc, cat #442404), 50 µl poly-L-lysine (PLL, Sigma Cat # P-1524) of a 1 µg/ml solution was added and plates were incubated for 30 min at room temperature. Thereafter, non-adsorbed PLL was removed.

Fifty µl of the bacterial suspension at 0.2 $OD_{600\ nm}$ was added to the PLL-coated ELISA plates which were then centrifuged at 1500 rpm for 20 min to expedite bacterial adsorption. Thereafter, supernatant was removed and 75 µl of 0.2% formaldehyde added to the adsorbed bacteria for 15 min at room temperature to cause irreversible fixation of bacteria to the plates. Following removal of formaldehyde, plates were air-dried for 5 min at room temperature and taken for ELISA to characterize LST-009 binding as follows:

ELISA plates containing the fixed *P. aeruginosa* bacteria, were blocked by adding 200 µl PBS-10% FBS for 60 min at room temperature. After 60 min, block solution was flicked out, plates washed once with PBS and 50 µl LST-009 in PBS-10% FBS added over a range of concentrations and incubated for 60 min at 37° C. Following removal of the primary antibody and 3 washes with PBS-Tween (0.05%), 50 µl of a goat anti-human IgG (Fc)-HRP (Cat # A80-104P; Bethyl, Tex., USA) was added at a dilution of 1:10,000 in PBS-10% FBS with incubation allowed to proceed for 60 min at 37° C. Following 3 separate washes with PBS-Tween (0.05%) and gentle tapping of plates on paper towels to remove final traces of wash buffer, 50 µl TMB/E substrate solution (Cat # ES001-500 ml; Millipore) was added with incubation allowed to proceed for 15 min at room temperature. Thereafter, signal was quenched with 50 ml 10% $H_2SO_4$ and plates read at 450 nm in a Microtiter plate reader (Anthos MultiRead 400).

Figure 13:
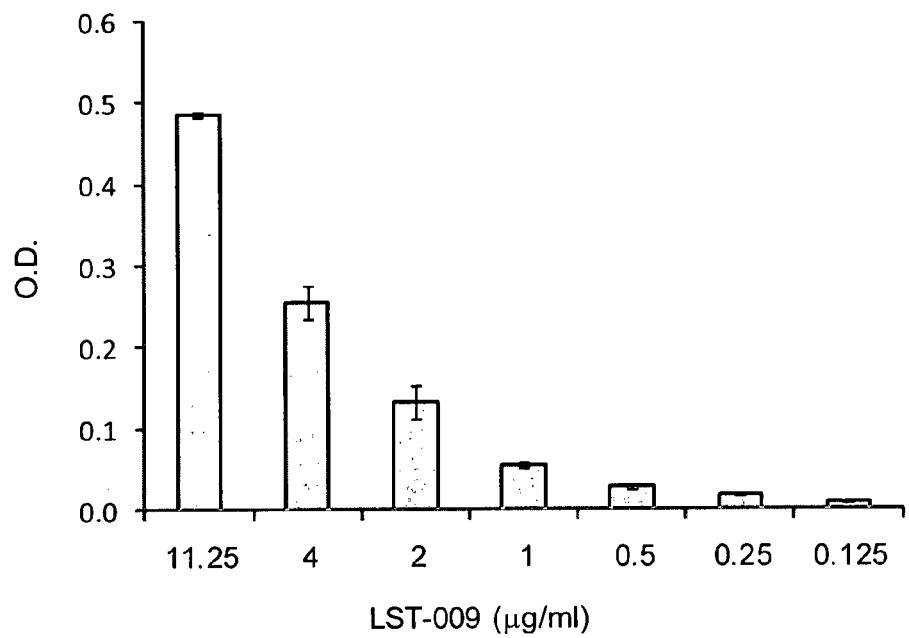
FIG. 13 shows binding of the monoclonal dual-specific anti-flagella type A and B antibody LST-009 to flagellin type A in formaldehyde-fixed PAK bacteria, by an ELISA assay; OD, Optical Density.
Figure 14:
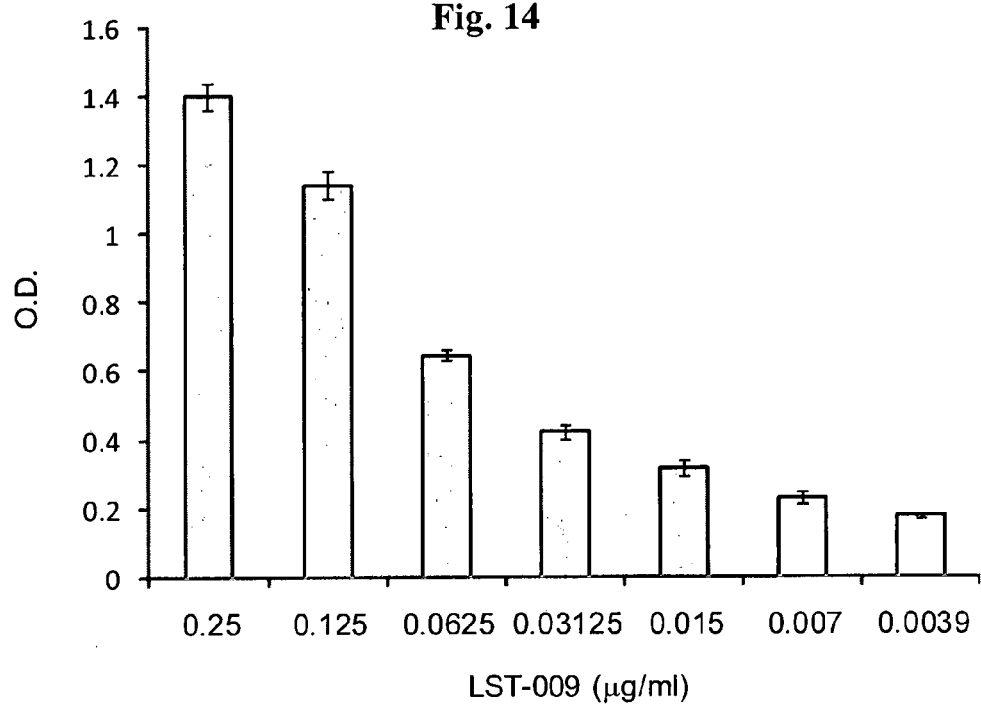
FIG. 14 shows binding of the monoclonal dual-specific anti-flagella type A and B antibody LST-009 to flagellin type B in formaldehyde-fixed Pa01 bacteria, by an ELISA assay; OD, Optical Density.

Over a mAb concentration of 0.125-11.25 µg/ml, LST-009 bound PAK in a concentration-dependent manner (FIG. 13) with an $EC_{50}$ of ~4 µg/ml. In contrast, LST-009 binding towards Pa01 was much higher with an $EC_{50}$ of approximately 80 ng/ml (FIG. 14). These data confirm LST-009's binding profile to recombinantly-expressed PA flagellin types A and B.

These findings have major implications for the design of effective bispecific mAbs targeting *P. Aeruginosa* flagellin types A and B. It would appear that the order of translation of the $V_H$ and $V_L$ fragments are critical in allowing efficient heterodimer formation and ultimate intact binding towards target antigen in which $V_L$ should be cloned upstream from $V_H$ for both scFv's.

Example 8

Production of Alternatively Designed Dual-Specific Antibodies Specifically Binding Flagellin, Type A and Type B of *P. aeruginosa*

In this example, dual-specific antibodies comprising a chimeric antibody that binds specifically to *P. aeruginosa* flagellin type A, i.e. LST-003 as described in Example 3, consisting of the original LST-001 mouse $V_H$ and $V_L$ domains (SEQ ID NO: 29 and SEQ ID NO: 30, respectively) fused to a nucleotide sequence encoding for human IgG1 constant backbone, the two heavy chains of which are connected via linker peptides consisting of $(G45)_2$ (two consecutive peptides of SEQ ID NO: 57) to the N-termini of two scFvs which binds specifically to *P. aeruginosa* flagellin type B were designed. The scFvs are identical to each other and each consists of a $V_H$ and a $V_L$ domain of LST-002 (SEQ ID NO: 31 and 50, respectively) linked together via a 7 amino acid spacer peptide of the amino acid sequence GGGSAAA (SEQ ID NO: 58).

Practically, the heavy chain of LST-003 was fused to the scFvs having binding specificity for *P. aeruginosa* flagellin type B, and this fusion polypeptide, having variable regions at each extreme of the human heavy constant backbone is of SEQ ID NO: 62. and is encoded by the nucleic acid molecule having the nucleic acid sequence as set forth in SEQ ID NO: 67

The light chain consists simply of the VL and CL domain of LST-001 and is encoded by the nucleic acid molecule having the nucleic acid sequence as set forth in SEQ ID NO: 68.

8.1 Expression and Purification of LST-010.

A recombinant, bicistronic mammalian expression plasmid harboring the complete chimeric LST-003 mAb sequence (i.e. its $V_H$, $V_L$ domains and respective human constant chains) as well as the $V_H$-$V_L$ domains of LST-004, was synthesized and optimized for expression in CHO cells (GeneArt, Germany). The resultant dual-specific chimeric mAb, coined LST-010, is structurally represented in FIG. 2.

The recombinant LST-010 mammalian plasmid was prepared at a concentration of 1 mg/ml through standard molecular biology methodologies and taken for transfection into mammalian cells. In brief, CHO-S cells were cultured in ProCHO5 CDM media (Lonza, UK), centrifuged at 200 g for 5 min and resuspended in fresh ProCHO5 CDM media at a density of $2 \times 10^6$ cells/ml. Transfection of 700 ml CHO-S cells was performed in an Erlenmeyer flask using 2.5 µg DNA and 15 µg Polyethylenimine (PEI) per ml culture, diluted in 150 mM NaCl. After 5 hrs, the transfected culture was diluted with 700 ml fresh media and incubated at 37° C. in 8% $CO_2$ with gentle agitation at 92 rpm. The supernatant was collected after 7 days post-transfection at which point it was centrifuged, clarified by filtration through 0.8 µm gyrodisc filters and taken for purification.

LST-010 was purified from two separate 700 ml batches of clarified CHO-S supernatants using an Amersham Bioscience AKTA Chromatography system. Purification method was a standard antibody purification protocol using a 1 ml Protein-A column (GE Healthcare). Following elution, peak fractions from both 700 ml purifications were taken for Bradford analysis of protein concentration and those specific fractions containing the highest concentration of LST-010 were pooled and dialyzed overnight against PBS at 4° C. Concentration of the final purified LST-010 was 130 µg/ml which was then taken for binding assays using the following two strategies: a) Binding to ELISA plates coated with recombinant PA flagellin types A or B; b) Binding to ELISA plates containing, whole, immobilized PA bacteria of flagellin types A or B.

8.1 Binding of Dual-Specific LST-010 to ELISA Plates Coated with Recombinantly-Expressed *P. aeruginosa* Flagellin Types A or B.

Two hundred and fifty ng (250 ng) of highly purified, recombinantly-expressed *P. aeruginosa* flagellin types A or B (50 µl from 5 µg/ml) were dispensed into each well of ELISA plates (Nunc, cat #442404) and coating allowed to proceed for 2 hours at room temperature with gentle shaking. Plates were then blocked with 200 µl PBS-10% fetal bovine serum (FBS) overnight at 4° C. LST-010 diluted in PBS-10% FBS was added to the antigen-coated wells. Similarly, in separate wells, LST-003 and LST-004 were included as positive controls for PA flagellin type A and B ELISA plates respectively. Since the Mw of the mAbs differ, (LST-003/004=150 kD, LST-010=200 kD), an identical mAb concentration range 0.0067-6.9 nM (as opposed to ng/ml) was employed in the ELISA. Following binding with these different primary mAbs for 2 hrs at room temperature, plates were washed with PBS-0.05% Tween-20. Thereafter, 50 µl of a goat anti-human IgG (Fc)-HRP (Cat # A80-104P; Bethyl, Tex., USA) was added at a dilution of 1:10,000 in PBS-10% FBS and incubation allowed to proceed for 60 min at room temperature. Following 3 separate washes with PBS-Tween-20 (0.05%), 50 µl TMB/E substrate solution (Cat # ES001-500 ml; Millipore) was added for 15 min at room temperature. Colorimetric development was then quenched with 50 µl 10% $H_2SO_4$ and plates read at 450 nm in a Microtiter plate reader (Anthos MultiRead 400).

Figure 15B:
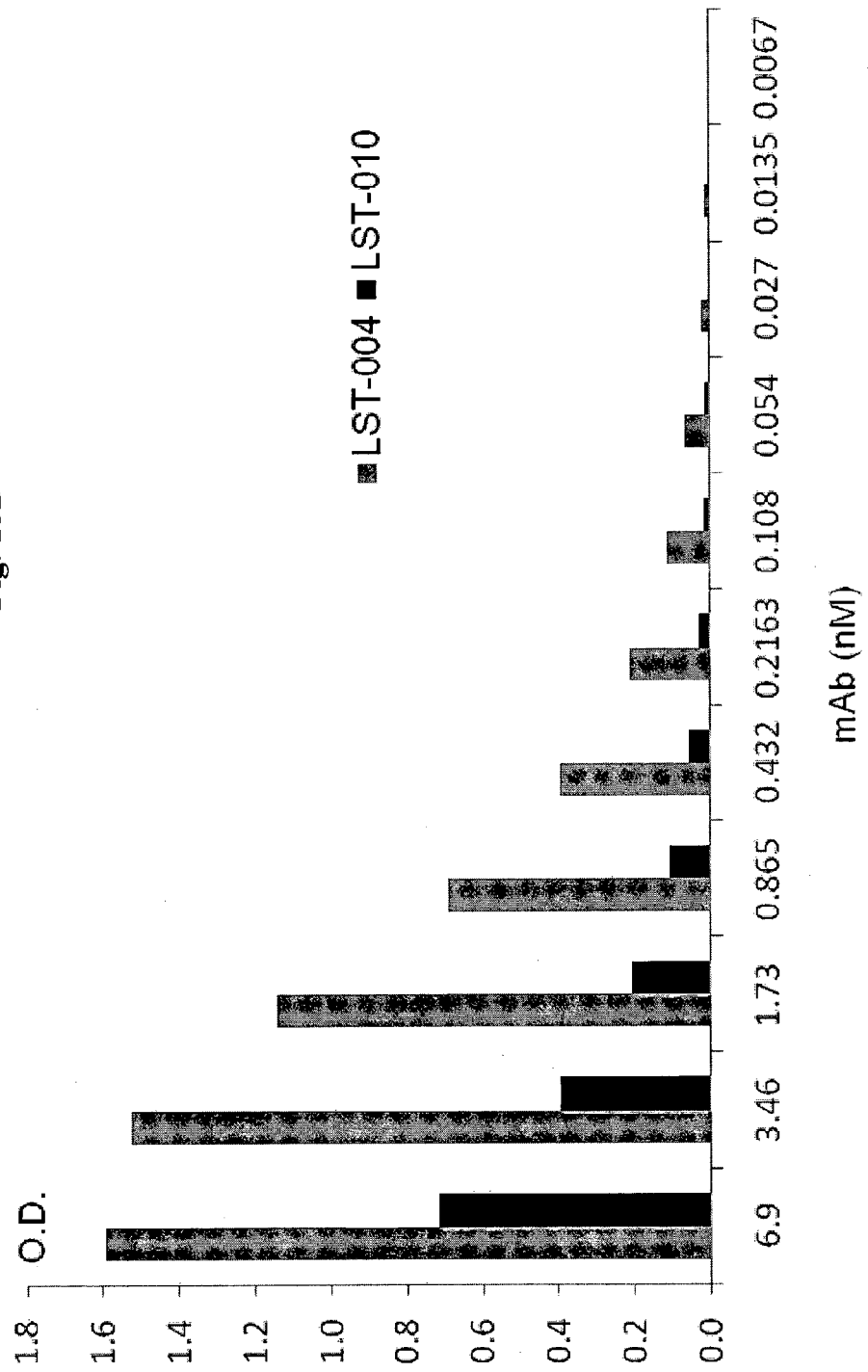

As can be seen from FIG. 15A, binding of LST-010 towards PA flagellin type A paralleled that of chimeric LST-003. Specific binding of LST-010 towards PA flagellin type B was also observed (FIG. 15B), although its signal was approximately 20-50% as compared to the positive control of LST-004.

8.2. Binding of Dual-Specific LST-010 to Immobilized, Formaldehyde-Treated, Whole *P. aeruginosa* Bacteria by ELISA.

From a single fresh bacterial colony, PA strains 27853 (harboring flagellin type A) or Ka02 (harboring flagellin type B) were grown overnight in 5 ml LB at 37° C. Thereafter, bacterial cultures were centrifuged at 1500 g for 30 min and following removal of the clear supernatant, pellets were washed twice with 20 ml PBS with intervening centrifugation. The final pellet was resuspended in a volume of PBS (~10 ml) and adjusted to generate an $OD_{600}$ of ~0.2 and maintained on ice prior to coating on ELISA plates which were prepared as follows: to the wells of flat-bottomed ELISA plates (Nunc, cat #442404), 50 µl poly-L-lysine (PLL, Sigma Cat # P-1524) of a 1 µg/ml solution was added and plates were incubated for 30 min at room temperature. Thereafter, non-adsorbed PLL was removed. Fifty µl of the appropriate bacterial suspensions from the different strains at 0.2 $OD_{600\ nm}$ were added to the PLL-coated ELISA plates. In some wells, a "mixed-bacterial population" was added. To that end, 25 µl of PA 27853 and 25 µl of Ka02 bacterial suspensions were added to the same wells. Plates were then centrifuged at 1500 rpm for 20 min to expedite bacterial adsorption, supernatant removed and 75 µl of 0.2% formaldehyde added to the adsorbed bacteria for 15 min at room temperature to cause irreversible fixation of bacteria to the plates. Following removal of formaldehyde, plates were air-dried for 5 min at room temperature and taken for ELISA to characterize LST-010 binding as well as the appropriate controls of LST-003 and LST-004 as follows:

ELISA plates containing the fixed *P. aeruginosa* bacteria, were blocked by adding 200 µl PBS-10% FBS for 60 min at room temperature. After 60 min, block solution was flicked out, plates washed once with PBS and 50 µl mAbs in PBS-10% FBS added at a final concentration of 1 nM and incubated for 60 min at 37° C. Following removal of the primary antibodies and 3 washes with PBS-Tween (0.05%), 50 µl of a goat anti-human IgG (Fc)-HRP (Cat # A80-104P; Bethyl, Tex., USA) was added at a dilution of 1:10,000 in PBS-10% FBS with incubation allowed to proceed for 60 min at 37° C. Following 3 separate washes with PBS-Tween (0.05%) and gentle tapping of plates on paper towels to remove final traces of wash buffer, 50 µA TMB/E substrate solution (Cat # ES001-500 ml; Millipore) was added with incubation allowed to proceed for 15 min at room temperature. Thereafter, signal was quenched with 50 µA 10% $H_2SO_4$ and plates read at 450 nm in a Microtiter plate reader (Anthos MultiRead 400).

In the bacterial binding assay, we used LST-010 at a final concentration of 1 nM since this represents the approximate affinity constants for its 2 components, LST-003 and LST-004. As can be seen from FIG. 16, LST-010 bound PA27853 at a similar signal observed with its control mAb LST-003. Also, binding of LST-010 towards Ka02 was positive although its signal was approximately 40% of that observed with LST-004. As anticipated, LST-003 failed to bind Ka02 with minimal signal of LST-004 towards PA27853.

Furthermore, LST-010 was capable of binding immobilized, "mixed" bacteria in wells containing PA27853 and Ka02 (FIG. 17). In this experiment, individual wells were coated with half the amount of bacteria for both PA27853 and Ka02 strains as used in the study depicted in FIG. 16. Thus on binding, OD's generated with 1 nM LST-003 and LST-004 were approximately 50% as compared to FIG. 16. Importantly, LST-010 (1 nM) was able to bind both bacterial populations within the same well since the OD generated constituted the sum of binding of LST-003 and LST-004 (FIG. 17). These critical data would indicate that the dual specific mAb LST-010 is capable of binding mixed PA populations (flagellin types A and B) at its presumed $K_D$, thereby representing a therapeutic target concentration.

A corresponding dual-specific antibody is produced in which the chimeric or humanized antibody module is specific for *P. aeruginosa* flagellin type B, and the scFvs are specific for *P. aeruginosa* flagellin type A.

Example 9

Characterization of the Mabs Binding *P. aeruginosa* Flagellin Types A and B by Surface Plasmon Resonance (SPR)

The binding affinities of 6 different mAbs (Table 2) were determined using the ProteOn™ XPR36 protein interaction array system utilizing SPR instrumentation. mAbs were bound onto a ProteOn GLM sensor chip using standard amine coupling chemistry. In general, 5,000-10,000 relative units (RU) of mAbs were immobilized. Thereafter, 5 different concentrations of analyte (PA flagellin type A or B) from 5-80 nM were injected in a volume of 100 µl at a flow rate of 50 ml/min Six concentration-dependent sensorgrams were obtained for each mAb to generate RU versus run time (min) plots. Full kinetic rat constant determinations were generated using a simple 1:1 interaction model and the kinetic constants and subsequent $K_D$ values obtained.

Both LST-003 and LST-004 chimeric mAbs retained similar affinities towards PA flagellin type A and B respectively which were highly comparable to their parental mouse mAbs LST-001 and LST-002 (Table 2). Interestingly, the affinity of the type B binding component of the dual-specific mAb LST-009 was 0.8 nM, being essentially identical to its parental LST-002/LST-004 mAbs which harbor the identical $V_H$ and $V_L$ sequences. The newly created fully human mAb LST-008 which contained a human IgG1 constant domain exhibited a high affinity of 0.94 nM towards PA flagellin type B. This finding is of interest since its parental mAb (LST-007) which is of the IgM type, are generally considered as lower affinity mAbs.

TABLE 2

Affinity constants (nM) of mAbs binding *P. aeruginosa* flagellin types A and B.

| mAb | Antigen tested | $K_D$ Affinity Constant (nM) |
| --- | --- | --- |
| LST-001 | PA flagellin A | 0.6 |
| LST-002 | PA flagellin B | 0.82 |

TABLE 2-continued

Affinity constants (nM) of mAbs binding *P. aeruginosa* flagellin types A and B.

| mAb | Antigen tested | $K_D$ Affinity Constant (nM) |
|---|---|---|
| LST-003 | PA flagellin A | 3 |
| LST-004 | PA flagellin B | 1.3 |
| LST-008 | PA flagellin B | 0.94 |
| LST-009 | PA flagellin B | 0.8 |

Example 10

In Vivo Experiments 10.1 LST-002 is Efficacious in the Treatment of Multidrug-Resistant *P. aeruginosa* Model of Pneumonia Experiment #1.

Sixty-one (61) male Adult C57 Black mice (25-30 g, Harlan Nossan, Milan, Italy) were housed in a controlled environment in cages with filter tops in specific pathogen-free conditions. They were briefly anesthetized with inhaled sevorane (Abbot Laboratories) in an oxygenated chamber and placed in a supine position with their heads elevated approximately 30°. Ka02 bacterial inoculums ($10^6$ cfu's in 50 µl of lactated Ringer's solution) were instilled slowly into the left lung of each animal using a gavage needle.

Mice were randomly divided into 3 experimental treatment groups as follows:

a) Saline-Treated (n=20): saline administered i.v. 1 hr after infection followed by one further i.p. administration at 5 hr post-infection; b) LST-002-Treated (n=21): LST-002 given i.v. 1 hr after infection at a dose of 20 mg/kg followed by one further i.p. administration at 5 hr post-infection at a dose of 15 mg/kg; c) Positive control-Imipenem-Treated (n=20): "Tienam" (Merck, Sharpe and Dohme)] (active ingredient, imipenem, a carbapenem antibiotic) given i.p. 1 hr after infection at a dose of 25 mg/kg followed by further i.p. administrations at 25 mg/kg at time points of 5 hr, 24 hr, 29 hr, 48 hr and 53 hr following infection.

Figure 18:
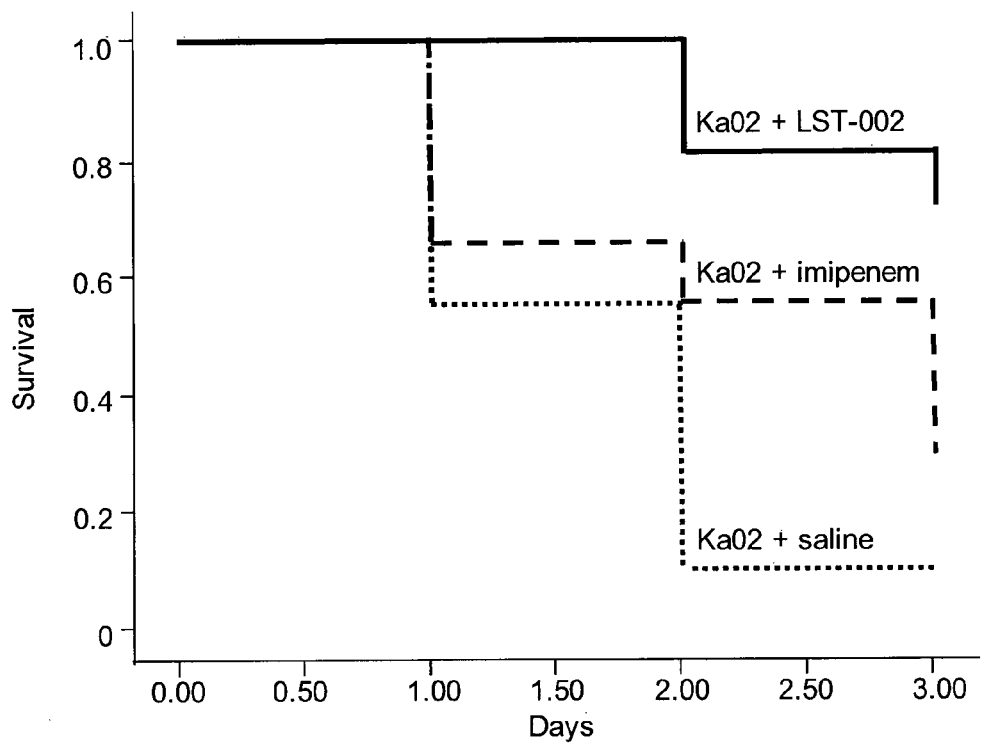
FIG. 18 demonstrates the superiority of LST-002 vs. imipenem in preventing mortality in a mouse model of pneumonia driven by Ka02, a MDR PA bacterial strain. Data represents Kaplan-Meier survival curves of infected mice treated with saline, LST-002 or imipenem over a 3 day post-infection period. Survival at 3 days in mice treated with LST-002 was highly significant (p<0.0001) as compared to saline or imipenem-treated animals using Fisher's exact test. Identical survival numbers and statistical analysis were obtained at day 9 post-infection.

Survival was monitored for all groups every 12 hrs until day 9 post-infection and data depicted in Kaplan-Meier curves (FIG. 18). As can be seen from FIG. 18, LST-002 significantly improved survival over a 3 day period following infection which was superior to saline-treated and imipenem-treated animals. Animal survival at day 3 was 71.4% for LST-002 (15/21 survivors), 30% for imipenem (6/20 survivors) and 10% for saline (2/20 survivors). Survival at day 9 was unchanged from survival data observed at day 3, i.e. LST-002 was 240% more efficacious in increasing survival in mice with pneumonia than a currently accepted treatment protocol and increased survival by 700% as compared with untreated mice.

Experiment #2:

LST-002 is Efficacious in the Treatment of Multidrug-Resistant *P. aeruginosa* Model of Thigh Muscle Infection.

The effect of LST-002 on thigh muscle abscess infection triggered by the intra-muscular administration of MDR PA strain Ka02 was examined. Female CD-1 mice weighing 23-27 g (3-5 weeks in age) were rendered neutropenic by split i.p. administration of cyclophosphamide at doses of 150 mg/kg and 100 mg/kg on days 0 and +3. On day 4, 50 µl of freshly-grown Ka02 ($2 \times 10^7$ cfu's per ml) was injected at a depth of 5 mm into the right thigh muscle ("ipsilateral") whereas an equivalent volume of saline was injected into the left thigh muscle ("contralateral"). Over an ensuing 3 day period (days 5-7, i.e. 24, 48 and 72 hr following Ka02 administration), the surface areas of the infected thigh muscle lesions were measured with calipers in both ipsilateral and contralateral muscles. Ratios of surface areas of infection lesions of ipsilateral muscles divided by contralateral muscle lesions were calculated with ratios >1 indicative of Ka02. This calculation is called the Ratio-Infection Index (RII). In some mice, LST-002 was administered i.v. at 20 mg/kg, 60 min after administration of Ka02. Further dosing of LST-002 (10 mg/kg) was given i.p. at time points+5 hr, +24 hr and +48 hr after infection.

Figure 19:
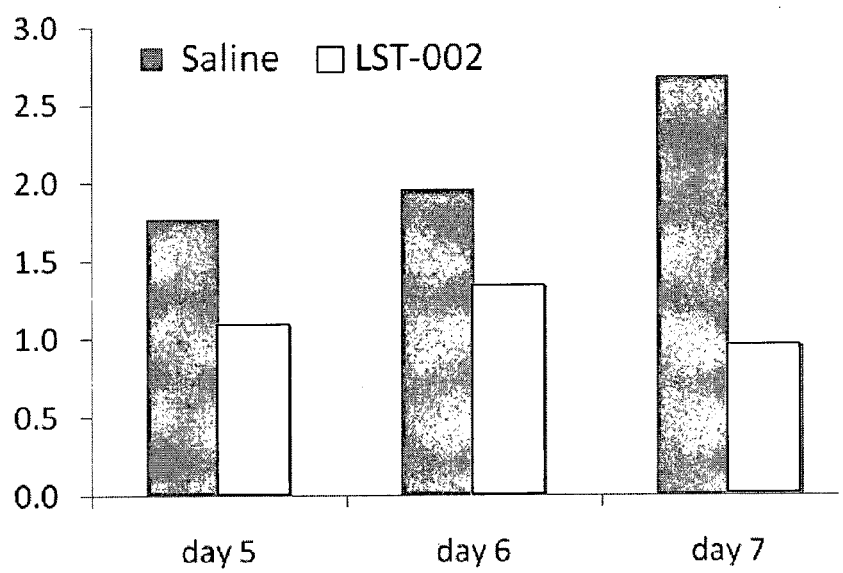
FIG. 19 depicts the effect of LST-002 on Ka02-mediated thigh muscle infection. Data represents the Ratio-Infection Index (RII; ordinate axis) of the surface-area of thigh muscle infection in ipsilateral muscle to contralateral muscle in saline and LST-002 treated mice as a function of days (abscissa) following 2 separate injections of cyclophosphamide (day 0 and day 3), with Ka02 being injected at day 4. LST-002 was administered i.v. at 20 mg/kg, 60 min after administration of Ka02. Further dosing of LST-002 (10 mg/kg) was given i.p. at time points+5 hr, +24 hr and +48 hr after infection.

As can be seen from FIG. 19, RII in mice challenged with Ka02/saline, increased from day 5 (1.78) to day 7 (2.68). This increase was prevented in mice treated with LST-002 since RII's on day 5 and 7 were 1.09 and 0.96 respectively.

Chimeric, humanized and dual-specific antibodies specific for *P. Aeruginosa* flagellin type A, B, or both, are further employed in Experiments 1 and 2 above.

10.2 *P. aeruginosa* Infection in Burn Model.

In another animal model, normal mice are exposed to a localized burn on their back followed by an immediate subcutaneous injection of *P. aeruginosa* bacteria. In this lethal model, the antibodies are given intravenously, intraperitoneally, subcutaneously or by inhalation in various experimental paradigms as described below to quantitative their biological effect in preventing lethality and/or attenuating bacterial invasion to organs.

10.3 The Following Experiments are Performed Using Antibodies Specific for *P. aeruginosa* Flagellin Type A or B:

Chimeric, humanized, recombinant fully human or dual-specific antibodies given prophylactically and/or post-infection versus *P. Aeruginosa* clinical isolates bearing type A or B flagellin Chimeric, humanized, recombinant fully human or dual-specific antibodies given in combination with an antibiotic prophylactically and/or post-infection versus *P. Aeruginosa* clinical isolates bearing type A or B flagellin.

Chimeric, humanized, recombinant fully human or dual-specific antibodies given prophylactically and/or post-infection versus anti-biotic resistant *P. Aeruginosa* clinical isolates bearing type A or B flagellin Combination of chimeric anti-flagellin type A and anti-flagellin type B antibodies, humanized anti-flagellin type A and anti-flagellin type B antibodies, recombinant human anti-flagellin type A and anti-flagellin type B antibodies or dual-specific antibodies, given prophylactically and/or post-infection versus *P. Aeruginosa* clinical isolates bearing type A and type B flagellin or versus anti-biotic resistant *P. Aeruginosa* clinical isolates bearing type A and type B flagellin in combination with—or without—an antibiotic given prophylactically and/or post-infection.

REFERENCES

Almagro J C, Fransson J. Humanization of antibodies. Frontiers in Bioscience 13, 1619-1633, Jan. 1, 2008

Ansorg, Flagella Specific H Antigenic Schema of *Pseudomonas aeruginosa*. Zbl. Bakt. Hyg., I. Abt. Orig. A, vol. 242 (1978), pp. 228-238.

Brochet X, Lefranc M P, Giudicelli V. IMGT/V-QUEST: the highly customized and integrated system for IG and TR standardized V-J and V-D-J sequence analysis. Nucleic Acids Res. 2008 Jul. 1; 36: W503-8.

Chothia, C. & Lesk, A. M. "Canonical Structures for the Hypervariable Regions of Immunoglobulins," J. Mol. Biol. (1987), vol. 197, pp. 901-917.

Chothia, C., Lesk, A. M., Gherardi, E., Tomlinson, I. M., Walter, G., Marks, J. D., Llewelyn, M. B. & Winter, G. "Structural Repertoire of the Human VH Segments," J. Mol. Biol. (1992), vol. 227, pp. 799-817.

Drake D, and Montie T C. Protection against *Pseudomonas aeruginosa* infection by passive transfer of anti-flagellar serum. Can. J. Microbiol. 1987; 33:755-63.

Edward-Jones V, Greenwood J E. On behalf of the Manchester Burns Research Group 2003. What's new in burn microbiology? James Laing Memorial Prize Essay. Burns. 2000; 29:15-24.

Singh N P, Goyal R, Manchanda V, et al. Changing trends in bacteriology of burns in the burns unit, Delhi, India. Burns. 2003; 29:129-132.

Eaves-Pyles T, Szabo C, Salzman A L. Bacterial invasion is not required for activation of NF-kappaB in enterocytes. Infection and Immunity 1999; 67: 800-04.

Kufer P, Ralf Lutterbuse and Patrick A. Baeuerle. A revival of bispecific antibodies. TRENDS in Biotechnology Vol. 22 No. 5 May 2004.

Landsperger W J, Kelly-Wintenberg K D, Montie T C, Knight L S, Hansen M B, Huntenburg C C, Schneidkraut M J Inhibition of bacterial motility with human antiflagellar monoclonal antibodies attenuates *Pseudomonas aeruginosa-induced* Pneumonia in the immunocompetent rat. Infection and Immunity 1994; 62: 4825-30.

Lanyi, B. Serological properties of *Pseudomonas aeruginosa*. II. Type-specific thermolabile (flagellar) antigens. Acta Microbiol. Acad. Sci. Hung., (1970) 17:35-48.

Matsumoto T, Tateda K, Miyazaki S, Furuya N, Ohno A, Ishii Y, Hirakata Y, and Yamaguchi K. Effect of antiflagellar human monoclonal antibody on gut-derived *Pseudomonas aeruginosa* sepsis in mice. Clin. Diagn. Lab. Immunol. 1999; 6: 537-41

Oishi K, Sonoda F, Iwagaki A et al. Therapeutic effects of a human antiflagella monoclonal antibody in a neutropenic murine model of *Pseudomonas aeruginosa* pneumonia. Antimicrobial agents and Chemotherapy 1993; 37: 164-70.

Rosok M J, Stebbins M R, Connelly K, Lostrom M E, Siadak, A W. Generation and characterization of murine antiflagellum monoclonal antibodies that are protective against lethal challenge with *Pseudomonas aeruginosa*. Infect. Immun 1990; 58:3819-28.

Sanger F, Nicklen S, and Coulson A R. DNA sequencing with chain-terminating inhibitors. Proc Natl Acad Sci USA. 1977 December; 74(12):5463-7

Steiner T S, Lima A A, Nataro J P and Guerrant R L. Enteroaggregative *Escherichia coli* produce intestinal inflammation and growth impairment and cause IL-8 release from intestinal epithelial cells. J Inf Dis 1998; 177: 88-96.

Wu T T and Kabat E A. An analysis of the sequences of the variable regions of Bence Jones proteins and myeloma light chains and their implications for antibody complementarity. J Exp Med. 1970 Aug. 1; 132(2):211-50.

Yamashita, M., Katakura Y., Shirahata S. Recent advances in the generation of human monoclonal. Antibody. Cytotechnology (2007) 55:55-60.

Roux K H Immunoglobulin structure and function as revealed by electron microscopy. Int Arch Allergy Immunol (1999) 120: 85-89.

The invention claimed is:

1. An antibody that specifically binds to flagella type B of *P. aeruginosa*, wherein the antibody comprises a VH fragment comprising a complementarity determining region (CDR) 1 comprising the amino acid sequence of SEQ ID NO: 3 or SEQ ID NO: 6, a CDR2 comprising the amino acid sequence of SEQ ID NO: 4 or SEQ ID NO: 7, and a CDR3 comprising the amino acid sequence of SEQ ID NO: 5 or SEQ ID NO: 8; and a VL fragment comprising a CDR1 comprising the amino acid sequence of SEQ ID NO: 9 or SEQ ID NO: 11, a CDR2 comprising the amino acid sequence of AAS or SEQ ID NO: 12, and a CDR3 comprising the amino acid sequence of SEQ ID NO: 10.

2. The antibody according to claim 1, which is a human antibody comprising a human IgG constant region fused to human variable regions of an anti-*P. aeruginosa* monoclonal antibody that specifically binds to flagella type B.

3. The antibody according to claim 2, wherein said IgG constant region is a human IgG1 constant region.

4. The antibody according to claim 1, wherein the antibody is covalently linked, optionally via a cleavable linker, to an antibiotic agent.

5. The antibody according to claim 4, wherein said antibiotic agent is selected from the group consisting of Amikacin, Ampicillin/Sulbactam, Amoxicillin/Calvulanic acid, Aztreonam, Cefepime, Cefotaxime, Ceftazidime, Chloramphenical, Ciprofloxacin, Colistin, Doripenem, Gentamicin, Imipenem, Levofloxacin, Meropenem, Minocycline, Piperacillin, Piperacillin/Tazobactam, Ticracillin, Tigecycline, Tobramycin and Trimethoprim-Sulfamethoxazole.

6. The antibody according to claim 1, wherein the antibody is covalently linked to a nonproteinaceous polymer, such as polyethyleneglycol.

7. An antigen binding fragment of the antibody according to claim 1, wherein said fragment binds flagella type B of *P. aeruginosa* and wherein said fragment comprises a VH fragment comprising a CDR1 comprising the amino acid sequence of SEQ ID NO: 3 or SEQ ID NO: 6, a CDR2 comprising the amino acid sequence of SEQ ID NO: 4 or SEQ ID NO: 7, and a CDR3 comprising the amino acid sequence of SEQ ID NO: 5 or SEQ ID NO: 8; and a VL fragment comprising a CDR1 comprising the amino acid sequence of SEQ ID NO: 9 or SEQ ID NO: 11, a CDR2 comprising the amino acid sequence of AAS or SEQ ID NO: 12, and a CDR3 comprising the amino acid sequence of SEQ ID NO: 10.

8. A pharmaceutical composition comprising at least one antibody according to claim 1.

9. A pharmaceutical composition comprising at least one antigen binding fragment according to claim 7.

* * * * *

```
                        SEQUENCE LISTING

<160> NUMBER OF SEQ ID NOS: 72

<210> SEQ ID NO 1
<211> LENGTH: 118
<212> TYPE: PRT
<213> ORGANISM: Artificial Sequence
<220> FEATURE:
<223> OTHER INFORMATION: synthetic peptide

<400> SEQUENCE: 1

Gln Val Arg Leu Val Gln Ser Gly Thr Glu Val Lys Lys Pro Gly Ala
1               5                   10                  15

Ser Val Arg Val Ser Cys Lys Ala Ser Gly Tyr Thr Phe Ser Asn Tyr
            20                  25                  30

Tyr Met Tyr Trp Val Arg Gln Ala Pro Gly Gln Gly Leu Glu Trp Met
        35                  40                  45

Ala Met Ile Asn Pro Ser Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Asp Ser Gly Ser Tyr Phe Gly Tyr Trp Gly Gln Gly Thr
            100                 105                 110

Leu Val Thr Val Ser Ser
        115
```

```
<210> SEQ ID NO 2
<211> LENGTH: 108
<212> TYPE: PRT
<213> ORGANISM: Artificial Sequence
<220> FEATURE:
<223> OTHER INFORMATION: synthetic peptide

<400> SEQUENCE: 2

Asp Ile Gln Leu Thr Gln Ser Pro Ser Phe Leu Ser Ala Ser Val Gly
1               5                   10                  15

Asp Arg Val Pro Ile Thr Cys Arg Ala Ser Gln Gly Ile Ser Thr His
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Gln Gln Leu Lys Ser Tyr Pro Leu
                85                  90                  95

Thr Phe Gly Gly Gly Thr Lys Val Glu Ile Lys Arg
            100                 105

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Gly Tyr Thr Phe Ser Asn Tyr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Ile Asn Pro Ser Gly Gly Ser Thr
1               5

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Ala Arg Ala Asp Ser Gly Ser Tyr Phe Gly Tyr
1               5                   10

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Asn Tyr Tyr Met Tyr
```

```
<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Met Ile Asn Pro Ser Gly Gly Ser Thr Arg Tyr Ala Gln Lys Phe Gln
1               5                   10                  15
Gly

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Ala Asp Ser Gly Ser Tyr Phe Gly Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide

<400> SEQUENCE: 9

Gln Gly Ile Ser Thr His
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Gln Gln Leu Lys Ser Tyr Pro Leu Thr
1               5

<210> SEQ ID NO 11
<211> LENGTH: 11
<212> TYPE: PRT
<213> ORGANISM: Artificial Sequence
<220> FEATURE:
<223> OTHER INFORMATION: synthetic peptide

<400> SEQUENCE: 11

Arg Ala Ser Gln Gly Ile Ser Thr His Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: synthetic peptide

<400> SEQUENCE: 12

Ala Ala Ser Thr Leu Gln Ser
```

<210> SEQ ID NO 13
<211> LENGTH: 137
<212> TYPE: PRT
<213> ORGANISM: Artificial Sequence
<220> FEATURE:
<223> OTHER INFORMATION: synthetic peptide

<400> SEQUENCE: 13

Met Asp Trp Thr Trp Arg Val Phe Phe Leu Leu Ala Val Ala Pro Gly
1               5                   10                  15

Ala His Ser Gln Val Arg Leu Val Gln Ser Gly Thr Glu Val Lys Lys
            20                  25                  30

Pro Gly Ala Ser Val Arg Val Ser Cys Lys Ala Ser Gly Tyr Thr Phe
        35                  40                  45

Ser Asn Tyr Tyr Met Tyr Trp Val Arg Gln Ala Pro Gly Gln Gly Leu
    50                  55                  60

Glu Trp Met Ala Met Ile Asn Pro Ser Gly Gly Ser Thr Arg Tyr Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ala Asp Ser Gly Ser Tyr Phe Gly Tyr Trp Gly
        115                 120                 125

Gln Gly Thr Leu Val Thr Val Ser Ser
    130                 135

<210> SEQ ID NO 14
<211> LENGTH: 128
<212> TYPE: PRT
<213> ORGANISM: Artificial Sequence
<220> FEATURE:
<223> OTHER INFORMATION: synthetic peptide

<400> SEQUENCE: 14

Met Arg Val Pro Ala Gln Leu Leu Gly Leu Leu Leu Leu Trp Leu Pro
1               5                   10                  15

Gly Ala Arg Cys Asp Ile Gln Leu Thr Gln Ser Pro Ser Phe Leu Ser
            20                  25                  30

Ala Ser Val Gly Asp Arg Val Pro Ile Thr Cys Arg Ala Ser Gln Gly
        35                  40                  45

Ile Ser Thr His Leu Ala Trp Tyr Gln Gln Lys Pro Gly Lys Ala Pro
    50                  55                  60

Lys Leu Leu Ile Tyr Ala Ala Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Ser Ala Thr Tyr Tyr Cys Gln Gln Leu Lys
            100                 105                 110

Ser Tyr Pro Leu Thr Phe Gly Gly Thr Lys Val Glu Ile Lys Arg
        115                 120                 125

<210> SEQ ID NO 15
<211> LENGTH: 467
<212> TYPE: PRT
<213> ORGANISM: Artificial Sequence
<220> FEATURE:
<223> OTHER INFORMATION: synthetic peptide

<400> SEQUENCE: 15

```
Met Asp Trp Thr Trp Arg Val Phe Cys Leu Leu Ala Val Ala Pro Gly
1               5                   10                  15

Ala His Ser Gln Val Arg Leu Val Gln Ser Gly Thr Glu Val Lys Lys
            20                  25                  30

Pro Gly Ala Ser Val Arg Val Ser Cys Lys Ala Ser Gly Tyr Thr Phe
        35                  40                  45

Ser Asn Tyr Tyr Met Tyr Trp Val Arg Gln Ala Pro Gly Gln Gly Leu
    50                  55                  60

Glu Trp Met Ala Met Ile Asn Pro Ser Gly Gly Ser Thr Arg Tyr Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ala Asp Ser Gly Ser Tyr Phe Gly Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

```
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 16
<211> LENGTH: 234
<212> TYPE: PRT
<213> ORGANISM: Artificial Sequence
<220> FEATURE:
<223> OTHER INFORMATION: synthetic peptide

<400> SEQUENCE: 16

Met Arg Val Pro Ala Gln Leu Leu Gly Leu Leu Leu Leu Trp Leu Pro
1               5                   10                  15

Gly Ala Arg Cys Asp Ile Gln Leu Thr Gln Ser Pro Ser Phe Leu Ser
            20                  25                  30

Ala Ser Val Gly Asp Arg Val Pro Ile Thr Cys Arg Ala Ser Gln Gly
        35                  40                  45

Ile Ser Thr His Leu Ala Trp Tyr Gln Gln Lys Pro Gly Lys Ala Pro
    50                  55                  60

Lys Leu Leu Ile Tyr Ala Ala Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Ser Ala Thr Tyr Tyr Cys Gln Gln Leu Lys
            100                 105                 110

Ser Tyr Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 17
<211> LENGTH: 117
<212> TYPE: PRT
<213> ORGANISM: Artificial Sequence
<220> FEATURE:
<223> OTHER INFORMATION: synthetic peptide

<400> SEQUENCE: 17

Asp Val Gln Leu Gln Glu Ser Gly Pro Gly Leu Val Lys Pro Ser Gln
1               5                   10                  15
```

Ser Leu Ser Leu Pro Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
                35                  40                  45

Met Gly Tyr Ile Arg Tyr Asp Gly Asn Asn Tyr Asn Pro Ser Leu
 50                  55                  60

Lys Asn Arg Ile Ser Ile Thr His Asp Thr Ser Lys Asn Gln Phe Phe
 65                  70                  75                  80

Leu Lys Leu Asn Tyr Val Thr Thr Glu Asp Thr Ala Thr Tyr Tyr Cys
                85                  90                  95

Ala Arg Gly Leu Gln Phe Tyr Phe Asp Ser Trp Gly Gln Gly Thr Thr
            100                 105                 110

Leu Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: synthetic peptide

<400> SEQUENCE: 18

Asp Ile Val Met Ser Gln Ser Pro Ser Ser Leu Ala Val Ser Gly Gly
1               5                   10                  15

Glu Lys Val Thr Met Ser Cys Lys Ser Ser Gln Ser Leu Leu Asn Gly
            20                  25                  30

Ser Tyr Gln Lys His Thr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys Arg

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Gly Tyr Ser Ile Thr Ser Gly Tyr Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ile Arg Tyr Asp Gly Asn Asn
1               5

<210> SEQ ID NO 21
<211> LENGTH: 10
<212> TYPE: PRT
<213> ORGANISM: Artificial Sequence
<220> FEATURE:
<223> OTHER INFORMATION: synthetic peptide

<400> SEQUENCE: 21

Ala Arg Gly Leu Gln Phe Tyr Phe Asp Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthetic peptide

<400> SEQUENCE: 22

Gly Tyr Ser Ile Thr Ser Gly Tyr Tyr Trp Asn
1               5                   10

<210> SEQ ID NO 23
<211> LENGTH: 16
<212> TYPE: PRT
<213> ORGANISM: Artificial Sequence
<220> FEATURE:
<223> OTHER INFORMATION: synthetic peptide

<400> SEQUENCE: 23

Tyr Ile Arg Tyr Asp Gly Asn Asn Asn Tyr Asn Pro Ser Leu Lys Asn
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: synthetic peptide

<400> SEQUENCE: 24

Gly Leu Gln Phe Tyr Phe Asp Ser
1               5

<210> SEQ ID NO 25
<211> LENGTH: 12
<212> TYPE: PRT
<213> ORGANISM: Artificial Sequence
<220> FEATURE:
<223> OTHER INFORMATION: synthetic peptide

<400> SEQUENCE: 25

Gln Ser Leu Leu Asn Gly Ser Tyr Gln Lys His Thr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26

Gln Gln Tyr Tyr Ser Tyr Pro Trp Thr
1               5

```
<210> SEQ ID NO 27
<211> LENGTH: 17
<212> TYPE: PRT
<213> ORGANISM: Artificial Sequence
<220> FEATURE:
<223> OTHER INFORMATION: synthetic peptide

<400> SEQUENCE: 27

Lys Ser Ser Gln Ser Leu Leu Asn Gly Ser Tyr Gln Lys His Thr Leu
1               5                   10                  15

Ala

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28

Trp Ala Ser Thr Arg Glu Ser
1               5

<210> SEQ ID NO 29
<211> LENGTH: 135
<212> TYPE: PRT
<213> ORGANISM: Artificial Sequence
<220> FEATURE:
<223> OTHER INFORMATION: synthetic peptide

<400> SEQUENCE: 29

Met Met Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Pro Cys Ser Val Thr Gly Tyr Ser Ile Thr
            35                  40                  45

Ser Gly Tyr Tyr Trp Asn Trp Ile Arg Gln Phe Pro Gly Asn Lys Leu
        50                  55                  60

Glu Trp Met Gly Tyr Ile Arg Tyr Asp Gly Asn Asn Asn Tyr Asn Pro
65                  70                  75                  80

Ser Leu Lys Asn Arg Ile Ser Ile Thr His Asp Thr Ser Lys Asn Gln
                85                  90                  95

Phe Phe Leu Lys Leu Asn Tyr Val Thr Thr Glu Asp Thr Ala Thr Tyr
                100                 105                 110

Tyr Cys Ala Arg Gly Leu Gln Phe Tyr Phe Asp Ser Trp Gly Gln Gly
            115                 120                 125

Thr Thr Leu Thr Val Ser Ser
        130                 135

<210> SEQ ID NO 30
<211> LENGTH: 129
<212> TYPE: PRT
<213> ORGANISM: Artificial Sequence
<220> FEATURE:
<223> OTHER INFORMATION: synthetic peptide

<400> SEQUENCE: 30

Met Val Leu Ile Leu Leu Leu Trp Val Ser Gly Thr Cys Gly Asp
1               5                   10                  15

Ile Val Met Ser Gln Ser Pro Ser Ser Leu Ala Val Ser Gly Gly Glu
                20                  25                  30
```

Lys Val Thr Met Ser Cys Lys Ser Ser Gln Ser Leu Leu Asn Gly Ser
            35                  40                  45

Tyr Gln Lys His Thr Leu Ala Trp Tyr Gln Gln Lys Pro Gly Gln Ser
    50                  55                  60

Pro Lys Leu Leu Ile Tyr Trp Ala Ser Thr Arg Glu Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Lys Ala Glu Asp Leu Ala Val Tyr Tyr Cys Gln Gln Tyr
                100                 105                 110

Tyr Ser Tyr Pro Trp Thr Phe Gly Gly Gly Thr Lys Leu Glu Ile Lys
            115                 120                 125

Arg

<210> SEQ ID NO 31
<211> LENGTH: 118
<212> TYPE: PRT
<213> ORGANISM: Artificial Sequence
<220> FEATURE:
<223> OTHER INFORMATION: synthetic peptide

<400> SEQUENCE: 31

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Phe
                20                  25                  30

Thr Met Ser Trp Val Arg Gln Thr Pro Glu Lys Arg Leu Glu Cys Val
            35                  40                  45

Ala Thr Ile Asn Gly Gly Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Phe Tyr Phe Cys
                85                  90                  95

Ser Arg Leu Tyr Gly Ile Tyr Ala Met Asp Tyr Trp Gly Gln Gly Thr
                100                 105                 110

Ser Val Thr Val Ser Ser
            115

<210> SEQ ID NO 32
<211> LENGTH: 108
<212> TYPE: PRT
<213> ORGANISM: Artificial Sequence
<220> FEATURE:
<223> OTHER INFORMATION: synthetic peptide

<400> SEQUENCE: 32

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Gly Ser Ala
                20                  25                  30

Val Ala Trp Tyr Gln Gln Lys Pro Gly Gln Ser Pro Lys Val Leu Ile
            35                  40                  45

Tyr Trp Thr Ser Thr Arg His Thr Gly Val Pro Asp Arg Phe Ala Gly
    50                  55                  60

Ser Gly Ser Gly Thr Glu Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu

```
                     85                  90                  95
Thr Phe Gly Ala Gly Thr Lys Leu Glu Leu Lys Arg
                100                 105

<210> SEQ ID NO 33
<211> LENGTH: 108
<212> TYPE: PRT
<213> ORGANISM: Artificial Sequence
<220> FEATURE:
<223> OTHER INFORMATION: synthetic peptide

<400> SEQUENCE: 33

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
                100                 105

<210> SEQ ID NO 34
<211> LENGTH: 8
<212> TYPE: PRT
<213> ORGANISM: Artificial Sequence
<220> FEATURE:
<223> OTHER INFORMATION: synthetic peptide

<400> SEQUENCE: 34

Gly Phe Thr Phe Ser Thr Phe Thr
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic peptide

<400> SEQUENCE: 35

Ile Asn Gly Gly Gly Gly Asn Thr
1               5

<210> SEQ ID NO 36
<211> LENGTH: 11
<212> TYPE: PRT
<213> ORGANISM: Artificial Sequence
<220> FEATURE:
<223> OTHER INFORMATION: synthetic peptide

<400> SEQUENCE: 36

Ser Arg Leu Tyr Gly Ile Tyr Ala Met Asp Tyr
1               5                   10

<210> SEQ ID NO 37
<211> LENGTH: 10
<212> TYPE: PRT
<213> ORGANISM: Artificial Sequence
```

```
<220> FEATURE:
<223> OTHER INFORMATION: synthetic peptide

<400> SEQUENCE: 37

Gly Phe Thr Phe Ser Thr Phe Thr Met Ser
1               5                   10

<210> SEQ ID NO 38
<211> LENGTH: 17
<212> TYPE: PRT
<213> ORGANISM: Artificial Sequence
<220> FEATURE:
<223> OTHER INFORMATION: synthetic peptide

<400> SEQUENCE: 38

Thr Ile Asn Gly Gly Gly Asn Thr Tyr Tyr Pro Asp Ser Val Lys
1               5                   10                  15

Gly

<210> SEQ ID NO 39
<211> LENGTH: 9
<212> TYPE: PRT
<213> ORGANISM: Artificial Sequence
<220> FEATURE:
<223> OTHER INFORMATION: synthetic peptide

<400> SEQUENCE: 39

Leu Tyr Gly Ile Tyr Ala Met Asp Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: synthetic peptide

<400> SEQUENCE: 40

Gln Asp Val Gly Ser Ala
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic peptide

<400> SEQUENCE: 41

Gln Gln Tyr Ser Ser Tyr Pro Leu Thr
1               5

<210> SEQ ID NO 42
<211> LENGTH: 11
<212> TYPE: PRT
<213> ORGANISM: Artificial Sequence
<220> FEATURE:
<223> OTHER INFORMATION: synthetic peptide

<400> SEQUENCE: 42

Lys Ala Ser Gln Asp Val Gly Ser Ala Val Ala
1               5                   10

<210> SEQ ID NO 43
<211> LENGTH: 7
<212> TYPE: PRT
<213> ORGANISM: Artificial Sequence
```

```
<220> FEATURE:
<223> OTHER INFORMATION: synthetic peptide

<400> SEQUENCE: 43

Trp Thr Ser Thr Arg His Thr
1               5

<210> SEQ ID NO 44
<211> LENGTH: 6
<212> TYPE: PRT
<213> ORGANISM: Artificial Sequence
<220> FEATURE:
<223> OTHER INFORMATION: synthetic peptide

<400> SEQUENCE: 44

Glu Asn Val Val Thr Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic peptide

<400> SEQUENCE: 45

Gly Gln Gly Tyr Ser Tyr Pro Tyr Thr
1               5

<210> SEQ ID NO 46
<211> LENGTH: 11
<212> TYPE: PRT
<213> ORGANISM: Artificial Sequence
<220> FEATURE:
<223> OTHER INFORMATION: synthetic peptide

<400> SEQUENCE: 46

Lys Ala Ser Glu Asn Val Val Thr Tyr Val Ser
1               5                   10

<210> SEQ ID NO 47
<211> LENGTH: 7
<212> TYPE: PRT
<213> ORGANISM: Artificial Sequence
<220> FEATURE:
<223> OTHER INFORMATION: synthetic peptide

<400> SEQUENCE: 47

Gly Ala Ser Asn Arg Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide

<400> SEQUENCE: 48

Gly Gln Gly Tyr Ser Tyr Pro Tyr Thr
1               5

<210> SEQ ID NO 49
<211> LENGTH: 137
<212> TYPE: PRT
<213> ORGANISM: Artificial Sequence
<220> FEATURE:
<223> OTHER INFORMATION: synthetic peptide
```

<400> SEQUENCE: 49

Met Asn Phe Gly Leu Ser Leu Val Phe Leu Val Leu Ile Leu Lys Gly
1               5                   10                  15

Val Gln Cys Glu Val Met Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Phe Thr Met Ser Trp Val Arg Gln Thr Pro Glu Lys Arg Leu
    50                  55                  60

Glu Cys Val Ala Thr Ile Asn Gly Gly Gly Asn Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Phe
            100                 105                 110

Tyr Phe Cys Ser Arg Leu Tyr Gly Ile Tyr Ala Met Asp Tyr Trp Gly
        115                 120                 125

Gln Gly Thr Ser Val Thr Val Ser Ser
    130                 135

<210> SEQ ID NO 50
<211> LENGTH: 128
<212> TYPE: PRT
<213> ORGANISM: Artificial Sequence
<220> FEATURE:
<223> OTHER INFORMATION: synthetic peptide

<400> SEQUENCE: 50

Met Lys Ser His Thr Gln Val Phe Val Tyr Met Leu Leu Trp Leu Ser
1               5                   10                  15

Gly Val Glu Gly Asp Ile Val Met Thr Gln Ser His Ile Phe Met Ser
            20                  25                  30

Thr Ser Val Gly Asp Arg Val Ser Ile Thr Cys Lys Ala Ser Gln Asp
        35                  40                  45

Val Gly Ser Ala Val Ala Trp Tyr Gln Gln Lys Pro Gly Gln Ser Pro
    50                  55                  60

Lys Val Leu Ile Tyr Trp Thr Ser Thr Arg His Thr Gly Val Pro Asp
65                  70                  75                  80

Arg Phe Ala Gly Ser Gly Ser Gly Thr Glu Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys Arg
        115                 120                 125

<210> SEQ ID NO 51
<211> LENGTH: 128
<212> TYPE: PRT
<213> ORGANISM: Artificial Sequence
<220> FEATURE:
<223> OTHER INFORMATION: synthetic peptide

<400> SEQUENCE: 51

Met Lys Ser His Thr Gln Val Phe Val Ser Ile Leu Leu Trp Leu Tyr
1               5                   10                  15

Gly Ala Asp Gly Asn Ile Val Met Thr Gln Ser Pro Lys Ser Met Ser
            20                  25                  30

```
Met Ser Val Gly Glu Arg Val Thr Leu Thr Cys Lys Ala Ser Glu Asn
        35                  40                  45
Val Val Thr Tyr Val Ser Trp Tyr Gln Gln Lys Pro Glu Gln Ser Pro
    50                  55                  60
Lys Leu Leu Ile Tyr Gly Ala Ser Asn Arg Tyr Thr Gly Val Pro Asp
65                  70                  75                  80
Arg Phe Thr Gly Ser Gly Ser Ala Thr Asp Phe Thr Leu Thr Ile Ser
                85                  90                  95
Ser Val Gln Ala Glu Asp Leu Ala Asp Tyr His Cys Gly Gln Gly Tyr
            100                 105                 110
Ser Tyr Pro Tyr Thr Phe Gly Gly Gly Thr Lys Leu Glu Ile Lys Arg
        115                 120                 125

<210> SEQ ID NO 52
<211> LENGTH: 117
<212> TYPE: PRT
<213> ORGANISM: Artificial Sequence
<220> FEATURE:
<223> OTHER INFORMATION: synthetic peptide

<400> SEQUENCE: 52

Asp Val Gln Leu Gln Glu Ser Gly Pro Gly Leu Val Lys Pro Ser Glu
1               5                   10                  15
Thr Leu Ser Leu Thr Cys Ser Val Thr Gly Tyr Ser Ile Thr Ser Gly
            20                  25                  30
Tyr Tyr Trp Asn Trp Ile Arg Gln Pro Pro Gly Lys Gly Leu Glu Trp
        35                  40                  45
Met Gly Tyr Ile Arg Tyr Asp Gly Asn Asn Asn Tyr Asn Pro Ser Leu
    50                  55                  60
Lys Asn Arg Ile Thr Ile Ser His Asp Thr Ser Lys Asn Gln Phe Ser
65                  70                  75                  80
Leu Lys Leu Ser Ser Val Thr Ala Ala Asp Thr Ala Thr Tyr Tyr Cys
                85                  90                  95
Ala Arg Gly Leu Gln Phe Tyr Phe Asp Ser Trp Gly Gln Gly Thr Thr
            100                 105                 110
Val Thr Val Ser Ser
        115

<210> SEQ ID NO 53
<211> LENGTH: 114
<212> TYPE: PRT
<213> ORGANISM: Artificial Sequence
<220> FEATURE:
<223> OTHER INFORMATION: synthetic peptide

<400> SEQUENCE: 53

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Asn Gly
            20                  25                  30
Ser Tyr Gln Lys His Thr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
```

-continued

Tyr Tyr Ser Tyr Pro Trp Thr Phe Gly Gln Gly Thr Lys Leu Glu Ile
            100                 105                 110
Lys Arg

<210> SEQ ID NO 54
<211> LENGTH: 118
<212> TYPE: PRT
<213> ORGANISM: Artificial Sequence
<220> FEATURE:
<223> OTHER INFORMATION: synthetic peptide

<400> SEQUENCE: 54

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Thr Met Ser Trp Val Arg Gln Ala Pro Gly Lys Gly Leu Glu Cys Val
        35                  40                  45

Ala Thr Ile Asn Gly Gly Gly Asn Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Phe Tyr Phe Cys
                85                  90                  95

Ser Arg Leu Tyr Gly Ile Tyr Ala Met Asp Tyr Trp Gly Gln Gly Thr
            100                 105                 110

Thr Val Thr Val Ser Ser
        115

<210> SEQ ID NO 55
<211> LENGTH: 108
<212> TYPE: PRT
<213> ORGANISM: Artificial Sequence
<220> FEATURE:
<223> OTHER INFORMATION: synthetic peptide

<400> SEQUENCE: 55

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Ser Ala
            20                  25                  30

Val Ala Trp Tyr Gln Gln Lys Pro Gly Lys Ala Pro Lys Val Leu Ile
        35                  40                  45

Tyr Trp Thr Ser Thr Arg His Thr Gly Val Pro Asp Arg Phe Ala Gly
    50                  55                  60

Ser Gly Ser Gly Thr Glu Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Leu
                85                  90                  95

Thr Phe Gly Gln Gly Thr Lys Leu Glu Leu Lys Arg
            100                 105

<210> SEQ ID NO 56
<211> LENGTH: 108
<212> TYPE: PRT
<213> ORGANISM: Artificial Sequence
<220> FEATURE:
<223> OTHER INFORMATION: synthetic peptide

<400> SEQUENCE: 56

```
Asn Ile Val Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Leu Gln Pro
65                  70                  75                  80

Glu Asp Phe Ala Asp Tyr His Cys Gly Gln Gly Tyr Ser Tyr Pro Tyr
                85                  90                  95

Thr Phe Gly Gln Gly Thr Lys Leu Glu Ile Lys Arg
            100                 105
```

<210> SEQ ID NO 57
<211> LENGTH: 5
<212> TYPE: PRT
<213> ORGANISM: Artificial Sequence
<220> FEATURE:
<223> OTHER INFORMATION: synthetic peptide

<400> SEQUENCE: 57

```
Gly Gly Gly Gly Ser
1               5
```

<210> SEQ ID NO 58
<211> LENGTH: 7
<212> TYPE: PRT
<213> ORGANISM: Artificial Sequence
<220> FEATURE:
<223> OTHER INFORMATION: synthetic peptide

<400> SEQUENCE: 58

```
Gly Gly Gly Ser Ala Ala Ala
1               5
```

<210> SEQ ID NO 59
<211> LENGTH: 9
<212> TYPE: PRT
<213> ORGANISM: Artificial Sequence
<220> FEATURE:
<223> OTHER INFORMATION: synthetic peptide

<400> SEQUENCE: 59

```
Pro Gly Ser Ala Gly Gly Ser Gly Gly
1               5
```

<210> SEQ ID NO 60
<211> LENGTH: 506
<212> TYPE: PRT
<213> ORGANISM: Artificial Sequence
<220> FEATURE:
<223> OTHER INFORMATION: synthetic peptide

<400> SEQUENCE: 60

```
Met Val Leu Ser Leu Leu Tyr Leu Leu Thr Ala Ile Pro Gly Ile Leu
1               5                   10                  15

Ser Asp Val Gln Leu Gln Glu Ser Gly Pro Gly Leu Val Lys Pro Ser
            20                  25                  30

Gln Ser Leu Ser Leu Pro Cys Ser Val Thr Gly Tyr Ser Ile Thr Ser
        35                  40                  45

Gly Tyr Tyr Trp Asn Trp Ile Arg Gln Phe Pro Gly Asn Lys Leu Glu
```

```
            50                  55                  60
Trp Met Gly Tyr Ile Arg Tyr Asp Gly Asn Asn Asn Tyr Asn Pro Ser
 65                  70                  75                  80

Leu Lys Asn Arg Ile Ser Ile Thr His Asp Thr Ser Lys Asn Gln Phe
                 85                  90                  95

Phe Leu Lys Leu Asn Tyr Val Thr Thr Glu Asp Thr Ala Thr Tyr Tyr
                100                 105                 110

Cys Ala Arg Gly Leu Gln Phe Tyr Phe Asp Ser Trp Gly Gln Gly Thr
                115                 120                 125

Thr Leu Thr Val Ser Ser Gly Gly Gly Ser Gly Gly Gly Gly Ser
130                 135                 140

Gly Gly Gly Gly Ser Asp Ile Val Met Ser Gln Ser Pro Ser Ser Leu
145                 150                 155                 160

Ala Val Ser Gly Gly Glu Lys Val Thr Met Ser Cys Lys Ser Ser Gln
                165                 170                 175

Ser Leu Leu Asn Gly Ser Tyr Gln Lys His Thr Leu Ala Trp Tyr Gln
                180                 185                 190

Gln Lys Pro Gly Gln Ser Pro Lys Leu Leu Ile Tyr Trp Ala Ser Thr
                195                 200                 205

Arg Glu Ser Gly Val Pro Asp Arg Phe Thr Gly Ser Gly Ser Gly Thr
210                 215                 220

Asp Phe Thr Leu Thr Ile Ser Ser Val Lys Ala Glu Asp Leu Ala Val
225                 230                 235                 240

Tyr Tyr Cys Gln Gln Tyr Tyr Ser Tyr Pro Trp Thr Phe Gly Gly Gly
                245                 250                 255

Thr Lys Leu Glu Ile Lys Arg Pro Gly Ser Ala Gly Gly Ser Gly Gly
                260                 265                 270

Asp Ser Glu Pro Lys Ser Cys Asp Lys Thr His Thr Cys Pro Pro Cys
                275                 280                 285

Pro Ala Pro Glu Leu Leu Gly Gly Pro Ser Val Phe Leu Phe Pro Pro
                290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
                340                 345                 350

Glu Gln Tyr Asn Ser Thr Tyr Arg Val Val Ser Val Leu Thr Val Leu
                355                 360                 365

His Gln Asp Trp Leu Asn Gly Lys Glu Tyr Lys Cys Lys Val Ser Asn
                370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Tyr Cys Leu Val Lys Gly Phe Tyr
                420                 425                 430

Pro Ser Asp Ile Ala Val Glu Trp Glu Ser Asn Gly Gln Pro Glu Asn
                435                 440                 445

Asn Tyr Lys Thr Thr Pro Pro Val Leu Asp Ser Asp Gly Ser Phe Phe
                450                 455                 460

Leu Tyr Ser Lys Leu Thr Val Asp Lys Ser Arg Trp Gln Gln Gly Asn
465                 470                 475                 480
```

```
Val Phe Ser Cys Ser Val Met His Glu Ala Leu His Asn His Tyr Thr
                485                 490                 495
Gln Lys Ser Leu Ser Leu Ser Pro Gly Lys
        500                 505
```

<210> SEQ ID NO 61
<211> LENGTH: 496
<212> TYPE: PRT
<213> ORGANISM: Artificial Sequence
<220> FEATURE:
<223> OTHER INFORMATION: synthetic peptide

<400> SEQUENCE: 61

```
Met Lys Ser His Thr Gln Val Phe Val Tyr Met Leu Leu Trp Leu Ser
1               5                   10                  15
Gly Val Glu Gly Asp Ile Val Met Thr Gln Ser His Ile Phe Met Ser
            20                  25                  30
Thr Ser Val Gly Asp Arg Val Ser Ile Thr Cys Lys Ala Ser Gln Asp
        35                  40                  45
Val Gly Ser Ala Val Ala Trp Tyr Gln Gln Lys Pro Gly Gln Ser Pro
    50                  55                  60
Lys Val Leu Ile Tyr Trp Thr Ser Thr Arg His Thr Gly Val Pro Asp
65                  70                  75                  80
Arg Phe Ala Gly Ser Gly Ser Gly Thr Glu Phe Thr Leu Thr Ile Ser
                85                  90                  95
Asn Val Gln Ser Glu Asp Leu Ala Asp Tyr Phe Cys Gln Gln Tyr Ser
            100                 105                 110
Ser Tyr Pro Leu Thr Phe Gly Ala Gly Thr Lys Leu Glu Leu Lys Arg
        115                 120                 125
Gly Gly Gly Ser Ala Ala Ala Glu Val Met Leu Val Glu Ser Gly Gly
    130                 135                 140
Gly Leu Val Lys Pro Gly Gly Ser Leu Lys Leu Ser Cys Ala Ala Ser
145                 150                 155                 160
Gly Phe Thr Phe Ser Thr Phe Thr Met Ser Trp Val Arg Gln Thr Pro
                165                 170                 175
Glu Lys Arg Leu Glu Cys Val Ala Thr Ile Asn Gly Gly Gly Gly Asn
            180                 185                 190
Thr Tyr Tyr Pro Asp Ser Val Lys Gly Arg Phe Thr Ile Ser Arg Asp
        195                 200                 205
Asn Ala Lys Asn Asn Leu Tyr Leu Gln Met Ser Ser Leu Arg Ser Glu
    210                 215                 220
Asp Thr Ala Phe Tyr Phe Cys Ser Arg Leu Tyr Gly Ile Tyr Ala Met
225                 230                 235                 240
Asp Tyr Trp Gly Gln Gly Thr Ser Val Thr Val Ser Ser Pro Gly Ser
                245                 250                 255
Ala Gly Gly Ser Gly Gly Asp Ser Glu Pro Lys Ser Cys Asp Lys Thr
            260                 265                 270
His Thr Cys Pro Pro Cys Pro Ala Pro Glu Leu Leu Gly Gly Pro Ser
        275                 280                 285
Val Phe Leu Phe Pro Pro Lys Pro Lys Asp Thr Leu Met Ile Ser Arg
    290                 295                 300
Thr Pro Glu Val Thr Cys Val Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
```

```
                   340                 345                 350
Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
            435                 440                 445

Ser Asp Gly Ser Phe Phe Leu Thr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 62
<211> LENGTH: 707
<212> TYPE: PRT
<213> ORGANISM: Artificial Sequence
<220> FEATURE:
<223> OTHER INFORMATION: synthetic peptide

<400> SEQUENCE: 62

Met Val Leu Ser Leu Leu Tyr Leu Leu Thr Ala Ile Pro Gly Ile Leu
1               5                   10                  15

Ser Asp Val Gln Leu Gln Glu Ser Gly Pro Gly Leu Val Lys Pro Ser
            20                  25                  30

Gln Ser Leu Ser Leu Pro Cys Ser Val Thr Gly Tyr Ser Ile Thr Ser
        35                  40                  45

Gly Tyr Tyr Trp Asn Trp Ile Arg Gln Phe Pro Gly Asn Lys Leu Glu
    50                  55                  60

Trp Met Gly Tyr Ile Arg Tyr Asp Gly Asn Asn Tyr Asn Pro Ser
65                  70                  75                  80

Leu Lys Asn Arg Ile Ser Ile Thr His Asp Thr Ser Lys Asn Gln Phe
                85                  90                  95

Phe Leu Lys Leu Asn Tyr Val Thr Thr Glu Asp Thr Ala Thr Tyr Tyr
            100                 105                 110

Cys Ala Arg Gly Leu Gln Phe Tyr Phe Asp Ser Trp Gly Gln Gly Thr
        115                 120                 125

Thr Leu Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
210                 215                 220
```

```
Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Gly Gly Gly Gly Ser Gly Gly Gly Ser Asp Ile Val Met Thr Gln
465                 470                 475                 480

Ser His Ile Phe Met Ser Thr Ser Val Gly Asp Arg Val Ser Ile Thr
                485                 490                 495

Cys Lys Ala Ser Gln Asp Val Ser Ala Val Ala Trp Tyr Gln Gln
            500                 505                 510

Lys Pro Gly Gln Ser Pro Lys Val Leu Ile Tyr Trp Thr Ser Thr Arg
        515                 520                 525

His Thr Gly Val Pro Asp Arg Phe Ala Gly Ser Gly Ser Gly Thr Glu
    530                 535                 540

Phe Thr Leu Thr Ile Ser Asn Val Gln Ser Glu Asp Leu Ala Asp Tyr
545                 550                 555                 560

Phe Cys Gln Gln Tyr Ser Ser Tyr Pro Leu Thr Phe Gly Ala Gly Thr
                565                 570                 575

Lys Leu Glu Leu Lys Arg Gly Gly Gly Ser Ala Ala Ala Glu Val Met
            580                 585                 590

Leu Val Glu Ser Gly Gly Gly Leu Val Lys Pro Gly Gly Ser Leu Lys
        595                 600                 605

Leu Ser Cys Ala Ala Ser Gly Phe Thr Phe Ser Thr Phe Thr Met Ser
    610                 615                 620

Trp Val Arg Gln Thr Pro Glu Lys Arg Leu Glu Cys Val Ala Thr Ile
625                 630                 635                 640

Asn Gly Gly Gly Gly Asn Thr Tyr Tyr Pro Asp Ser Val Lys Gly Arg
```

```
                    645                 650                 655
Phe Thr Ile Ser Arg Asp Asn Ala Lys Asn Asn Leu Tyr Leu Gln Met
                660                 665                 670

Ser Ser Leu Arg Ser Glu Asp Thr Ala Phe Tyr Phe Cys Ser Arg Leu
            675                 680                 685

Tyr Gly Ile Tyr Ala Met Asp Tyr Trp Gly Gln Gly Thr Ser Val Thr
        690                 695                 700

Val Ser Ser
705
```

<210> SEQ ID NO 63
<211> LENGTH: 1407
<212> TYPE: DNA
<213> ORGANISM: Artificial Sequence
<220> FEATURE:
<223> OTHER INFORMATION: synthetic polynucleotide

<400> SEQUENCE: 63

| | | | | | |
|---|---|---|---|---|---|
| atggactgga | cctggcgggt | gttctgcctg | ctggctgtgg | ctcctggcgc | ccactctcag | 60 |
| gtgcgactgg | tgcagtccgg | caccgaagtg | aagaaacctg | gcgcctccgt | gcgggtgtcc | 120 |
| tgcaaggctt | ccggctacac | cttctccaac | tactacatgt | actgggtgcg | acaggctcca | 180 |
| ggacagggcc | tggaatggat | ggccatgatc | aacccctccg | gcggctccac | cagatacgcc | 240 |
| cagaaattcc | agggcagagt | gaccatgacc | cgggacacct | ccacttccac | cgtgtacatg | 300 |
| gaactgtcct | ccctgcggag | cgaagacacc | gccgtgtact | actgcgccag | agccgactcc | 360 |
| ggctcctact | tcggctactg | gggccagggc | accctggtga | cagtgtcctc | cgcctccacc | 420 |
| aagggcccct | ccgtgtttcc | tctggccccc | tccagcaagt | ccacctctgg | cggcaccgcc | 480 |
| gctctgggct | gcctggtgaa | agactacttc | cccgagcccg | tgaccgtgtc | ctggaactct | 540 |
| ggcgccctga | ccagcggagt | gcataccttc | ccgccgtgc | tgcagtcctc | cggcctgtac | 600 |
| tccctgtcct | ccgtggtgac | cgtgccctcc | agctctctgg | gcacccagac | ctacatctgc | 660 |
| aacgtgaacc | acaagccctc | caacaccaag | gtggacaaga | aggtggaacc | caagtcctgc | 720 |
| gacaagaccc | acacctgtcc | ccctgccct | gcccctgaac | tgctgggagg | cccttctgtg | 780 |
| ttcctgttcc | ccccaaagcc | caaggacacc | ctgatgatct | cccggacccc | cgaagtgacc | 840 |
| tgcgtggtgg | tggacgtgtc | ccacgaggac | cctgaagtga | agttcaattg | gtacgtggac | 900 |
| ggcgtggaag | tgcataacgc | caagaccaag | cccagagagg | aacagtacaa | ctccacctac | 960 |
| cgggtggtgt | ctgtgctgac | cgtgctgcac | caggactggc | tgaacggcaa | agagtacaag | 1020 |
| tgcaaggtct | ccaacaaggc | cctgccagcc | cccatcgaaa | agaccatctc | caaggccaag | 1080 |
| ggccagcccc | gcgagcctca | ggtgtacacc | ctgcctccca | gccgggacga | gctgaccaag | 1140 |
| aaccaggtgt | ccctgacctg | tctggtgaaa | ggattctacc | cctccgatat | cgccgtggaa | 1200 |
| tgggagtcca | acggacagcc | cgagaacaac | tacaagacca | cccccctgt | gctggactcc | 1260 |
| gacggctcat | tcttcctgta | ctccaagctg | accgtggaca | agtcccggtg | gcagcagggc | 1320 |
| aacgtgttct | cctgctccgt | gatgcacgag | gccctgcaca | accactacac | ccagaagtcc | 1380 |
| ctgtccctga | gccccggcaa | gtgatga | | | | 1407 |

<210> SEQ ID NO 64
<211> LENGTH: 708
<212> TYPE: DNA
<213> ORGANISM: Artificial Sequence
<220> FEATURE:
<223> OTHER INFORMATION: synthetic polynucleotide

<400> SEQUENCE: 64

```
atgagagtgc ctgctcagct gctgggcctg ctgctgctgt ggctgcctgg cgccagatgc    60
gacatccagc tgacccagtc ccccagcttc ctgtccgcct ccgtgggcga ccgggtgcca   120
atcacctgtc gggcctccca gggcatctcc acccacctgg cctggtatca gcagaagccc   180
ggcaaggccc ccaagctgct gatctacgcc gcctccaccc tgcagtccgg cgtgccctcc   240
agattctccg gctctggctc cggcaccgag ttcaccctga ccatctccag cctgcagccc   300
gaggactccg ccacctacta ctgccagcag ctgaagtcct acccctgac cttcggcgga   360
ggcaccaagg tggaaatcaa gcggaccgtg gccgctccct ccgtgttcat cttcccaccc   420
tccgacgagc agctgaaatc cggcaccgcc agcgtggtgt gcctgctgaa caacttctac   480
ccccgcgagg ccaaggtgca gtggaaggtg gacaacgccc tgcagagcgg caactcccag   540
gaatccgtca ccgagcagga ctccaaggac agcacctact ccctgtccag cacctgacc   600
ctgtccaagg ccgactacga gaagcacaag gtgtacgcct gcgaagtgac ccaccagggc   660
ctgtccagcc ctgtgaccaa gtccttcaac cggggcgagt gctgatga            708
```

<210> SEQ ID NO 65
<211> LENGTH: 1521
<212> TYPE: DNA
<213> ORGANISM: Artificial Sequence
<220> FEATURE:
<223> OTHER INFORMATION: synthetic polynucleotide

<400> SEQUENCE: 65

```
atggtgctgt ctctgctgta cctgctgacc gccatcccg gcatcctgtc cgacgtgcag    60
ctgcaggaat ccggccctgg cctggtgaaa ccctcccagt ccctgtccct gccttgctcc   120
gtgaccggct actccatcac ctccggctac tactggaact ggatcagaca gttccccggc   180
aacaagctgg aatggatggg ctacatccgc tacgacggca caacaacta caaccccagc   240
ctgaagaacc ggatctctat cacccacgac acctccaaga ccagttctt cctgaagctg   300
aactacgtga ccaccgagga caccgccacc tactactgcg ccagaggcct gcagttctac   360
ttcgactcct ggggccaggg caccaccctg acagtgtcta gcggcggagg cggaagcgga   420
gggggaggat ctggcggcgg aggatctgac atcgtgatgt cccagtcccc ctcctccctg   480
gctgtgtctg gcggcgagaa agtgaccatg tcctgcaagt cctcccagag cctgctgaac   540
ggctcctacc agaagcacac cctggcttgg tatcagcaga agcccggcca gtcccccaag   600
ctgctgatct actgggcctc caccgcgag tccggcgtgc cagacagatt caccggctcc   660
ggcagcggca ccgacttcac cctgaccatc tccagcgtga aggccgagga cctggccgtg   720
tactactgcc agcagtacta ctcctacccc tggaccttcg gaggaggcac aaagctggaa   780
atcaagcggc ctggctccgc tggcggctct ggcggagact ccgagcccaa gtcctgcgac   840
aagacccaca cctgtccccc ctgccctgcc ctgaactgc tgggcggacc ctccgtgttc   900
ctgttccccc caaagcccaa ggacaccctg atgatctccc ggaccccga agtgacctgc   960
gtggtggtgg acgtgtccca cgaggaccct gaagtgaagt tcaattggta cgtggacggc  1020
gtggaagtgc acaacgccaa gaccaagccc agagaggaac agtacaactc cacctaccgg  1080
gtggtgtccg tgctgaccgt gctgcaccag gactggctga acggcaaaga gtacaagtgc  1140
aaggtgtcca acaaggccct gcctgccccc atcgaaaaga ccatcagcaa ggccaagggc  1200
cagccccgcg agcctcaggt gtacaccctg cctcccagcc gggacgagct gaccaagaat  1260
caggtgtccc tgtactgtct ggtgaaaggc ttctaccccc ccgatatcgc cgtggaatgg  1320
```

```
gagtccaacg dcagcccga gaacaattac aagaccaccc ccctgtgct ggactccgac    1380 ggctcattct tcctgtactc caagctgacc gtggacaagt cccggtggca gcagggcaac    1440
gtgttctcct gctccgtgat gcacgaggcc ctgcacaacc actaccccca gaagtccctg    1500
agcctgtccc ccggcaagtg a                                               1521

<210> SEQ ID NO 66
<211> LENGTH: 1491
<212> TYPE: DNA
<213> ORGANISM: Artificial Sequence
<220> FEATURE:
<223> OTHER INFORMATION: synthetic polynucleotide

<400> SEQUENCE: 66
atgaagtccc acacccaggt gttcgtgtac atgctgctgt ggctgtccgg cgtggaaggc      60
gacatcgtga tgacccagtc ccacatcttc atgtccacct ccgtgggcga ccgggtgtcc     120
atcacatgca aggcctccca ggacgtgggc tctgccgtgg cctggtatca gcagaagccc     180
ggccagtccc ccaaggtgct gatctactgg acctccaccc ggcataccgg cgtgccagac     240
agattcgccg gctctggctc cggcaccgag ttcaccctga ccatctccaa cgtgcagtcc     300
gaggacctgg ccgactactt ctgccagcag tactcctcct acccctgac cttcggcgct      360 ggcaccaagc tggaactgaa acggggaggc ggctccgccg ctgctgaagt gatgctggtg     420
gaatccggcg gaggcctggt gaaacctggc ggctccctga gctgtcctg cgctgcctct      480 ggcttcacct tctccacctt caccatgtcc tgggtgcgac agaccccga gaagcggctg     540 gaatgcgtgg ccaccatcaa cggcggaggc ggcaacacct actacccga ctccgtgaag     600 ggccggttca ccatctcccg ggacaacgcc aagaacaacc tgtacctgca gatgtcctcc     660
ctgcggagcg aggataccgc cttctacttc tgctcccggc tgtacggcat ctacgccatg     720
gactactggg gccagggcac ctccgtgacc gtgtcctctc ctggctctgc tggcggctct     780
ggcggcgact ccgagcctaa gtcctgcgac aagacccaca cctgtccccc ttgccctgcc     840
cctgaactgc tgggcggacc ctccgtgttc ctgttcccc caaagcccaa ggacaccctg     900
atgatctccc ggacccccga agtgacctgc gtggtggtgg acgtgtccca cgaggaccct     960
gaagtgaagt tcaattggta cgtggacggg gtggaagtgc acaatgccaa gaccaagccc    1020
agagaggaac agtacaactc cacctaccgg gtggtgtccg tgctgaccgt gctgcaccag    1080
gactggctga acggcaaaga gtacaagtgc aaggtgtcca acaaggccct gcctgccccc    1140
atcgaaaaga ccatcagcaa ggctaagggc cagccccgcg agcctcaggt gtacaccctg    1200
cctcccagcc gggacgagct gaccaagaac caggtgtccc tgacctgtct ggtgaaaggc    1260
ttctacccct ccgatatcgc cgtggaatgg gagtccaacg gccagcccga gaacaactac    1320
aagaccaccc ccctgtgct ggactccgac ggctcattct tcctgacctc caagctgacc    1380
gtggacaagt cccggtggca gcagggcaac gtgttctcct gctccgtgat gcacgaggcc    1440
ctgcacaacc actaccccca gaagtccctg tccctgagcc ccggcaagtg a              1491

<210> SEQ ID NO 67
<211> LENGTH: 2124
<212> TYPE: DNA
<213> ORGANISM: Artificial Sequence
<220> FEATURE:
<223> OTHER INFORMATION: synthetic polynucleotide

<400> SEQUENCE: 67
atggtcctgt ccctgctgta cctgctgacc gccatccccg gcatcctgtc cgacgtccag      60
```

-continued

| | |
|---|---|
| ctgcaggaat ccggccctgg cctggtcaag ccctcccagt ccctgagcct gccctgctct | 120 |
| gtgaccggct actccatcac ctccggctac tactggaact ggatcagaca gttcccggc | 180 |
| aacaagctgg aatggatggg ctacatcaga tacgacggca acaacaacta caaccccagc | 240 |
| ctgaagaacc ggatcagcat cacccacgac acctccaaga accagttctt cctgaagctg | 300 |
| aactacgtga ccaccgagga caccgccacc tactactgcg ccagaggcct gcagttctac | 360 |
| ttcgactcct ggggccaggg caccaccctg accgtgtcct ccgcctctac caagggcccc | 420 |
| tccgtgttcc ctctggcccc ctccagcaag tctacctctg cggcaccgc cgctctgggc | 480 |
| tgtctggtca aggactactt ccccgagccc gtgacagtgt cctggaactc tggcgccctg | 540 |
| acctccggcg tgcacacctt ccagccgtg ctgcagtcct ccggcctgta ctccctgtcc | 600 |
| tccgtcgtga ccgtgccttc ctccagcctg ggcacccaga cctacatctg caacgtgaac | 660 |
| cacaagcctt ccaacaccaa ggtggacaag aaggtggaac ccaagtcctg cgacaagacc | 720 |
| cacacctgtc ccccttgccc tgcccctgag ctgctgggag ccctagcgt gttcctgttc | 780 |
| cccccaaagc ccaaggacac cctgatgatc tcccggaccc ccgaagtgac ctgcgtggtg | 840 |
| gtggacgtgt cccacgagga ccctgaagtg aagttcaatt ggtacgtgga cggcgtggaa | 900 |
| gtgcacaacg ccaagaccaa gccagagag gaacagtaca actccaccta ccgggtggtg | 960 |
| tccgtgctga cagtgctgca ccaggactgg ctgaacggca agagtacaa gtgcaaggtg | 1020 |
| tccaacaagg ccctgcctgc ccccatcgaa aagaccatct ccaaggccaa gggccagccc | 1080 |
| cgcgagcccc aggtgtacac actgcctcca tcccgggacg agctgaccaa gaatcaggtg | 1140 |
| tccctgacat gcctggtcaa aggcttctac ccctccgata tcgccgtgga atgggagtcc | 1200 |
| aacggccagc cagagaacaa ttacaagacc ccccccctg tgctggactc cgacggctca | 1260 |
| ttcttcctgt acagcaagct gaccgtggac aagtcccggt ggcagcaggg caacgtgttc | 1320 |
| tcctgctccg tgatgcacga ggccctgcac aaccactaca cccagaagtc cctgtctctg | 1380 |
| tcccccggca aggcggagg aggatctggt ggcggaggct ccgacatcgt gatgacccag | 1440 |
| tcccacatct tcatgtccac cagcgtgggc gaccgggtgt ccatcacatg caaggcctct | 1500 |
| caggacgtgg gctccgccgt ggcctggtat cagcagaagc ccggccagtc ccccaaggtg | 1560 |
| ctgatctact ggacctccac ccggcacacc ggcgtgcccg atagatttgc cggctccggc | 1620 |
| agcggcaccg agtttaccct gaccatcagc aacgtgcagt ccgaggacct ggccgactac | 1680 |
| ttctgccagc agtactcctc ctaccccctg accttggcg ctggcacaaa gctggaactg | 1740 |
| aagaggggcg aggatcagc cgccgctgaa gtgatgctgg tggaatctgg cggcggactg | 1800 |
| gtcaaacctg gcggctctct gaagctgtcc tgcgccgcca gcggcttcac cttctccacc | 1860 |
| ttcaccatgt cctgggtccg acagacccc gagaagcggc tggaatgcgt ggccaccatc | 1920 |
| aatggcggcg gtggcaatac ctactacccc gactccgtga agggccggtt caccatctcc | 1980 |
| cgggacaatg ccaagaacaa cctgtacctg cagatgtcct ccctgcggag cgaggatacc | 2040 |
| gccttctact tctgttcccg gctgtacggc atctacgcca tggactattg gggacaggga | 2100 |
| acctctgtga ctgtgtccag ctga | 2124 |

<210> SEQ ID NO 68
<211> LENGTH: 708
<212> TYPE: DNA
<213> ORGANISM: Artificial Sequence
<220> FEATURE:
<223> OTHER INFORMATION: synthetic polynucleotide

<400> SEQUENCE: 68

-continued

| | |
|---|---|
| atggtcctga tcctgctgct gctgtgggtg tccggcacct gtggcgacat cgtgatgtcc | 60 |
| cagtccccct cctccctggc tgtgtctggc ggcgagaaag tgaccatgtc ctgcaagtcc | 120 |
| tcccagagcc tgctgaacgg ctcctaccag aagcacaccc tggcctggta tcagcagaag | 180 |
| cccggccagt cccctaagct gctgatctac tgggcctcca cccgcgagtc tggcgtgccc | 240 |
| gatcggttta ccggctccgg cagcggcacc gactttaccc tgaccatctc ctccgtgaag | 300 |
| gccgaggacc tggccgtgta ctactgccag cagtactact cctaccccctg gaccttcggc | 360 |
| ggaggcacca agctggaaat caagcggacc gtggccgctc cctccgtgtt catcttccca | 420 |
| ccctccgacg agcagctgaa gtctggcacc gcctccgtcg tgtgtctgct gaacaacttc | 480 |
| tacccccgcg aggccaaggt gcagtggaag gtggacaacg ccctgcagtc cggcaactcc | 540 |
| caggaatccg tcaccgagca ggactccaag gacagcacct actccctgtc ctccaccctg | 600 |
| accctgtcca aggccgacta tgagaagcac aaggtgtacg cctgcgaagt gacccaccag | 660 |
| ggcctgtcca gccccgtgac caagtccttc aaccggggcg agtgctga | 708 |

<210> SEQ ID NO 69
<211> LENGTH: 1395
<212> TYPE: DNA
<213> ORGANISM: Artificial Sequence
<220> FEATURE:
<223> OTHER INFORMATION: synthetic polynucleotide

<400> SEQUENCE: 69

| | |
|---|---|
| atggtcctgt ccctgctgta cctgctgacc gccatccccg gcatcctgtc cgacgtccag | 60 |
| ctgcaggaat ccggccctgg cctggtcaag ccctcccagt ccctgagcct gcctgctct | 120 |
| gtgaccggct actccatcac ctccggctac tactggaact ggatcagaca gttccccggc | 180 |
| aacaagctgg aatggatggg ctacatcaga tacgacggca caacaactaa caaccccagc | 240 |
| ctgaagaacc ggatcagcat cacccacgac acctccaaga ccagttctt cctgaagctg | 300 |
| aactacgtga ccaccgagga caccgccacc tactactgcg ccagaggcct gcagttctac | 360 |
| ttcgactcct ggggccaggg caccaccctg accgtgtcct ccgcctctac caagggcccc | 420 |
| tccgtgttcc ctctggcccc ctccagcaag tctacctctg gcggcaccgc cgctctgggc | 480 |
| tgtctggtca aggactactt ccccgagccc gtgacagtgt cctggaactc tggcgccctg | 540 |
| acctccggcg tgcacacctt tccagccgtg ctgcagtcct ccggcctgta ctccctgtcc | 600 |
| tccgtcgtga ccgtgccttc ctccagcctg ggcacccaga cctacatctg caacgtgaac | 660 |
| cacaagccct tccaacaccaa ggtggacaag aaggtggaac ccagtcctg cgacaagacc | 720 |
| cacacctgtc ccccttgccc tgcccctgag ctgctgggag ccctagcgt gttcctgttc | 780 |
| ccccccaaagc ccaaggacac cctgatgatc tcccggaccc ccgaagtgac ctgcgtggtg | 840 |
| gtggacgtgt cccacgagga ccctgaagtg aagttcaatt ggtacgtgga cggcgtggaa | 900 |
| gtgcacaacg ccaagaccaa gccagagag gaacagtaca actccaccta ccgggtggtg | 960 |
| tccgtgctga cagtgctgca ccaggactgg ctgaacggca agagtacaa gtgcaaggtg | 1020 |
| tccaacaagg ccctgcctgc ccccatcgaa aagaccatct ccaaggccaa gggccagccc | 1080 |
| cgcgagcccc aggtgtacac actgcctcca tcccgggacg agctgaccaa gaatcaggtg | 1140 |
| tccctgacat gcctggtcaa aggcttctac ccctccgata tcgccgtgga atgggagtcc | 1200 |
| aacggccagc cagagaacaa ttacaagacc accccccctg tgctggactc cgacggctca | 1260 |
| ttcttcctgt acagcaagct gaccgtggac aagtccggt ggcagcaggg caacgtgttc | 1320 |
| tcctgctccg tgatgcacga ggccctgcac aaccactaca cccagaagtc cctgtctctg | 1380 |

-continued

| tcccccggca aatga | 1395 |

<210> SEQ ID NO 70
<211> LENGTH: 708
<212> TYPE: DNA
<213> ORGANISM: Artificial Sequence
<220> FEATURE:
<223> OTHER INFORMATION: synthetic polynucleotide

<400> SEQUENCE: 70

| atggtcctga tcctgctgct gctgtgggtg tccggcacct gtggcgacat cgtgatgtcc | 60 |
| cagtccccct cctccctggc tgtgtctggc ggcgagaaag tgaccatgtc ctgcaagtcc | 120 |
| tcccagagcc tgctgaacgg ctcctaccag aagcacaccc tggcttggta tcagcagaag | 180 |
| cccggccagt cccccaagct gctgatctac tgggcctcca cccgcgagtc cggcgtgcca | 240 |
| gacagattca ccggctccgg cagcggcacc gacttcaccc tgaccatctc cagcgtgaag | 300 |
| gccgaggacc tggccgtgta ctactgccag cagtactact cctacccctg gaccttcgga | 360 |
| ggaggcacaa agctggaaat caagcggacc gtggccgctc cctccgtgtt catcttccca | 420 |
| ccctccgacg agcagctgaa gtctggcacc gcctccgtcg tgtgtctgct gaacaacttc | 480 |
| taccccgcg aggccaaggt gcagtggaag gtggacaacg ccctgcagtc cggcaactcc | 540 |
| caggaatccg tcaccgagca ggactccaag gacagcacct actccctgtc ctccaccctg | 600 |
| accctgtcca aggccgacta tgagaagcac aaggtgtacg cctgcgaagt gacccaccag | 660 |
| ggcctgtcca gccccgtgac caagtccttc aaccggggcg agtgctga | 708 |

<210> SEQ ID NO 71
<211> LENGTH: 1116
<212> TYPE: DNA
<213> ORGANISM: Artificial Sequence
<220> FEATURE:
<223> OTHER INFORMATION: synthetic polynucleotide

<400> SEQUENCE: 71

| atgaactttg ggctcagctt ggttttcctt gtcctaattt taaaaggtgt ccagtgtgaa | 60 |
| gtgatgctgg tggaatccgg cggaggcctg gtgaaacctg gcggctccct gaagctgtcc | 120 |
| tgcgctgcct ctggcttcac cttctccacc ttcaccatgt cctgggtgcg acagacccc | 180 |
| gagaagcggc tggaatgcgt ggccaccatc aacggcggag cggcaacac ctactacccc | 240 |
| gactccgtga agggccggtt caccatctcc cgggacaacg ccaagaacaa cctgtacctg | 300 |
| cagatgtcct ccctgcgcag cgaggatacc gccttctact ctgctcccg gctgtacggc | 360 |
| atctacgcca tggactactg gggccagggc acctccgtga ccgtgtcctc tgactccgag | 420 |
| cctaagtcct gcgacaagac ccacacctgt cccccttgcc ctgcccctga actgctgggc | 480 |
| ggaccctccg tgttcctgtt cccccaaag cccaaggaca ccctgatgat ctcccggacc | 540 |
| cccgaagtga cctgcgtggt ggtggacgtg tcccacgagg accctgaagt gaagttcaat | 600 |
| tggtacgtgg acggggtgga agtgcacaat gccaagacca gcccagaga ggaacagtac | 660 |
| aactccacct accgggtggt gtccgtgctg accgtgctgc accaggactg gctgaacggc | 720 |
| aaagagtaca agtgcaaggt gtccaacaag gccctgcctg cccccatcga aaagaccatc | 780 |
| agcaaggcta aggccagcc ccgcgagcct caggtgtaca ccctgcctcc cagccgggac | 840 |
| gagctgacca agaaccaggt gtccctgacc tgtctggtga aaggcttcta ccctccgat | 900 |
| atcgccgtgg aatgggagtc caacggccag ccgagaaca actacaagac caccccccct | 960 |
| gtgctggact ccgacggctc attcttcctg acctccaagc tgaccgtgga caagtcccgg | 1020 |

-continued

```
tggcagcagg gcaacgtgtt ctcctgctcc gtgatgcacg aggccctgca caaccactac    1080
acccagaagt ccctgtccct gagccccggc aagtga                              1116

<210> SEQ ID NO 72
<211> LENGTH: 705
<212> TYPE: DNA
<213> ORGANISM: Artificial Sequence
<220> FEATURE:
<223> OTHER INFORMATION: synthetic polynucleotide

<400> SEQUENCE: 72
atgaagtccc acacccaggt gttcgtgtac atgctgctgt ggctgtccgg cgtggaaggc      60
gacatcgtga tgacccagtc ccacatcttc atgtccacct ccgtgggcga ccgggtgtcc     120
atcacatgca aggcctccca ggacgtgggc tctgccgtgg cctggtatca gcagaagccc     180
ggccagtccc ccaaggtgct gatctactgg acctccaccc ggcataccgg cgtgccagac     240
agattcgccg gctctggctc cggcaccgag ttcaccctga ccatctccaa cgtgcagtcc     300
gaggacctgg ccgactactt ctgccagcag tactcctcct acccctgac cttcggcgct      360 ggcaccaagc tggaactgaa acggaccgtg gccgctccct ccgtgttcat cttcccaccc    420
tccgacgagc agctgaagtc tggcaccgcc tccgtcgtgt gtctgctgaa caacttctac    480
ccccgcgagg ccaaggtgca gtggaaggtg gacaacgccc tgcagtccgg caactcccag    540
gaatccgtca ccgagcagga ctccaaggac agcacctact ccctgtcctc caccctgacc    600
ctgtccaagg ccgactatga gaagcacaag gtgtacgcct gcgaagtgac ccaccagggc    660
ctgtccagcc ccgtgaccaa gtccttcaac cggggcgagt gctga                     705
```